US006013660A

United States Patent [19]
Horwitz et al.

[11] Patent Number: 6,013,660
[45] Date of Patent: *Jan. 11, 2000

[54] EXTERNALLY TARGETED PROPHYLACTIC AND CHEMOTHERAPEUTIC METHOD AND AGENTS

[75] Inventors: Marcus A. Horwitz; Günter Harth, both of Los Angeles, Calif.

[73] Assignee: The Regents of the University of California, Oakland, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/724,814

[22] Filed: Oct. 2, 1996

[51] Int. Cl.[7] ............................. A01N 43/50; A01N 37/12
[52] U.S. Cl. ............................ 514/401; 514/566
[58] Field of Search .................... 435/184; 514/579, 514/607; 562/401, 566

[56] References Cited

U.S. PATENT DOCUMENTS

| | | | |
|---|---|---|---|
| 3,888,837 | 6/1975 | Tsumita et al. | 260/112.5 |
| 3,943,119 | 3/1976 | Tsumita et al. | 260/112.5 R |
| 4,123,427 | 10/1978 | Daniel | 260/112 B |
| 4,285,931 | 8/1981 | Limjuco et al. | 424/92 |
| 4,460,503 | 7/1984 | Savrda et al. | 260/112.5 R |
| 4,724,144 | 2/1988 | Rook et al. | 424/88 |
| 4,777,130 | 10/1988 | Maes | 435/7 |
| 4,889,800 | 12/1989 | Shinnick et al. | 435/7 |
| 4,906,742 | 3/1990 | Young et al. | 536/27 |
| 4,952,395 | 8/1990 | Shinnick et al. | 424/92 |
| 4,965,192 | 10/1990 | Maes | 435/7 |
| 4,976,958 | 12/1990 | Shinnick et al. | 424/92 |
| 5,108,745 | 4/1992 | Horwitz | 424/92 |
| 5,154,923 | 10/1992 | Van Eden et al. | 434/88 |
| 5,169,940 | 12/1992 | Patarroyo | 536/27 |
| 5,171,839 | 12/1992 | Patarroyo | 530/326 |
| 5,225,324 | 7/1993 | McFadden et al. | 435/6 |
| 5,254,459 | 10/1993 | Patarroyo | 435/6 |
| 5,268,170 | 12/1993 | Van Eden et al. | 424/92 |

FOREIGN PATENT DOCUMENTS

| | | |
|---|---|---|
| 0499003 | 8/1992 | European Pat. Off. . |
| 0519218 | 12/1992 | European Pat. Off. . |
| 2239246 | 6/1991 | United Kingdom . |
| WO 85 03639 | 8/1985 | WIPO . |
| WO 88 02027 | 3/1988 | WIPO . |
| WO 88 05823 | 8/1988 | WIPO . |
| WO 88 06626 | 9/1988 | WIPO . |
| WO 89 05825 | 6/1989 | WIPO . |
| WO 89 12455 | 12/1989 | WIPO . |
| WO 90 00594 | 1/1990 | WIPO . |
| WO 90 02564 | 3/1990 | WIPO . |
| WO 90 10449 | 9/1990 | WIPO . |
| WO 90 15873 | 12/1990 | WIPO . |
| WO 91 04272 | 4/1991 | WIPO . |
| WO 91 14448 | 10/1991 | WIPO . |
| WO 92 01783 | 2/1992 | WIPO . |
| WO 92 01796 | 2/1992 | WIPO . |
| WO 92 04462 | 3/1992 | WIPO . |
| WO 92 16628 | 10/1992 | WIPO . |
| WO 92 21376 | 12/1992 | WIPO . |
| WO 92 21697 | 12/1992 | WIPO . |
| WO 92 22326 | 12/1992 | WIPO . |
| WO 93 07897 | 4/1993 | WIPO . |
| WO 93 14118 | 7/1993 | WIPO . |
| WO 93 14789 | 8/1993 | WIPO . |
| WO 94 02508 | 2/1994 | WIPO . |
| WO 95 01440 | 1/1995 | WIPO . |
| WO 95 01441 | 1/1995 | WIPO . |
| WO 95 14713 | 6/1995 | WIPO . |

OTHER PUBLICATIONS

Berendsen, A glimpse of the holy grail, Science, vol. 282, pp. 642–643, Oct. 1998.

McBean, Imhibition of glutamate transporter and glial enzymes in rat striatum by glioxin, [alpha]aminoadipate, Br. J. Pharm., vol. 113, pp. 536–540, 1994.

E. Ribi et al., "Induction of Resistance to Tuberculosis in Mice . . . Unrelated Materials," 1982, 345–356, Zbl.Bakt.Hyg., I.

H. Hahn, "Antibacterial Defence Mechanisms," 1983, S112–S121, Infection II (1983) Suppl.2.

I.M. Orme & F.M. Collins, "Infection with Mycobacterium kansasii and efficacy of vaccination against tuberculosis," 1983, 581–586, Immunology.

P.H. Lagrange et al., "Immunological Mechanisms Controlling Mycobacterial Infections," 1983, 163–172, Bull.europ-.Physiopath.resp.

R.A. Young et al., "Dissection of Mycobacterium tuberculosis antigens using recombinant DNA," May 1985, 82:2583–2587, Proc.Natl.Acad.Sci. USA.

B.R. Bloom et al., "Genes for the protein antigens of the tuberculosis and leprosy bacilli," 1985, 5:839–845, Science Reports.

S.H.E. Kaufmann, "T Cell Clones and their Products: . . . Infections," 1985, S177–S182, Infection 13 (1985) Suppl.2.

E. Krambovitis, "Detection of antibodies to Mycobacterium tuberculosis plasma . . . assay," 1986, 21:257–264, Med. Microbiol.

D. Young et al., "Immunological Activity . . . Mycobacterium tuberculosis," Oct. 1986, 177–183, Infection and Immunity, vol. 54, No. 1.

(List continued on next page.)

Primary Examiner—Nancy Degen
Assistant Examiner—Andrew Wang
Attorney, Agent, or Firm—Oppenheimer, Wolff & Donnelly, L.L.P.

[57] ABSTRACT

Methods and associated compositions are provided for the effective treatment of mammalian disease conditions associated with infection by pathogenic organisms through the identification of extracellular enzymes necessary for the growth or survival of the pathogenic organism and the subsequent interference with the functional activity of the identified extracellular enzyme to an extent sufficient to significantly inhibit the growth or survival of the pathogenic organism.

2 Claims, 24 Drawing Sheets

OTHER PUBLICATIONS

F. Emmrich et al., "A Recombinant 64 Kilodalton Protein . . . Mycobacterial Antigens," Apr. 1986, 163:1024–1029, *J.Exp.Med.*

A.S. Mustafa et al. "Characteristics of human T–cell clone . . . patients," 1986, 57:123–130, Sympos. on the Immunology of Leprosy, Lepr rev.Suppl. 2.

P.E.M. Fine, "The relationship between delayed type hypersensitivity . . . mycobacterial vaccines in man," 1986, 57:275–283, *Lepr.Rev.,* Suppl. 2.

W.J. Britton et al., "Immunoreactivity of a 70 kD Protein . . . Chromatography," Sep. 1986, 691–708, *J .Exp.Medicine.*

Ian M. Orme, "The Kinetics of Emergence and Loss . . . *Mycobacterium Tuberculosis,"* Jan. 1, 1987, 138:293–298, *The Journal of Immunology.*

R.F. Breiman & M.A.Horwitz, "Guinea Pigs Sublethally Infected . . . Challenge," Mar. 1987, 164:799–811, *J. Exp. Med.*

F.M. LaForce, "Immunizations, Immunoprophylasix . . . Infections," May 8, 1987, 257(18):2464–2470, *JAMA*.

A. Worsaae et al., "Allergenic and Blastogenic Reactivity . . . Guinea Pigs," Dec. 1987, 55(12):2922–2927, *Infection and Immunity.*

Roche, Paul W., et al. "T–Cell Determinants and Antibody Binding Sites on the Major Mycobacterial Secretory Protein MPB59 of *Mycobacterium bovis."* *Infection and Immunity* 62 (Dec. 1994) 5319–26.

Horwitz, Marcus A., et al. "Protective Immunity Against Tuberculosis Induced by Vaccination with Major Extracellular Proteins of *Mycobacterium tuberculosis."* *Proceedings of the National Academy Science* USA 92 (Feb. 1995) 1530–34.

Silver, Richard F., et al., "T–Cell Epitopes of the 39kD Alpha Antigen of *Mycobacterium tuberculosis* BCG: Potential for Use in Vaccines and Diagnosis." *Journal of Cellular Biochemistry—Molecular Mechanisms in Tuberculosis* from the Keystone Symposia on Molecular & Cellular Biology, Supplement 19B, 1995 (Feb. 5–Mar. 15, 1995) Abstract No. B3–336: 94.

Huygen, Kris, et al. "Immunogenicity of a Tuberculosis DNA Vaccine Containing Genes Encoding the Components of the Secreted Antigen 85 Complex." *Journal of Cellular Biochemistry—Molecular Mechanisms in Tuberculosis* from the Keystone Symposia on Lolecular & Cellular Biology, Supplement 19B, 1995 (Feb. 5–Mar. 15, 1995) Abstract No. B3–408.

Orme, Ian M., et al. "T Lymphocytes Mediating Protection and Cellular Cytolysis During the Course of *Mycobacterium tuberculosis* Infection." *The Journal of Immunology* 148 Jan. 1992) 189–96.

Young, D.B., et al. "Mycobacterial Protein Antigens: A Compilation." *Molecular Microbiology* 6, No. 2 (1992) 133–45.

Lee, Byong–Wha Esther, et al. "Cell–Mediated Immune Responses to the Native 71kD Protein of *Mycobacterium tuberculosis* in Guinea Pigs and Humans." From the Twenty–Seventh U.S.–Japan Leprosy Research Conference, Tuberculosis Research Conference, and Leprosy/Tuberculosis Symposium(Aug 4–7, 1992).

Horwitz, Marcus A., et al. "Progress in the Development of a Subunit Vaccine Against Tuberculosis." From the Twenty–Ninth U.S.–Japan Leprosy Research Conference, Tuberculosis Research Conference, and Leprosy/Tuberculosis Symposium (Aug. 19–22, 1994).

Bloch, Hubert, and William Segal. "Viability and Multiplication of Vaccines in Immunization Against Tuberculosis." *American Review of Tuberculosis* 7 (1955) 228–48.

Palmer, C., et al., "Experimental Studies of Vaccination, Allergy, and Immunity in Tuberculosis." *Bulletin of the World Health Organization* 12 (1955) 47–62.

Dubos, Re'ne J., et al. "Antituberculous Immunity Induced in Mice by Vaccination with Living Cultures of Attenuated Tubercle Bacilli." *Journal of Experimental Medicine* 97 (1953) 207–20.

Youmans, G.P. "Acquired Immunity in Tuberculosis." Chap. 8 in Tuberculosis. Edited by G.P. Youmans. Philadelphia: The W.B. Saunders Co. (1979).

Weiss, David W., and A.Q. Wells. "Immunization with Dead Tubercle Bacilli." *Tubercle* 37 (Apr. 1956) 137–40.

Meyer, Sven Nissen. "Animal Studies on Effects of BCG, H37Ra and *Mycobacterium phlei* in Tuberculosis Immunization." *Tubercle* 37 (Jan.–Feb. 1956) 11–22.

Wilson, G.S., and A.A. Miles, "Tuberculosis." Chap. 59 in *Topley and Wilson's Principles of Bacteriology and Immunity.* 4th ed. 2 vols. London: Edward Arnold (Publishers) Ltd. (1955).

Kubica, George P., and Lawrence G. Wayne, eds. *The Mycobacteria: A Sourcebook.* 2 parts. New York: Marcel Dekker, Inc. 33–57.

Infectious Diseases Society of America. *Reviews of Infectious Diseases* 11. Supplement 2. Chicago: The University of Chicago Press (Mar.–Apr. 1989).

Styblo, Karel. "Overview and Epidemiologic Assessment of the Current Global Tuberculosis Situtation with an Emphasis on Control in Developing Countries." S339–46.

Grosset, Jacques H. "Present Status of Chemotherapy for Tuberculosis." S347–52.

Fine, Paul E.M. "The BCG Story: Lessons from the Past and Implications for the Future." S353–9.

Pio, Antonio. "Impact of Present Control Methods on the Problem of Tuberculosis." S360–5.

Stead, William W. "Pathogenesis of Tuberculosis: Clinical and Epidemiologic Perspective." S366–8.

Dannenberg, Arthur M., Jr. "Immune Mechanisms in the Pathogenesis of Pulmonary Tuberculosis." S369–78.

Quinn, Thomas C. "Interactions of the Human Immunodeficiency Virus and Tuberculosis and the Implications for BCG Vaccination." S379–84.

Smith, Donald W., and Ernst H. Wiegeshaus. "What Animal Models Can TeachUs about the Pathogenesis of Tuberculosis in Humans." S385–93.

De Vries, Re'ne R.P. "Regulation of T Cell Responsiveness Against Mycobacterial Antigens by HLA Class 2 Immune Response Genes." S400–3.

Jacobs, William R., Jr., et al. "Mycobacteriophage Vector System." S404–10.

Patel, Rubina J., et al. A Cloned DNA Fragment for Identification of *Mycobacterium tuberculosis.* S411–9.

Brennan, Patrick J. "Structure of Mycobacteria: Recent Developments in Defining Cell Wall Carbohydrates and Proteins." S420–30.

Young, Douglas B., and Angela Mehlert. "Serology of Mycobacteria: Characterization of Antigens Recognized by Monoclonal Antibodies." S431–5.

Piessens, Willy F. "Introduction to the Immunology of Tuberculosis." S436–42.

Lamb, Jonathan R., et al. Identification of Mycobacterial Antigens Recognized by T Lymphocytes.S443–7.

Kaufman, Stefan H.E. "In Vitro Analysis of the Cellular Mechanisms Involved in Immunity to Tuberculosis." S448–54.

Ellner, Jerrold J. and Robert S. Wallis." Immunologic Aspects of Mycobacterial Infections." S455–9.

Bloom, Barry R. "New Approaches to Vaccine Development." S460–6.

Sensi, Piero. "Approaches to the Development of New Antituberculosis Drugs." S467–70.

Daniel, Thomas M. "Rapid Diagnosis of Tuberculosis: Laboratory Techniques Applicable in Developing Countries." S471–8.

Skamene, Emil. "Genetic Control of Susceptibility to Mycobacterial Infections." S394–9.

Parenti, Francesco. "New Experimental Drugs for the Treatment of Tuberculosis." S479–83.

Wiegeshaus, Ernst H., and Donald W. Smith. "Evaluation of the Protective Potency of New Tuberculosis Vaccines." S484–90.

Allison, A.C., and N.E. Byars. "An Adjuvant Formulation That Selectively Elicits the Formation of Antibodies of Protective Isotypes and of Cell–Mediated Immunity." *Journal of Immunology and Methodology* 95 (1986) 157–68.

Andersen, P., and I. Heron. "Specificity of a Protective Memory Immune Response against *Mycobacterium tuberculosis*." *Infection and Immunology* 61 (1993) 844–51.

Belisle, J.T., et al. "Identification of a Mycolyltransferase from *Mycobacterium tuberculosis* and the Coincident Definition of the Physiological Function of Antigen 85B." In Program of the 30th Joint Conference on Tuberculosis and Leprosy. U.S.–Japan Cooperative Medical Science Program. Ft. Collins, Colorado (Jul. 19–21, 1995) 212–6.

Chen, E.Y., and P.H. Seeburg. "Supercoil Sequencing: A Fast and Simple Method for Sequencing Plasmid DNA." *DNA* 4 (1985) 165–70.

Clemens, D.L., and Marcus A.Horwitz. "Characterization of the *Mycobacterium tuberculosis* Phagosome and Evidence That Phagosomal Maturation Is Inhibited." *Journal of Experimental Medicine* 181 (1955) 257–70.

Feller, D.C., and V.F. de la Cruz. "Identifying Antigenic T–Cells Sites." *Nature* 349 (1991) 720–1.

Grunstein, M., and D.S. Hogness. "Colony Hybridization: A Method for the Isolation of Cloned DNAs That Contain a Specific Gene." *Proceedings of the National Academy of Science* USA 72 (1975) 3961–6.

Harth, Günter, et al. "Glutamine Synthetase of *Mycobacterium tuberculosis*: Extracullular Release and Characterization of Its Enzymatic Activity." *Proceedings of the National Academy of Science* USA 91 (1994) 9342–6.

Hatfull, G.F., and G.J. Sarkis "DNA Sequence, Structure and Gene Expression of Mycobacteriophage L5: A Phage System for Mycobacterial Genetics." *Molecular Microbiology* 7 (1993) 395–405.

Huygen, Kris, et al. "Specific Lymphoproliferation, Gamma Interferon Production, and Serum Immunoglobulin G Directed Against a Purified 32kDa Mycobacterial Protein Antigen (P32) in Patients with Active Tuberculosis." *Scandinavian Journal of Immunology* 27 (1988) 187–94.

Kitaura, H., et al. "Cloning, Sequencing and Expression of the Gene for Alpha Antigen from *Mycobacterium intracellulare* and Use of PCR for the Rapid Identification of *Mycobacterium intracellulare*." *Biochemical and Biophysical Research Communications* 196 (1993) 1466–73.

Kremer, L., et al. "Analysis of the *Mycobacterium tuberculosis* 85A Antigen Promoter Region." *Journal of Bacteriology* 177 (1995) 642–53.

Kyte, J., and R. F. Doolittle. "Simple Method for Displaying the Hydropathy Character of a Protein." *Journal of Molecular Biology* 157 (1982) 105–32.

Launois, P., et al. "T–Cell–Epitope Mapping of the Major Secreted Mycobacterial Antigen Ag85A in Tuberculosis and Leprosy." *Infection and Immunity* 62 (1994) 3679–87.

Lee, Byong–Wha Esther, and Marcus A. Horwitz. "Identification of Macrophage and Stress–Induced Proteins of *Mycobacterium tuberculosis*." *Journal of Clinical Investigation* 96 (1995) 245–9.

Lee, T. D., and S. Vemuri. "MacProMass: A Computer Program to Correlate Mass Spectral Data to Peptide and Protein Structures." *Biomedical and Environmental Mass Spectroscopy* 19 (1990) 639–45.

Pribnow, D. "Nucleotide Sequence of an RNA Polymerase Binding Site at an Early T7 Promoter." *Proceedings of the National Academy of Science USA* 72 (1975) 784–8.

Sanger, F., et al. "DNA Sequencing with Chain–Terminating Inhibitors." *Proceedings of the National Academy of Science USA* 74 (1977) 5463–7.

Shine, J., and L. Dalgarno. "The 3'–Terminal Sequence of *Escherichia coli* 16S Ribosomal RNA: Complementarily to Nonsense Triplets and Ribosome Binding Sites." *Proceedings of the National Academy of Science USA* 71 (1974) 1342–6.

Shinnick, T. M. "The 65–Kilodalton Antigen of *Mycobacterium tuberculosis*." *Journal of Bacteriology* 169 (1987) 1080–8.

Yanisch–Perron, C., et al. "Improved M13 Phage Cloning Vectors and Host Strains: Nucleotide Sequences of the M13mp18 and pUC19 Vectors." *Genetics* 33 (1985) 103–19.

Von Heijne, G. "A New Method for Predicting Signal Sequence Cleavage Sites." *Nucleic Acids Research* 14 (1986) 4683–90.

Maugh, Thomas H., 2d. "Promising Tests Reported for New TB Vaccine." *Los Angeles Times*, Feb. 28, 1995, p. 1, col. 3.

Blander, Steven J., and Marcus A. Horwitz. "Vaccination with *Legionella pneumophila* Membranes Induces Cell–mediated and Protective Immunity in a Guinea Pig Model of Legionnaires' Disease." *Journal of Clinical Investigation* 87 (Mar. 1991 1054–9.

Horwitz, Marcus A. "Characterization of Avirulent Mutant *Legionella pneumophila* That Survive but Do Not Multiply within Human Monocytes." *Journal of Experimental Medicine* 166 (Nov. 1987) 1310–28.

Berdal, Bjorn P., et al. "Demonstration of Extracellular Chymotrypsin–Like Activity from Various Legionella Species." *Journal of Clinical Microbiology* 16 (Sep. 1982) 452–7.

Müller, Hans E. "Proteolytic Action of *Legionella pneumophila* on Human Serum Proteins." *Infection and Immunity* 27 (Jan. 1980) 51–3.

Horwitz, Marcus A., and Samuel C. Silverstein. "Legionnaires' Disease Bacterium (*Legionella pneumophila*) Multiplies Intracellularly in Human Monocytes." *Journal of Clinical Investigation* 66 (Sep. 1980) 441–50.

Horwitz, Marcus A. "Cell–mediated Immunity in Legionnaires' Disease." *Journal of Clinical Investigation* 71 (Jun. 1983) 1686–97.

Blander, Steven J., et al. "A Live Avirulent Mutant *Legionella pneumophila* Vaccine Induces Protective Immunity against Lethal Aerosol Challenge." *Journal of Clinical Investigation* 83 (Mar. 1989) 810–5.

Blander, Steven J., and Marcus A. Horwitz. "Major Cytoplasmic Membrane Protein of *Legionella pneumophila*, a Genus Common Antigen and Member of the hsp 60 Family of Heat Shock Proteins, Induces Protective Immunity in a Guinea Pig Model of Legionnaires' Disease." *Journal of Clinical Investigation* 91 (Feb. 1993) 717–23.

Blander, Steven J., and Marcus A. Horwitz. "Vaccination with the Major Secretory Protein of Legionella Induces Humoral and Cell–mediated Immune Responses and Protective Immunity across Different Serogroups of *Legionella pneumophila* and Different Species of Legionella." *Journal of Immunology* 147 (Jul. 1991) 285–91.

Blander, Steven J., et al. "An Immunoprotective Molecule, the Major Secretory Protein of *Legionella pneumophila*, Is Not a Virulence Factor in a Guinea Pig Model of Legionnaires' Disease." *Journal of Clinical Investigation* 86 (Sep. 1990) 817–24.

Nagai, Sadamu, et al. "Isolation and Partial Characterization of Major Protein Antigens in the Culture Fluid of *Mycobacterium tuberculosis*". *Infection and Immunity* Jan. 93; vol. 59, No. 1 pp. 372–382.

Bianchi, C. Paul. "Pharmacology" *Chemical Abstracts* vol. 100, No. 23; Jun. 4, 1984 and vol. 112, No. 19, May 7, 1990.

O'Hara, Naoya, et al. "Cloning and Sequencing of the Gene for a Antigen from *Mycobacterium avium* and Maping of B–Cell Epitopes". *Infection and Immunity*, Apr. 1993, pp. 1173–1179.

Oettinger, T. "Cloning and B–Cell–Epitope Mapping of MPT64 from *Mycobacterium tuberculosis* H37Rv." *Infection and Immunity*, May 1994, pp. 2058–2064.

Yamaguchi, Ryuji, et al. "Cloning and Characterization of the Gene for Immunogenic Protein MPB64 of *Mycobacterium bovis* BCG." *Infection and Immunity*, Jan. 1989, pp. 283–288.

Lee, Bai–Yu et al. "Characterization of the Major Membrane Protein of Virulent *Mycobacterium tuberculosis*." *Infection and Immunity;* May 1992, pp. 2066–2074.

Verbon, Annelies et al. "The 14,000–Molecular–Weight of *Mycobacterium tuberculosis* Is Related to the Alpha–Crystallin Family of Low–Molecular–Weight Heat Shock Proteins". *Journal of Bacteriology*, Feb. 1992, pp. 1352–1359.

Verbon, A. et al. "Characterization of B Cell Epitopes on the 16K Antigen of *Mycobacterium tuberculosis*". *Clin. exp. Immunology* (1992) 89, pp. 395–401.

Matsuo, Kazuhiro et al. "Cloning and Expression of the *Mycobacterium bovis* BCG Gene for Extracellular Alpha Antigen". *Journal of Bacteriology*, Sep. 1988, pp. 3847–3854.

P.E.M. Fine, "BCG Vaccination Against Tuberculosis and Leprosy". 1988, 44(3):691–703,*British Medical Bulletin*.

M.A. Horwitz. "Intracellular Parasitism". 1988, 1:41–46, *Current Opinion in Immunology*.

G.W. Comstock. "Identification of an Effective Vaccine Against Tuberculosis." 1988, 138:479–480,*Am Rev Respir Dis*.

C. Abou–Zeid et al. "The Secreted Antigens of *Mycobacterium tuberculosis* and Their Relationship to Those Recognized by the Available Antibodies". 1988, 134:531–538, *Journal of General Microbiology*.

A.J. Radford et al. "Cloning of a Species–Specific Antigen of *Mycobacterium bovis*," Apr. 1988, 56(4):921–925;*Infection and Immunity*.

F.M. Collins et al. "Biological Activity of Proteins Antigens Isolated from *Mycobacterium tuberculosis* Culture Filtrate," May 1988, 56(5):1260–1266,*Infection and Immunity*.

I.M. Orme. "Characteristics and Specificity of Acquired Immunologic Memory to *Mycobacterium tuberculosis* Infection". May 15, 1988, 140(10):3589–93;*Journal of Immunology*.

D. Young et al. "Stress Proteins are Immune Targets in Leprosy and Tuberculosis". Jun. 1988, 85:4267–4270;*Proc. Natl. Acad. Sci.*

M. Turner et al. "Humoral Immune Response in Human Tuberculosis: Immunoglobulins G, A, and M are Directed Against eh Purified P32 Protein Antigen of *Mycobacterium bovis* Bacillus Calmette–Guerin". Sep. 1988, 26:1714–1719, *Journal of Clinical Microbiology*.

H.S. Rumschlag et al. "Serological Responses of Patients with Lepromatous and Tuberculoid Leprosy to 30–,31–, and 32–Kilodalton Antigens of *Mycobacterium tuberculosis.*" Oct. 1988, 26 (1):2200–2202;*Journal of Clinical Microbiology*.

A.J. Crowle. "Immunization Against Tuberculosis: What Kind of Vaccine?" Nov. 1988, 56(11):2769–2773,*Infection and Immunity*.

I.M. Orme. "Induction of Nonspecific Acquired Resistance and Delayed–Type Hypersensitivity, but Not Specific Acquired Resistance, in Mince Inoculated with Killed Mycobacterial Vaccines." Dec. 1988, 56(12):3310–3312, *Infection and Immunity*.

M.E. Munk et al. "T Cell Responses of Normal Individuals towards Recombinant Protein Antigens of *Mycobacterium tuberculosis.*" 1988, 18:1835–1838,*Eur. Journal of Immunology*.

A. Rees et al. "Specificity of Proliferative Response of Human CD8 Clones to *Mycobacterium tuberculosis*". 1988, 18:1835–1838, *Eur. Journal of Immunology*.

V. Bhardwaj & M.J. Colston. "The Processing and Presentation of Mycobacterial Antigens by Human Monocytes". 1988, 18:691–696,*European Journal of Immunology*.

J.M. Grange. "Molecular Biology: New Hopes and Challenges". 1988, 69:1–4, *Tubercle*.

K.M. Citron. "Control and Prevention of Tuberculosis in Britain." 1988,44(3):704–716;*British Medical Bulletin*.

"Use of BCG Vaccines in the Control of Tuberculosis: A Joint Statement by the ACIP and the Advisory Committee for Elimination of Tuberculosis," Nov. 4, 1988, 37(43):663–675,*MMWR*.

C. Abou–zeid et al., "Characterization of Fibronectin–Binding Antigens Released by *Mycobacterium tuberculosis* and *Mycobacterium bovis* BCG," Dec. 1988, 56(12):3046–3051, *Infection and Immunity*.

R.J. Garsia et al., "Homology of the 70–Kilodalton Antigens from *Mycobacterium leprae* and *Mycobacterium tuberculosis* 71–Kilodalton Antigen with the Conserved Heat Shock Protein 70 of Eucaryotes," Jan. 1989, 57(1):204–212,*Infection and Immunity*.

A. Mehlert & D.B. Young, "Biochemical and Antigenic Characterization of the *Mycobacterium tuberculosis* 71kD Antigen, A Member of the 70kD Heat–Shock Protein Family," 1989, 3(2):125–130,*Molecular Microbiology*.

S.J. Blander & M.A. Horwitz, "Vaccination with the Major Secretory Protein of *Legionella Pneumophila* Induces Cell-Mediated and Protective Immunity In a Guinea Pig Model of Legionnaires' Disease," Mar. 1989, 169:691–705, *J.Exp.Med*.

W.S. Jordan, Jr., "Impediments to the Development of Additional Vaccines: Vaccines Against Important Diseases That Will Not Be Available in the Next Decade," May–Jun. 1989, II(Supp.3):S603–612,*Rev.Infec.Diseases*.

M. Borremans et al., "Cloning, Sequence Determination, and Expression of a 32–Kilodalton–Protein Gene of *Mycobacterium tuberculosis*," Oct. 1989, 57(10):3123–3130,*Infection and Immunity*.

E. Adams et al., "T cell reactivity to the Purified Mycobacterial Antigens p65 and p70 in Leprosy Patients and Their Household Contacts," 1990, 80:206–212, *Clin. exp. Immunol*.

H.G. Wiker et al., "Evidence for Three Separate Genes Encoding the Proteins fo the Mycobacterial Antigen 85 Complex," Jan. 1990, 58(1):272–274,*Infection and Immunity*.

L. De Wit, et al., "Nucleotide sequence of the 32 kDa–protein Gene (Antigen 85A) of *Mycobacterium bovis* BCG," 1990, 18(13):3995,*Nucleic Acids Research*.

H.G. Wiker et al., "Localization Index for Distinction Between Extracellular and intracellular Antigens of *Mycobacterium tuberculosis*," 1991, 137:875–884,*Journal of General Microbiology*.

D.V. Havlir et al., "Human Immune Response to *Mycobacterium tuberculosis* Antigens," Feb. 1991, 59(2):665–670, *Infection and Immunity*.

B.J. Luft et al., "Immunologic and Structural Characterization of the Dominant 66– to 73–kDa Antigens of *Borrelia burgdorferi*," Apr. 15, 1991, 146(8):2776–2782,*Journal of Immunology*.

P. Launois et al., "T cell Response To Purified Filtrate Antigen 85 from *Mycobacterium bovis* Bacilli Calmette–guerin (BCG) In Leprosy Patients," 1991, 86:286–290, *Clin. exp. Immunol*.

K.R. McKenzie et al., "Sequence and Immunogenicity of the 70–kDa Heat Shock Protein of *Mycobacterium leprae*," Jul. 1, 1991, 147(1):312–319,*Journal of Immunology*.

C. Abou–zeid et al., "Genetic and Immunological Analysis of *Mycobacterium tuberculosis* Fibronectin–Binding Proteins," Aug. 1991, 59(8):2712–2718,*Infection and Immunity*.

L. de Menconca Lima, "Nucleotide Sequence of the Gene Coding for the 85–B Antigen of *Mycobacterium leprae*," 1991, 19(20):5789,*Nucleic Acids Research*.

J. Content et al., "The Genes Coding for the Antigen 85 Complexes of *Mycobacterium tuberculosis* and *Mycobacterium bovis* BCG Are Members of a Gene Family: Cloning, Sequence Determination, and Genomic Organization of the Gene Coding for Antigen 85–C of *M. tuberculosis*," Sep. 1991, 59(9):3205–3212,*Infection and Immunity*.

J.E.R. Thole et al., "Molecular and Immunological Analysis of a Fibronectin–binding Protein Antigen secreted by *Mycobacterium leprae*," 1992, 6(2):153–163,*Molecular Microbiology*.

H.P. Godfrey et al., "Modulation of Expression of Delayed Hypersensitivity by Mycobacterial Antigen 85 Fibronectin–Binding Proteins," Jun. 1992, 60(6):2522–2528,*Infection and Immunity*.

M.C.V. Pessolani & P.J. Brennan, "*Mycobacterium leprae* Produces Extracellular Homologs of the Antigen 85 Complex," Nov. 1992, 60(11):4452–4459,*Infection and Immunity*.

A. Rambukkana et al., "Identification and Characterization of Epitopes Shared Between the Mycobacterial 65–Kilodalton heat Shock Protein and the Actively Secreted Antigen 85 Complex Their In Situ Expression on the Cell Wall Surface of *Mycobacterium leprae*," Nov. 1992, 60(11):4517–4527, *Infection and Immunity*.

P.G. Pal & M.A. Horwitz, "Immunization with Extracellular Proteins of *Mycobacterium tuberculosis* Induces Cell–Mediated Immune Responses and Substantially Protective Immunity In a Guinea Pig Model of Pulmonary Tuberculosis," Nov. 1992, 60(11):4781–4792,*Infection and Immunity*.

A. Rambukkana et al., "Heterogeneity of Monoclonal Antibody–Reactive Epitopes on Mycobacterial 30–Kilodalton–Region Proteins and the Secreted Antigen 85 Complex and the Demonstration of Antigen 85B on the *Mycobacterium leprae* Cell Wall Surface," Dec.1992, 60(12):5172–5181, *Infection and Immunity*.

H.G. Wiker & M. Harboe, "The Antigen 85 Complex: a Major Secretion Product of *Mycobacterium tuberculosis*," Dec. 1992, 56(4):648–661,*Microbiological Reviews*.

A. Drowart et al., "Isoelectrophoretic Characterization of Protein Antigens Present in Mycobacterial Culture Filtrates and Recognized by Monoclonal Antibodies Directed Against the *Mycobacterium bovis* BCG Antigen 85 Complex," 1992, 36:697–702, *Scand. J. Immunol*.

S.H.E. Kaufmann & D.B. Young, "Vaccination against Tuberculosis and Leprosy," 1992, 184:208–229,*Immunobiol*.

P. Launois et al., "IL–6 Production in Response to Purified Mycobacterial Heat–Shock Proteins and to Antigen 85 in Leprosy," 1993, 148:283–290, *Cellular Immunology*.

A. Rambukkana et al., "The Mycobacterial Secreted Antigen 85 Complex Possesses Epitopes That Are Differentially Expressed in Human Leprosy Lesions and *Mycobacterium leprae*–Infected Armadillo Tissues," May 1993, 61(5):1835–1845,*Infection and Immunity*.

T.F. Rinke de Wit, "The *Mycobacterium leprae* Antigen 85 Complex Gene Family: Identification of the Genes for the 85A, 85C and Related MPT51 Proteins," Sep. 1993, 61(9):3642–3647,*Infection and Immunity*.

P. Peake et al., "Mechanism of Interaction of the 85B Secreted Protein of *Mycobacterium bovis* with Fibronectin," Nov. 1993, 61(11):4828–4834,*Infection and Immunity*.

M.A. Horwitz, "The Immunobiology of *Legionella Pneumophila*," Chapter 11, 1989, 141–156,*Intracellular Parasitism*.

Weiss, David. "Vaccination Against tuberculosis with Nonliving Vaccines". *American Review of Respiratory Diseases*, 1959, pp. 340–358.

DeWit, Luk et al. "Nucleotide Sequence of the 85B–Protein Gene of *Mycobacterium bovis* BCG and *Mycobacterium tuberculosis*." *DNA Sequence—The Journal of DNA Sequencing and Mapping*, vol. 4, pp. 267–270.

Horwitz, M.A., et al. "Progress in the Development of a Subunit Vaccine Against Tuberculosis and a New Nonhuman Primate Model of Pulmonary Tuberculosis". Seminar on Molecular Mechanisms in Tuberculosis; Feb. 19–25, 1995; Tamarron, Colorado.

Zhang, Y., et al. Genetic Analysis of superoxide dismutase, the 23 kilodalton antigen of *Mycobacterium tuberculosis*, *Molecular Microbiology*, (1991) 5(2), pp. 381–391.

Wurth, Becky. Novagen, Inc. Facsimile Transmission; Dec. 20, 1996.

| PURIFIED EXTRACELLULAR PROTEINS STUDIED | |
|---|---|
| APPARENT MW. BY SDS-PAGE (KD) | N TERMINAL 5 AMINO ACIDS |
| 110 | 1 NSKSV |
| 80 | 2 TDRVS |
| 71 | 3 ARAVG |
| 58 | 4 TEKTP |
| 45 | 5 DPEPA |
| 32A | 6 FSRPG |
| 32B | 7 FSRPG |
| 30 | 8 FSRPG |
| 24 | 9 APYEN |
| 23.5 | 10 APKTY |
| 23 | 11 AETYL |
| 16 | 12 AYPIT |
| 14 | 13 ADPRL |
| 12 | 14 FDTRL |

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
           (A) ORGANISM: Mycobacterium tuberculosis
           (B) STRAIN: Erdman (xi) SEQUENCE DESCRIPTION: SEQ ID NO:1:

Asn Ser Lys Ser Val
1               5

(2) INFORMATION FOR SEQ ID NO:2:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
           (A) ORGANISM: Mycobacterium tuberculosis
           (B) STRAIN: Erdman (xi) SEQUENCE DESCRIPTION: SEQ ID NO:2:

Thr Asp Arg Val Ser
1               5

(2) INFORMATION FOR SEQ ID NO:3:

(i) SEQUENCE CHARACTERISTICS:
           (A) LENGTH: 5 amino acids
           (B) TYPE: amino acid
           (C) STRANDEDNESS: Not Relevant
           (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
           (A) ORGANISM: Mycobacterium tuberculosis
           (B) STRAIN: Erdman -continued

```
    (xi) SEQUENCE DESCRIPTION: SEQ ID NO:3:

Ala Arg Ala Val Gly
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:4:

Thr Glu Lys Thr Pro
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:5:

Asp Pro Glu Pro Ala
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:6:
```

```
Phe Ser Arg Pro Gly
1               5

(2) INFORMATION FOR SEQ ID NO:7:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
         (A) ORGANISM: Mycobacterium tuberculosis
         (B) STRAIN: Erdman (xi) SEQUENCE DESCRIPTION: SEQ ID NO:7:

Phe Ser Arg Pro Gly
1               5

(2) INFORMATION FOR SEQ ID NO:8:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
         (A) ORGANISM: Mycobacterium tuberculosis
         (B) STRAIN: Erdman (xi) SEQUENCE DESCRIPTION: SEQ ID NO:8:

Phe Ser Arg Pro Gly
1               5

(2) INFORMATION FOR SEQ ID NO:9:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
         (A) ORGANISM: Mycobacterium tuberculosis
         (B) STRAIN: Erdman (xi) SEQUENCE DESCRIPTION: SEQ ID NO:9:

Ala Pro Tyr Glu Asn
1               5
```

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:10:

Ala Pro Lys Thr Tyr
1               5

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:11:

Ala Glu Thr Tyr Leu
1               5

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:12:

Ala Tyr Pro Ile Thr
1               5

-continued (2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:13:

```
Ala Asp Pro Arg Leu
1               5
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Mycobacterium tuberculosis
        (B) STRAIN: Erdman (xi) SEQUENCE DESCRIPTION: SEQ ID NO:14:

```
Phe Asp Thr Arg Leu
1               5
```

(2) INFORMATION FOR SEQ ID NO:15:

(i) SEQUENCE CHARACTERISTICS:
        (A) LENGTH: 1437 base pairs
        (B) TYPE: nucleic acid
        (C) STRANDEDNESS: single
        (D) TOPOLOGY: Not Relevant (ii) MOLECULE TYPE: DNA (genomic)

(xi) SEQUENCE DESCRIPTION: SEQ ID NO:15:

```
GTGACGGAAA AGACGCCCGA CGACGTCTTC AAACTTGCCA AGGACGAGAA GGTCGAATAT     60

GTCGACGTCC GGTTCTGTGA CCTGCCTGGC ATCATGCAGC ACTTCACGAT TCCGGCTTCG    120

GCCTTTGACA AGAGCGTGTT TGACGACGGC TTGGCCTTTG ACGGCTCGTC GATTCGCGGG    180

TTCCAGTCGA TCCACGAATC CGACATGTTG CTTCTTCCCG ATCCCGAGAC GGCGCGCATC    240

GACCCC GCGCGGCCAA GACGCTGAAT ATCAACTTCT TTGTGCACGA CCCGTTCACC        300

CTGGAGCCGT ACTCCCGCGA CCCGCGCAAC ATCGCCCGCA AGGCCGAGAA CTACCTGATC    360

AGCACTGGCA TCGCCGACAC CGCATACTTC GGCGCCGAGG CCGAGTTCTA CATTTTCGAT    420

TCGGTGAGCT TCGACTCGCG CGCCAACGGC TCCTTCTACG AGGTGGACGC CATCTCGGGG    480
```

```
TGGTGGAACA CCGGCGCGGC GACCGAGGCC GACGGCAGTC CCAACCGGGG CTACAAGGTC    540

CGCCACAAGG GCGGGTATTT CCCAGTGGCC CCCAACGACC AATACGTCGA CCTGCGCGAC    600

AAGATGCTGA CCAACCTGAT CAACTCCGGC TTCATCCTGG AGAAGGGCCA CCACGAGGTG    660

GGCAGCGGCG GACAGGCCGA GATCAACTAC CAGTTCAATT CGCTGCTGCA CGCCGCCGAC    720

GACATGCAGT TGTACAAGTA CATCATCAAG AACACCGCCT GGCAGAACGG CAAAACGGTC    780

ACGTTCATGC CCAAGCCGCT GTTCGGCGAC AACGGGTCCG GCATGCACTG TCATCAGTCG    840

CTGTGGAAGG ACGGGCCCC GCTGATGTAC GACGAGACGG GTTATGCCGG TCTGTCGGAC    900

ACGGCCCGTC ATTACATCGG CGGCCTGTTA CACCACGCGC CGTCGCTGCT GGCCTTCACC    960

AACCCGACGG TGAACTCCTA CAAGCGGCTG GTTCCCGGTT ACGAGGCCCC GATCAACCTG   1020

GTCTATAGCC AGCGCAACCG GTCGGCATGC GTGCGCATCC CGATCACCGG CAGCAACCCG   1080

AAGGCCAAGC GGCTGGAGTT CCGAAGCCCC GACTCGTCGG GCAACCCGTA TCTGGCGTTC   1140

TCGGCCATGC TGATGGCAGG CCTGGACGGT ATCAAGAACA AGATCGAGCC GCAGGCGCCC   1200

GTCGACAAGG ATCTCTACGA GCTGCCGCCG GAAGAGGCCG CGAGTATCCC GCAGACTCCG   1260

ACCCAGCTGT CAGATGTGAT CGACCGTCTC GAGGCCGACC ACGAATACCT CACCGAAGGA   1320

GGGGTGTTCA CAAACGACCT GATCGAGACG TGGATCAGTT TCAAGCGCGA AAACGAGATC   1380

GAGCCGGTCA ACATCCGGCC GCATCCCTAC GAATTCGCGC TGTACTACGA CGTTTAA     1437

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
         (A) ORGANISM: Mycobacterium tuberculosis
         (B) STRAIN: Erdman (xi) SEQUENCE DESCRIPTION: SEQ ID NO:16:

Thr Glu Lys Thr Pro Asp Asp
1               5

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
         (A) ORGANISM: Mycobacterium tuberculosis
         (B) STRAIN: Erdman (xi) SEQUENCE DESCRIPTION: SEQ ID NO:17:
```

Ala Glu Lys Thr Ser Asp Asp
1               5

(2) INFORMATION FOR SEQ ID NO:18:

(i) SEQUENCE CHARACTERISTICS:
        (A) LENGTH: 2985 base pairs
        (B) TYPE: nucleic acid
        (C) STRANDEDNESS: single
        (D) TOPOLOGY: Not Relevant (ii) MOLECULE TYPE: DNA (genomic)

(xi) SEQUENCE DESCRIPTION: SEQ ID NO:18:

```
GTGGTCGTGA CCAAACTCGC CACGCAGCGG CCGAAGTTGC CCAGCGTTGG CCGGCTCGGA        60

TTAGTTGACC CCCCTGCTGG TGAGCGTCTG GCTCAGGTGG GGTGGGATCG GCACGAGGAT       120

CAGGCGCACG TCGACCTGCT GTGGTCGCTG TCACGCGCTC CGGACGCCGA TGCCGCGCTG       180

CGCGCCTTGA TCCGGCTGTC GGAGAATCCA GACACCGGAT GGGACGAGCT CAACGCGGCT       240

CTGCCG AACGCAGTCT GCGCGGGCGG CTGTTCTCGG TGCTGGGCTC GTCGCTGGCG     300

TTGGGCGATC ACCTGGTCGC CCATCCGCAG TCCTGGAAAT TGCTGCGGGG CAAGGTCACA       360

CTGCCGTCCC ATGACCAGCT GCAGCGGTCG TTCGTCGAGT GCGTCGAGGA ATCGGAGGGT       420

ATGCCGGGCT CGCTCGTGCA CCGATTGCGA ACCCAGTACC GCGACTACGT GCTAATGCTG       480

GCCGCTCTCG ACCTGGCCGC GACGGTCGAG GACGAACCGG TGCTGCCATT CACCGTGGTG       540

GCCGCACGCC TGGCGGACGC CGCGGACGCC GCTCTGGCGG CGGCGCTGCG CGTGGCCGAG       600

GCGAGCGTGT GCGGCGAGCA CCCGCCACCG CGCCTGGCGG TCATCGCGAT GGGCAAGTGC       660

GGTGCGCGCG AACTGAACTA CGTCAGCGAC GTCGATGTCA TATTCGTTGC CGAGCGCTCC       720

GACCCGCGCA ACGCGCGCGT GGCCAGCGAG ATGATGCGGG TGGCCTCGGC GGCCTTTTTC       780

GAGGTGGACG CCGCCCTGCG TCCGGAGGGG CGCAACGGGG AGCTGGTCCG TACGCTCGAG       840

TCGCACATCG CCTACTACCA GCGCTGGGCC AAGACCTGGG AGTTTCAGGC GTTGCTGAAA       900

GCACGGCCAG TCGTTGGCGA CGCGGAACTT GGCGAGCGTT ACCTGACCGC CTTGATGCCG       960

ATGGTGTGGC GAGCCTGCGA GCGCGAAGAC TTTGTGGTCG AGGTGCAGGC CATGCGGCGG      1020

CGGGTGGAGC AGCTGGTGCC CGCCGATGTC CGCGGCCGCG AGCTCAAACT CGGCAGCGGC      1080

GGATTGCGCG ACGTGGAGTT CGCCGTACAG CTACTGCAGC TGGTTCATGC CCGTAGCGAC      1140

GAGTCGTTAC GGGTGGCGTC CACGGTGGAC GCATTGGCGG CGTTGGGCGA AGGCGGCTAC      1200

ATCGGGCGTG AGGACGCGGC GAACATGACC GCGTCGTATG AGTTCCTCAG GCTGCTCGAG      1260

CACCGACTGC AGTTGCAGCG GCTCAAGCGC ACCCACCTGC TTCCCGATCC CGAAGACGAG      1320

GAGGCAGTGC GCTGGCTGGC GCGCGCGGCC CACATCCGGC CCGATGGCCG AAACGATGCG      1380

GCCGGGGTGC TGCGGGAGGA ACTCAAGAAG CAGAACGTGC GGGTGTCGAA GTTACACACC      1440

AAACTCTTCT ATCAACCGCT GCTGGAATCG ATCGGCCCGA CCGGGTTGGA GATCGCCCAC      1500

GGCATGACGT TGGAGGCCGC GGGGCGCCGG CTGGCCGCGC TGGGCTACGA GGGACCGCAG      1560

ACCGCGTTGA ACACATGTC GGCGTTGGTC AATCAAAGCG GCCGGCGCGG ACGGGTGCAG      1620

TCGGTGCTGC TGCCCAGGCT GCTGGACTGG ATGTCGTATG CCCCCGATCC CGACGGCGGA      1680

CTGCTGGCCT ACCGGCGGCT CAGTGAGGCG CTGGCCACCG AAAGCTGGTA CCTGGCCACG      1740

CTGCGGGACA AGCCCGCGGT GGCCAAGCGG CTCATGCATG TCTTGGGTAC CTCGGCGTAT      1800

GTGCCGGATC TGTTGATGCG CGCGCCGCGG GTCATCCAGC AGTACGAGGA CGGGCCTGCG      1860

GGCCCGAAGC TGCTCGAGAC CGAGCCCGCC GCCGTGGCTC GGGCGCTGAT CGCCTCGGCG      1920
```

```
AGCCGCTACC CCGACCCGGA GCGGGCCATC GCCGGCGCGC GCACGCTGCG TCGTCGAGAG      1980

CTGGCCCGCA TCGGTTCGGC GGACCTGCTC GGCCTGCTCG AGGTCACCGA GGTGTGCCGG      2040

GCGTTGACGT CGGTGTGGGT GGCGGTGCTG CAGGCCGCGC TGGACGTCAT GATCCGGGCC      2100

AGCCTTCCCG ACGACGATCG CGCCCCGGCG GCCATCGCGG TCATCGGCAT GGGTCGGCTG      2160

GGTGGTGCCG AGTTGGGCTA CGGGTCGGAT GCCGACGTGA TCTTCGTCTG TGAGCCGGCC      2220

ACCGGCGTCG ACGATGCACG GGCGGTGAAA TGGTCGACAT CGATCGCCGA GCGGGTTCGG      2280

GCGCTGCTGG GGACACCCAG CGTCGATCCG CCGCTGGAGC TCGACGCCAA TTTGCGACCC      2340

GAGGGCCGCA ACGGTCCGCT GGTCCGCACC CTGGGGTCCT ACGCCGCATA CTACGAGCAG      2400

TGGGCACAGC CATGGGAGAT CCAGGCCCTG CTACGCGCAC ACGCGGTTGC CGGCGATGCC      2460

GAGTTGGGTC AGCGATTCCT ACGGATGGTC GACAAAACGC GGTATCCGCC CGACGGTGTG      2520

TCCGCTGACT CGGTGCGCGA GATTCGCCGC ATCAAGGCCC GTATCGAGTC CGAGCGGTTG      2580

CCGCGCGGTG CCGACCCCAA CACACACACC AAACTGGGCC GCGGCGGACT GGCCGACATC      2640

GAATGGACCG TGCAGTTGCT GCAGCTACAG CATGCGCACC AGGTTCCCGC CCTGCACAAC      2700

ACCTCGACGC TGCAATCCCT GGATGTCATC GCGGCCGCCG ATCTGGTTCC CGCAGCCGAC      2760

GTGGAGCTGC TCCGTCAGGC CTGGCTGACC GCCACCCGGG CCCGCAACGC GCTGGTGTTG      2820

GTGCGCGGCA AGCCCACCGA CCAGCTGCCG GGACCCGGGC GCCAGCTCAA TGCGGTCGCG      2880

GTCGCGGCCG GCTGGCGAAA CGACGACGGT GGGGAATTCC TGGACAACTA CCTACGGGTG      2940

ACGCGGCGGG CAAAGGCGGT AGTGCGCAAA GTGTTCGGGA GTTGA                     2985

(2) INFORMATION FOR SEQ ID NO:19:

(i) SEQUENCE CHARACTERISTICS:
          (A) LENGTH: 1341 base pairs
          (B) TYPE: nucleic acid
          (C) STRANDEDNESS: single
          (D) TOPOLOGY: Not Relevant (ii) MOLECULE TYPE: DNA (genomic)

(xi) SEQUENCE DESCRIPTION: SEQ ID NO:19:

ATGGACCGAC AGGAGGAATT CGTTCTTCGT ACCCTGGAAG AACGCGACAT CCGCTTCGTC        60

CGGCTGTGGT TCACAGACGT GCTCGGTTTC CTGAAGTCGG TCGCCATCGC CCCAGCCGAA       120

CTCGAGGGCG CCTTCGAGGA AGGCATCGGC TTCGACGGAT CCTCGATCGA GGGCTTTGCG       180

CGGGTCTCGG AATCCGATAC GGTGGCGCAC CCGGACCCGT CGACCTTCCA GGTGCTGCCC       240

TGGGCCACCA GTTCCGGCCA CCACCACTCA GCGCGGATGT TTTGCGACAT CACCATGCCG       300

GACGGCTCGC CGTCGTGGGC GGACCCGCGG CACGTGTTGC GGCGGCAGCT GACGAAGGCC       360

GGCGAACTCG GCTTCTCCTG CTACGTGCAT CCCGAAATCG AGTTCTTCCT GCTCAAGCCC       420

GGACCCGAGG ACGGGTCGGT GCCCGTCCCG GTCGACAACG CCGGCTATTT CGACCAAGCG       480

GTGCACGACT CCGCCTTGAA CTTTCGCCGC CACGCGATCG ATGCCCTGGA ATTCATGGGC       540

ATCTCGGTGG AGTTCAGCCA TCACGAAGGC GCACCCGGCC AGCAGGAGAT CGACCTGCGG       600

TTTGCCGACG CTCTGTCGAT GGCTGACAAC GTGATGACCT TCCGCTACGT CATCAAAGAA       660

GTCGCGCTGG AAGAGGGCGC CCGGGCGTCG TTCATGCCCA AGCCATTCGG CCAGCACCCG       720

GGCTCGGCGA TGCACACCCA CATGAGCCTG TTCGAGGGTG ATGTCAACGC GTTCCACAGC       780

GCTGATGATC CGCTGCAGCT GTCGGAAGTG GGTAAATCGT TCATCGCCGG GATCCTGGAG       840

CACGCTTGCG AGATCAGCGC GGTCACAAAT GACTGGGTCA ACTCTTACAA GCGGCTGGTG       900
```

```
CAGGGCGGCG AAGCGCCCAC GGCCGCGTCG TGGGGGGCCG CCAACCGATC CGCCCTAGTG      960

CGGGTGCCGA TGTACACGCC GCACAAGACC TCGTCGCGGC GGGTCGAAGT ACGCAGCCCT     1020

GATTCGGCGT GCAATCCCTA TCTGACATTC GCCGTGCTGC TGGCCGCGGG ATTGCGGGGT     1080

GTAGAGAAGG GTTACGTGCT GGGCCCGCAG GCCGAGGACA ACGTATGGGA CCTCACACCC     1140

GAGGAACGCC GAGCGATGGG GTACCGAGAA TTGCCGTCCA GTTTGGATAG TGCGCTGCGC     1200

GCCATGGAGG CCTCCGAACT CGTCGCGGAG GCCTTGGGGG AGCACGTTTT TGACTTTTTC     1260

TTGCGCAACA AGCGCACGGA GTGGGCGAAC TACCGCAGCC ACGTCACGCC ATACGAGCTG     1320

CGCACCTACC TGTCGCTGTA G                                               1341
```

(2) INFORMATION FOR SEQ ID NO:20:

(i) SEQUENCE CHARACTERISTICS:
        (A) LENGTH: 45 base pairs
        (B) TYPE: nucleic acid
        (C) STRANDEDNESS: single
        (D) TOPOLOGY: Not Relevant (ii) MOLECULE TYPE: DNA (genomic)

(xi) SEQUENCE DESCRIPTION: SEQ ID NO:20:

```
GGCGACAACG GGTCCGGCAT GCACTGTCAT CAGTCGCTGT GGAAG                       45
```

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: Not Relevant (ii) MOLECULE TYPE: DNA (genomic)

(xi) SEQUENCE DESCRIPTION: SEQ ID NO:21:

```
CCGCTCTTGC CCAGGCCGTA CGTGACAGTA GTCAGCGACA CCTTC                       45
```

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: Not Relevant (ii) MOLECULE TYPE: DNA (genomic)

(xi) SEQUENCE DESCRIPTION: SEQ ID NO:22:

```
AACTGGAATG GTGCAGGCTG CCATACCAAC TTCAGCACCA AGGCC                       45
```

(2) INFORMATION FOR SEQ ID NO:23:

(i) SEQUENCE CHARACTERISTICS:
        (A) LENGTH: 45 base pairs
        (B) TYPE: nucleic acid
        (C) STRANDEDNESS: single
        (D) TOPOLOGY: Not Relevant (ii) MOLECULE TYPE: DNA (genomic)

(xi) SEQUENCE DESCRIPTION: SEQ ID NO:23:

```
TTGACCTTAC CACGTCCGAC GGTATGGTTG AAGTCGTGGT TCCGG                       45
```

(2) INFORMATION FOR SEQ ID NO:24:

(i) SEQUENCE CHARACTERISTICS:

```
            (A) LENGTH: 21 base pairs
            (B) TYPE: nucleic acid
            (C) STRANDEDNESS: single
            (D) TOPOLOGY: Not Relevant (ii) MOLECULE TYPE: DNA (genomic)

(xi) SEQUENCE DESCRIPTION: SEQ ID NO:24:

GGCATGCACT GTCATCAGTC G                                          21

(2) INFORMATION FOR SEQ ID NO:25:

(i) SEQUENCE CHARACTERISTICS:
            (A) LENGTH: 21 base pairs
            (B) TYPE: nucleic acid
            (C) STRANDEDNESS: single
            (D) TOPOLOGY: Not Relevant (ii) MOLECULE TYPE: DNA (genomic)

(xi) SEQUENCE DESCRIPTION: SEQ ID NO:25:

CCGTACGTGA CAGTAGTCAG C                                          21
```

EXTERNALLY TARGETED PROPHYLACTIC AND CHEMOTHERAPEUTIC METHOD AND AGENTS

REFERENCE TO GOVERNMENT

This invention was made with Government support under Grant No. AI-35275 awarded by the Department of Health and Human Services. The Government has certain rights in this invention.

FIELD OF THE INVENTION

The present invention generally relates to novel prophylactic and chemotherapeutic methods and agents against pathogenic organisms such as bacteria, protozoa, viruses and fungi. More specifically, this invention relates to such methods and agents which are effective in fighting infection by pathogenic intracellular organisms through the novel mechanism of inhibiting or blocking the function of one or more extracellular enzymes necessary for the growth or survival of the pathogenic organism without harming the infected host. This invention particularly relates to such methods and agents which are effective in inhibiting growth of intracellular bacteria and even more specifically, pathogenic bacteria of the genus mycobacterium. In another more particular aspect, this invention relates to methods and associated antibiotics which are effective against diseases caused by drug-resistant strains of intracellular pathogens present in mammalian hosts.

BACKGROUND OF THE INVENTION

It has long been recognized that parasitic microorganisms possess the ability to infect animals thereby causing disease and often the death of the host. Pathogenic agents have been a leading cause of death throughout out history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic vectors is evidenced by the resurgence of various diseases such as tuberculosis, as well as the appearance of numerous drug resistant strains of bacteria and viruses.

Among those pathogenic agents of major epidemiological concern, intracellular organisms have proven to be particularly intractable in the face of therapeutic or prophylactic measures. Intracellular organisms, including bacteria of the genus Mycobacterium and the genus Legionella, complete all or part of their life cycle within the cells of the infected host organism rather than extracellularly. Around the world, intracellular bacteria are responsible for millions of deaths each year and untold suffering. Tuberculosis, caused by *Mycobacterium tuberculosis*, is the leading cause of death from infectious disease worldwide, with 10 million new cases and 2.9 million deaths every year. In addition, intracellular bacteria are responsible for millions of cases of leprosy. Other debilitating diseases transmitted by intracellular agents include cutaneous and visceral leishmaniasis, American trypanosomiasis (Chagas' disease), listeriosis, toxoplasmosis, histoplasmosis, trachoma, psittacosis, Q-fever, and legionellosis including Legionnaires' disease. At this time, treatment and prevention of these diseases is suboptimal. In many cases, relatively little can be done to prevent debilitating infections in susceptible individuals exposed to these organisms.

Due to this inability to effectively protect population from tuberculosis and the inherent human morbidity and mortality caused by tuberculosis, this is one of the most important diseases confronting mankind. More specifically, human pulmonary tuberculosis primarily caused by *M. tuberculosis* is a major cause of death in developing countries. By concealing itself within the cells primarily responsible for the detection of foreign elements and subsequent activation of the immune system, *M. tuberculosis* is relatively successful in evading the normal defenses of the host organism. As a result, by surviving inside macrophages and monocytes, *M. tuberculosis* may produce a chronic intracellular infection. These same pathogenic characteristics have heretofore prevented the development of effective prophylaxis or chemotherapeutic methods and agents against tubercular infections.

Those skilled in the art will appreciate that the discussion of *M. tuberculosis* is in no way intended to limit the scope of the present invention to the treatment of tubercular infections. On the contrary, this invention may be used to advantageously provide safe and effective prophylactic and chemotherapeutic methods and agents against any susceptible disease caused by intracellular pathogenic agents.

Currently it is believed that approximately one third of the world's population is infected by *M. tuberculosis* resulting in millions of cases of pulmonary tuberculosis annually. While this disease is a particularly acute health problem in the developing countries of Latin America, Africa, and Asia, it is also becoming more prevalent in the first world. In the United States specific populations are at increased risk, especially urban poor, immunocompromised individuals and immigrants from areas of high disease prevalence. Largely due to the AIDS epidemic the incidence of tuberculosis is presently increasing in developed countries, often in the form of multi-drug resistant *M. tuberculosis*.

Recently, tuberculosis resistance to one or more drugs was reported in 36 of the 50 United States. In New York City, one-third of all cases tested in 1991 were resistant to one or more major drugs. Though non-resistant tuberculosis can be cured with a long course of antibiotics, the outlook regarding drug resistant strains is bleak. Patients infected with strains resistant to two or more major antibiotics have a fatality rate of around 50%. Accordingly, a safe and effective treatment against such varieties of *M. tuberculosis* is sorely needed.

Initial infections of *M. tuberculosis* almost always occur through the inhalation of aerosolized particles, since the pathogen can remain viable for weeks or months in moist or dry sputum. Although the primary site of the infection is in the lungs, the organism can also cause infection of the bones, spleen, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic. However, approximately 10% of such individuals may reactivate the disease at some time in their lifetime, often many years after the initial infection. Reactivation disease can be debilitating, fatal, and contagious.

When *M. tuberculosis* is not controlled by the infected subject, it often results in the extensive degradation of lung tissue. In susceptible individuals lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney, and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation.

While *M. tuberculosis* is a significant pathogen, other species of the genus Mycobacterium also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. *M. avium* can cause serious infection in immunocompromised people including patients with AIDS. Another important pathogenic vector of the genus Mycobacterium is *M. leprae* which causes millions of cases of the ancient disease, leprosy. Other species of this genus which cause disease in animals and man include *M. kansasii, M. fortuitum, M. marinum, M. chelonei, M. africanum, M. ulcerans, M. microti* and *M. scrofulaceum*. The pathogenic mycobacterial species frequently exhibit a high degree of homology in their respective DNA and corresponding protein and enzyme sequences and some species, such as *M. tuberculosis* and *M. bovis*, are highly related.

Any animal or human infected with a pathogen and, in particular, an intracellular organism, presents a difficult challenge to the host immune system. While many infectious agents may be effectively controlled by the humoral response and corresponding production of protective antibodies, these mechanisms are primarily effective only against those pathogens located in the body's extracellular fluid. In particular, opsonizing antibodies bind to extracellular foreign agents thereby rendering them susceptible to phagocytosis and subsequent intracellular killing. Yet this is not the case for other pathogens. For example, previous studies have indicated that the humoral immune response does not appear to play a significant protective role against infections by intracellular bacteria such as *M. tuberculosis*.

Antibody mediated defenses seemingly do not prevent the initial infection of such intracellular pathogens and are ineffectual once the bacteria are sequestered within the cells of the host. As water soluble proteins, antibodies can permeate the extracellular fluid and blood, but have difficulty migrating across the lipid membranes of cells to the sequestered intracellular bacteria. Further, the production of opsonizing antibodies against bacterial surface structures may actually assist intracellular pathogens in entering the host cell.

Unlike most infectious bacteria, mycobacteria, including *M. tuberculosis*, tend to proliferate in vacuoles which are substantially sealed off from the rest of the infected cell by a membrane. Phagocytes naturally form these protective vacuoles making them particularly susceptible to infection by this class of pathogen.

The problems intracellular pathogens pose for the infected host's immune system also constitute a special challenge to the medical communities' development of effective prophylactic and chemotherapeutic regimes. At the present time there are few effective treatments against intracellular pathogens.

In this regard, extracellular products or their immunogenic analogs have been used to stimulate prophylactic or protective immunity against intracellular pathogens. For example, U.S. Pat. No. 5,108,745, issued Apr. 28, 1992, to Marcus A. Horwitz, discloses vaccines and methods of producing protective immunity against *Legionella pneumophila* and *Mycobacterium tuberculosis* as well as other intracellular pathogens. Unlike traditional vaccines which rely on the use of attenuated pathogens or non-infectious components of the pathogens themselves to stimulate a protective immune response, these prior art vaccines are broadly based on the use of extracellular products. Originally derived from proteinaceous and other compounds released extracellularly by the pathogenic bacteria into broth culture in vitro and released extracellularly by bacteria within infected host cells in vivo, these vaccines are based on the identification of extracellular products or their analogs which stimulate a strong immune response against the target pathogen in a mammalian host.

More specifically, these prior art candidate extracellular products were screened by determining their ability to provoke either a strong lymphocyte proliferative response or a cutaneous delayed-type hypersensitivity response in mammals which were immune to the pathogen of interest. Following the growth and harvesting of the bacteria, by virtue of their physical abundance, the principal extracellular products were separated from intrabacterial and other components through centrifugation and filtration. If desired, the resultant bulk filtrate could be then subjected to fractionation using ammonium sulfate precipitation with subsequent dialysis to give a mixture of extracellular products, commonly termed EP. Solubilized extracellular products in the dialyzed fractions were then purified to substantial homogeneity using suitable chromatographic techniques as known in the art.

These exemplary procedures resulted in the identification of dozens of compounds and in the subsequent production of fourteen individual proteinaceous major extracellular products, referred to as the majorly abundant extracellular products of *M. tuberculosis*, having molecular weights ranging from 110 kilo Daltons (KD) to 12 KD. Following purification each individual majorly abundant extracellular product exhibited one band corresponding to its respective molecular weight when subjected to polyacrylamide gel electrophoresis, thereby allowing individual products or groups of products corresponding to the majorly abundant extracellular products to be identified and isolated. The purified majorly abundant extracellular products have been characterized and distinguished further by determining all or part of their respective amino acid sequences using techniques common in the art. Sequencing may also provide information regarding possible structural relationships between the majorly abundant extracellular products and those of other pathogens.

Although effective at providing a new class of vaccines operating on a new functional mechanism, the prior art has yet to effectively address the therapeutic treatment of infection by pathogenic intracellular organisms. This is particularly true for those pathogenic organisms that have developed resistance to conventional antibiotic drugs. Accordingly, it is a principal object of the present invention to provide a new class of prophylactic and chemotherapeutic agents and methods for their production and use in combatting infectious intracellular pathogens, including intracellular bacterial pathogens.

It is another object of this invention to provide prophylactic and chemotherapeutic methods and agents for treatment of diseases caused by intracellular mycobacterial pathogens including *M. tuberculosis, M. bovis, M. avium, M. kansasii, M. fortuitum, M. chelonei, M. marinum, M. scrofulaceum, M. leprae, M. africanum, M. ulcerans* and *M. microti.*

It is an additional object of this invention to provide such prophylactic and therapeutic methods and agents which exhibit reduced toxicity relative to other known treatment methods.

It is another object of this invention to provide antibiotics which are effective against diseases caused by drug-resistant strains of intracellular pathogens present in mammalian hosts.

SUMMARY OF THE INVENTION

The present invention accomplishes the above-described and other objects by providing an entirely new functional class of antibiotics for use as targeted prophylactic and chemotherapeutic agents against infectious pathogenic organisms. Unlike conventional antibiotics which are directed at metabolic and synthetic pathways occurring within the internal cellular environment of the infectious pathogen, the methods and compositions of the present invention are directed at blocking or inhibiting the function of essential enzymes released extracellularly by the infectious organism. In accordance with the teachings of the present invention, one or more extracellular enzymes necessary for the growth or survival of the pathogenic organism is identified in the extracellular milieu and then blocked or inhibited to interfere with its functional activity and thereby inhibit the growth or survival of the infectious organism. In this manner it is possible to treat effectively disease conditions associated with sequestered intracellular pathogenic organisms without harming the infected host.

Because of its novel mode of operation, the present invention is effective against a wide variety of pathogens particularly intracellular pathogens. More specifically, the present invention is effective against intracellular bacteria, including intracellular mycobacteria, such as *M. tuberculosis, M. bovis, M. avium, M. kansasii, M. fortuitum, M. chelonei, M. marinum, M. scrofulaceum, M. leprae, M. africanum, M. ulcerans* and *M. microti.*

An exemplary embodiment of the present invention utilizes an antibiotic targeted to interfere with an extracellular enzyme released by *M. tuberculosis*. For example, in accordance with the teachings of the present invention, the compound L-methionine-S-sulfoximine (MS), analogs thereof, and related compounds inhibit the activity of the extracellular enzyme glutamine synthetase (GS), a 58 kilo Dalton (58 KD) extracellular protein which is essential for the growth of *M. tuberculosis* and other closely related pathogenic intracellular mycobacteria. Inhibition of the activity of *M. tuberculosis* glutamine synthetase, specifically that enzyme which is released extracellularly, has unexpectedly been found to inhibit the growth of *M. tuberculosis* cells as well.

An alternative embodiment of the present invention targets the same extracellular enzyme of *M. tuberculosis* but interferes with its functional activity by blocking production and subsequent extracellular release of the enzyme. For example, antisense oligodeoxynucleotides (ODN) which prevent expression of extracellular enzymes essential for the growth or survival of various pathogenic intracellular mycobacteria, can be used to treat infection by such mycobacteria. In this manner, ODNs derived from the gene encoding *M. tuberculosis* glutamine synthetase can be used as antisense oligodeoxynucleotides for inhibiting the growth of *M. tuberculosis*, thereby treating the infection and resultant disease condition.

Other objects, features and advantages of the present invention will be apparent to those skilled in the art from a consideration of the following detailed description of exemplary embodiments thereof taken in conjunction with the drawings which will first be described briefly.

DETAILED DESCRIPTION

Figures 1, 2:
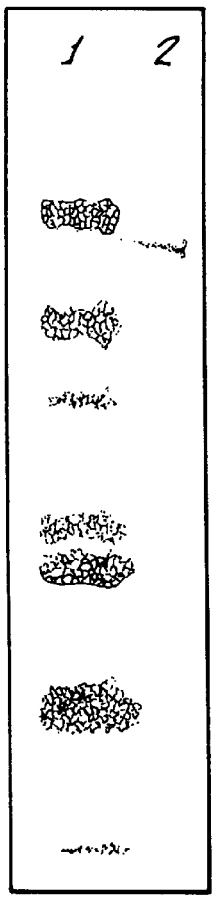
FIG. 1 is a representation of a coomassie blue stained gel illustrating the purification of the 58 KD protein of the majorly abundant extracellular products of *M. tuberculosis* as identified by sodium dodecyl sulfate polyacrylamide gel electrophoresis (SDS-PAGE)
FIG. 2 is a tabular representation identifying the five N-terminal amino acids of fourteen exemplary majorly abundant extracellular products of *M. tuberculosis* (Sequence ID Nos. 1–14) and the apparent molecular weight for such products.
Figure 3:
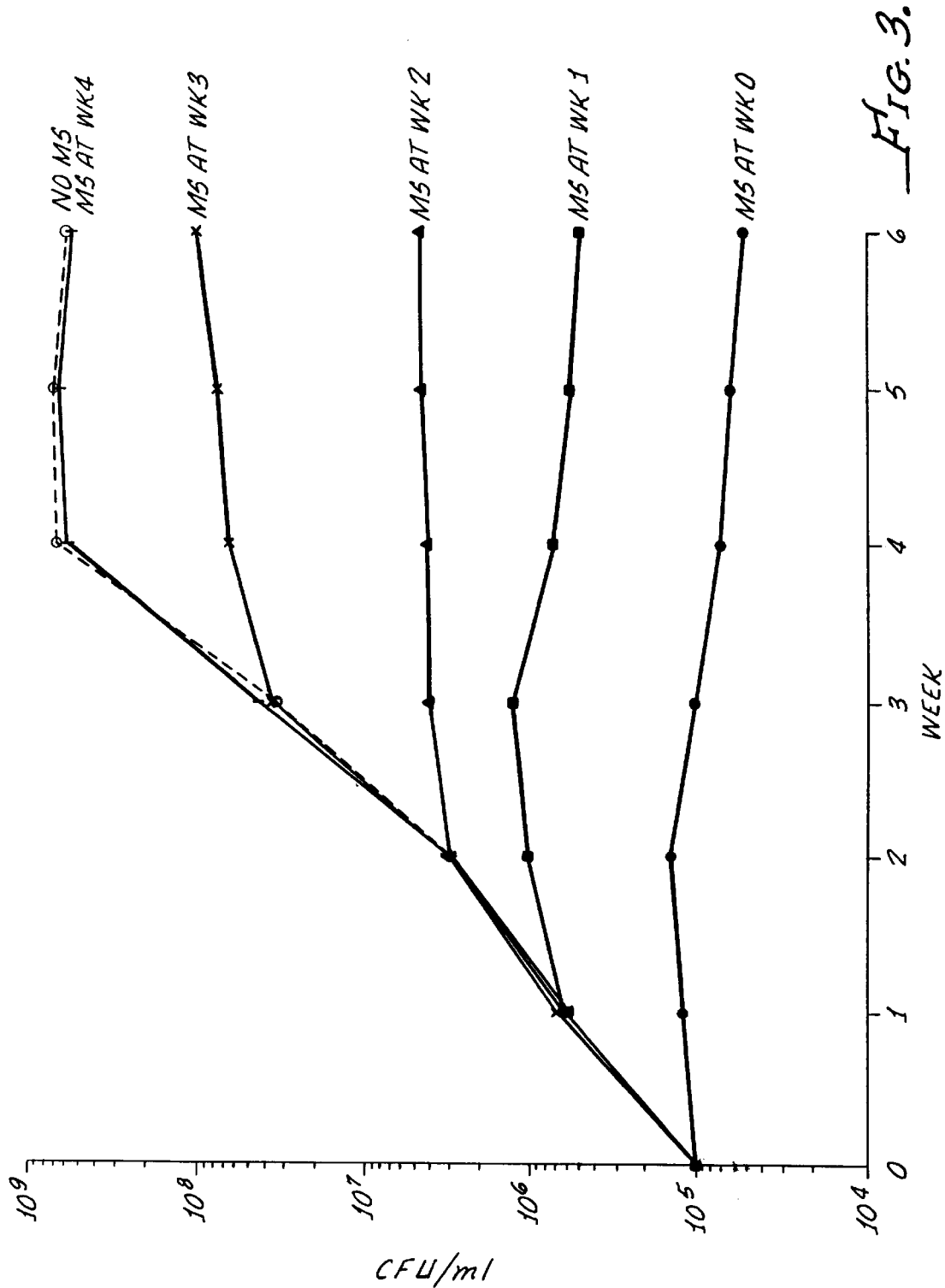
FIG. 3 is a graphical comparison of the effect upon *M. tuberculosis* cell growth of L-methionine-S-sulfoximine added to broth cultures at various times.

In a broad aspect, the present invention is directed to methods and associated compositions for the effective treatment of mammalian disease conditions associated with infection by one or more pathogenic organisms. Because the present invention relies upon the unique mechanism of targeting extracellular enzymes necessary for the growth or survival of the pathogenic organism, it is particularly effective against intracellular pathogens. Moreover, the present invention is useful against pathogenic organisms as both a prophylactic or therapeutic treatment.

More specifically, in complete contrast to the teachings of the prior art, the present invention is able to effectively treat disease conditions associated with infections by pathogenic agents through the simple steps of identifying one or more extracellular enzymes necessary for the growth or survival of the causative pathogenic organism, and then interfering with the functional activity of that extracellular enzyme. Although the function of the majority of extracellular products is not well understood, and not wishing to be bound by this theory, it is believed that extracellular enzymes function to modify the environment surrounding the pathogen or host cell harboring the sequestered intracellular pathogen. Blocking or inhibiting this functional activity outside the pathogenic cell or its host cell thereby impacts the ability of the pathogen to grow or survive. Thus, in accordance with the teachings of the present invention, it is not essential to modify metabolic, synthetic, or other cellular mechanisms occurring within the target pathogen because the methods and compositions of the present invention exhibit their antibiotic activity by virtue of the effect they have upon the extracellular products of the pathogen.

Though it is contemplated as being within the scope of the present invention to target a wide variety of pathogenic organisms and associated extracellular products, an exemplary pathogen illustrative of the teachings of the present invention is *M. tuberculosis*. Of the extracellular products produced by *M. tuberculosis*, one exemplary extracellular product has been identified as being necessary for the growth of *M. tuberculosis*. This particular extracellular product has a molecular weight of 58 KD and is a protein with an enzymatic activity. Known as glutamine synthetase, it can be isolated from the extracellular medium of cultures of *M. tuberculosis*.

In accordance with the teachings of the present invention, the functional activity of glutamine synthetase can be inhibited through the administration of L-methionine-S-sulfoximine. This inhibition of the functional activity of the 58 KD extracellular product of *M. tuberculosis* effectively treats the resultant disease condition caused by the mycobacterial infection without exhibiting toxic effect directed toward the infected host organism. Accordingly, interfering with the functional activity of the 58 KD extracellular enzyme glutamine synthetase of *M. tuberculosis* through the administration of L-methionine-S-sulfoximine is an excellent example illustrating the operability and effectiveness of the present invention. Those skilled in the art will appreciate that the present invention is not limited to this specific example and that other pathogens and extracellular enzymes may be targeted in accordance with the teachings therewith.

Those skilled in the art will also appreciate that the identification of one or more extracellular enzymes necessary for the growth or survival of the targeted pathogenic organism typically involves additional steps of isolation and purification of the extracellular enzyme. This may be followed by additional characterization including DNA sequencing as follows.

The following example illustrates the isolation and purification of the exemplary extracellular enzyme glutamine synthetase from *M. tuberculosis*.

EXAMPLE 1

Cultures of *M. tuberculosis* Erdman strain (ATCC 35801) were harvested at late log phase after a growth period of 3 weeks at 37° C. and 5% $CO_2$/95% air by filtration first through 0.8 µm membranes and then through 0.2 µm membranes. Cells were discarded and the entire volume (15L) of culture filtrate, representing the starting material for the purification of glutamine synthetase, was concentrated in a tangential flow concentrator to 160 ml using a membrane with a molecular weight cutoff of 10 KD. Proteins were precipitated by the addition of 0.3 volume of a saturated ammonium sulfate solution, adjusted to pH 4.4 with 1M acetic acid. After stirring the solution for 20 min at 4° C., precipitated proteins were collected by centrifugation for 1 h at 24,000×g and resuspended in 100 mM Imidazole/10 mM $MnCl_2$ pH 7 at 4° C. for 16 h. The suspension was centrifuged at 24,000×g for 1 h to pellet particulate material, and the protein solution containing glutamine synthetase was adjusted to 0.2 M NaCl and loaded on a 25 ml Affi-Gel blue column, equilibrated with the same buffer. The column was washed with 100 mM Imidazole/10 mM MnCl$_2$/10 mM NaCl, and the proteins were eluted with 10 mM Imidazole/10 mM MnCl$_2$/5 mM Na-ADP pH 7. Pooled fractions (15–30 ml) were concentrated 15-fold in a Speed-Vac concentrator to 1–2 ml and directly applied to a 50 ml Superdex 75 column, equilibrated with 10 mM Imidazole/10 mM MnCl$_2$/150 mM NaCl. Glutamine synthetase positive fractions were pooled and dialyzed extensively for 2–4 days, with at least 4 buffer changes, against 15 mM Imidazole/2.2 mM MnCl$_2$ pH 7 at 4° C. The final volume was 6 ml containing 3 mg of homogeneously purified glutamine synthetase which was monitored using SDS-PAGE and exhibited the single band shown in FIG. 1, col. 2. This preparation was stored at 4° C. in sterile containers.

FIG. 1 illustrates an exemplary 12% acrylamide gel developed using SDS-PAGE. The standard in lane 1 has proteins with molecular masses of 66, 45, 36, 29, 24, 20, and 14 KD. Lane 2 contains the purified 58 KD protein, glutamine synthetase. Preliminary amino acid sequencing was performed on the purified glutamine synthetase using techniques well known in the art. The 5 amino acid N-terminal sequence, represented using standard one-letter abbreviations for the naturally occurring amino acids, compared with those of the other 13 majorly abundant extracellular proteins of *M. tuberculosis* is shown in FIG. 2 (Sequence ID Nos. 1–14).

The following example illustrates the results of subsequent additional characterization of the 58 KD extracellular cellular protein, glutamine synthetase, of Example 1.

EXAMPLE 2

DNA sequencing was performed on the gene encoding the 58 KD extracellular protein, glutamine synthetase, from Example 1, using techniques well-known in the art. The DNA sequence and the corresponding amino acids are shown below.

```
1/1                                     31/11                                      (Sequence ID No. 15)
gtg ACG GAA AAG ACG CCC GAC GAC GTC TTC AAA CTT GCC AAG GAC GAG AAG GTC GAA TAT
val thr glu lys thr pro asp asp val phe lys leu ala lys asp glu lys val glu tyr 61/21                                   91/31
GTC GAC GTC CGG TTC TGT GAC CTG CCT GGC ATC ATG CAG CAC TTC ACG ATT CCG GCT TCG
val asp val arg phe cys asp leu pro gly ile met gln his phe thr ile pro ala ser 121/41                                  151/51
GCC TTT GAC AAG AGC GTG TTT GAC GAC GGC TTG GCC TTT GAC GGC TCG TCG ATT CGC GGG
ala phe asp lys ser val phe asp asp gly leu ala phe asp gly ser ser ile arg gly 181/61                                  211/71
TTC CAG TCG ATC CAC GAA TCC GAC ATG TTG CTT CTT CCC GAT CCC GAG ACG GCG CGC ATC
phe gln ser ile his glu ser asp met leu leu leu pro asp pro glu thr ala arg ile 241/81                                  271/91
GAC CCG TTC CGC GCG GCC AAG ACG CTG AAT ATC AAC TTC TTT GTG CAC GAC CCG TTC ACC
asp pro phe arg ala ala lys thr leu asn ile asn phe phe val his asp pro phe thr 301/101                                 331/111
CTG GAG CCG TAC TCC CGC GAC CCG CGC AAC ATC GCC CGC AAG GCC GAG AAC TAC CTG ATC
leu glu pro tyr ser arg asp pro arg asn ile ala arg lys ala glu asn tyr leu ile 361/121                                 391/131
AGC ACT GGC ATC GCC GAC ACC GCA TAC TTC GGC GCC GAG GCC GAG TTC TAC ATT TTC GAT
ser thr gly ile ala asp thr ala tyr phe gly ala glu ala glu phe tyr ile phe asp 421/141                                 451/151
TCG GTG AGC TTC GAC TCG CGC GCC AAC GGC TCC TTC TAC GAG GTG GAC GCC ATC TCG GGG
ser val ser phe asp ser arg ala asn gly ser phe tyr glu val asp ala ile ser gly 481/161                                 511/171
TGG TGG AAC ACC GGC GCG GCG ACC GAG GCC GAC GGC AGT CCC AAC CGG GGC TAC AAG GTC
trp trp asn thr gly ala ala thr glu ala asp gly ser pro asn arg gly tyr lys val 541/181                                 571/191
CGC CAC AAG GGC GGG TAT TTC CCA GTG GCC CCC AAC GAC CAA TAC GTC GAC CTG CGC GAC
arg his lys gly gly tyr phe pro val ala pro asn asp gln tyr val asp leu arg asp 601/201                                 631/211
AAG ATG CTG ACC AAC CTG ATC AAC TCC GGC TTC ATC CTG GAG AAG GGC CAC CAC GAG GTG
lys met leu thr asn leu ile asn ser gly phe ile leu glu lys gly his his glu val 661/221                                 691/231
GGC AGC GGC GGA CAG GCC GAG ATC AAC TAC CAG TTC AAT TCG CTG CTG CAC GCC GCC GAC
gly ser gly gly gln ala glu ile asn tyr gln phe asn ser leu leu his ala ala asp 721/241                                 751/251
GAC ATG CAG TTG TAC AAG TAC ATC ATC AAG AAC ACC GCC TGG CAG AAC GGC AAA ACG GTC
asp met gln leu tyr lys tyr ile ile lys asn thr ala trp gln asn gly lys thr val 781/261                                 811/271
ACG TTC ATG CCC AAG CCG CTG TTC GGC GAC AAC GGG TCC GGC ATG CAC TGT CAT CAG TCG
```

-continued

```
thr phe met pro lys pro leu phe gly asp asn gly ser gly met his cys his gln ser 841/281                                 871/291
CTG TGG AAG GAC GGG GCC CCG CTG ATG TAC GAC GAG ACG GGT TAT GCC GGT CTG TCG GAC
leu trp lys asp gly ala pro leu met tyr asp glu thr gly tyr ala gly leu ser asp 901/301                                 931/311
ACG GCC CGT CAT TAC ATC GGC GGC CTG TTA CAC CAC GCG CCG TCG CTG CTG GCC TTC ACC
thr ala arg his tyr ile gly gly leu leu his his ala pro ser leu leu ala phe thr 961/321                                 991/331
AAC CCG ACG GTG AAC TCC TAC AAG CGG CTG GTT CCC GGT TAC GAG GCC CCG ATC AAC CTG
asn pro thr val asn ser tyr lys arg leu val pro gly tyr glu ala pro ile asn leu 1021/341                                1051/351
GTC TAT AGC CAG CGC AAC CGG TCG GCA TGC GTG CGC ATC CCG ATC ACC GGC AGC AAC CCG
val tyr ser gln arg asn arg ser ala cys val arg ile pro ile thr gly ser asn pro 1081/361                                1111/371
AAG GCC AAG CGG CTG GAG TTC CGA AGC CCC GAC TCG TCG GGC AAC CCG TAT CTG GCG TTC
lys ala lys arg leu glu phe arg ser pro asp ser ser gly asn pro tyr leu ala phe 1141/381                                1171/391
TCC GCC ATG CTG ATG GGA GCC CTG GAC GGT ATC AAG AAC AAG ATC GAG CCG CAG GCG CCC
ser ala met leu met ala gly leu asp gly ile lys asn lys ile glu pro gln ala pro 1201/401                                1231/411
GTC GAC AAG GAT CTC TAC GAG CTG CCG CCG GAA GAG GCC GCG AGT ATC CCG CAG ACT CCG
val asp lys asp leu tyr glu leu pro pro glu glu ala ala ser ile pro gln thr pro 1261/921                                1291/431
ACC CAG CTG TCA GAT GTG ATC GAC CGT CTC GAG GCC GAC CAC GAA TAC CTC ACC GAA GGA
thr gln leu ser asp val ile asp arg leu glu ala asp his glu tyr leu thr glu gly 1321/441                                1351/451
GGG GTG TTC ACA AAC GAC CTG ATC GAG ACG TGG ATC AGT TTC AAG CGC GAA AAC GAG ATC
gly val phe thr asn asp leu ile glu thr trp ile ser phe lys arg glu asn glu ile 1381/461                                1411/471
GAGCCGGTCA ACATCCGGCC GCATCCCTAC GAATTCGCGC TGTACTACGA CGTT taa
glu pro val asn ile arg pro his pro tyr glu phe ala leu tyr tyr asp val OCH
```

The following example illustrates additional characterization and functional analysis of the 58 KD extracellular protein through the preparation and analysis of recombinant M. tuberculosis glutamine synthetase.

EXAMPLE 3

The M. tuberculosis glutamine synthetase gene was cloned into the E. coli/mycobacteria shuttle vector pSMT3 such that ~300 nucleotides upstream of the structural gene and 24 nucleotides downstream of the TAA stop codon were included. The glutamine synthetase promoter region has the same orientation as the plasmid encoded heat shock protein 60 promoter. The additional nucleotides at the 3' end contain a second, inframe stop codon 8 codons downstream of the first stop codon. The pSMT3 construct was electroporated (Zhang, Y., Lathigra, R., Garbe, T., Catty, D., and Young, D., 1991, *Mol. Microbiol.,* 5:381–391) into *M. smegmatis* 1–2c and recombinant colonies were selected for on 7H11 agar containing hygromycin at 50 μg/ml.

Out of a total of >2,000 recombinant clones (colonies), four clones were analyzed for expression of recombinant *M. tuberculosis* glutamine synthetase. Since the level of expression was similar for all four clones, one was chosen for more detailed analyses. At late log phase, *M. smegmatis* 1–2c carrying either pSMT3 alone or the pSMT3 construct containing the *M. tuberculosis* glutamine synthetase gene were harvested. Both culture filtrates and cells were analyzed for expression of glutamine synthetase by polyacrylamide gel electrophoresis and for the presence of glutamine synthetase activity by γ-glutamyl transferase assays (Harth, G., Clemens, D. L., and Horwitz, M. A., 1994, *Proc. Natl. Acad. Sci., USA,* 91:9342–9346).

In cells carrying pSMT3 alone, greater than 95% of the glutamine synthetase was intracellular. In contrast, in cells carrying the recombinant glutamine synthetase construct, virtually all the glutamine synthetase was extracellular. This result suggests that expression of recombinant glutamine synthetase has very little, if any, influence on the expression of endogenous glutamine synthetase, since the level of intracellular glutamine synthetase remained essentially constant and most of the recombinant enzyme molecules were released in the culture medium.

N-terminal amino acid sequencing of the extracellular enzyme revealed a glutamine synthetase molecule with N-terminus thr glu lys thr pro asp asp (Sequence ID No. 16) identical to that of the N-terminus of *M. tuberculosis* glutamine synthetase, but distinctly different from that of the N-terminus of *M. smegmatis* glutamine synthetase ala glu lys thr ser asp asp (Sequence ID No. 17) (differences underlined). This result confirms that the released glutamine synthetase is from *M. tuberculosis* and not *M. smegmatis.*

An extrapolation from these 50 ml cultures with ~6x$10_8$ cfu/ml to 1 liter cultures indicates a yield of recombinant glutamine synthetase of >1 mg/L, equivalent to ~2 million glutamine synthetase molecules per cell. The expressed recombinant glutamine synthetase was active in the transferase assay, indicating that the recombinant glutamine synthetase construct encompassing ~300 nucleotides upstream of the start codon of the structural gene contains all the necessary information for transcription, translation, and extracellular release of active glutamine synthetase. Moreover, this construct also shows that release into the culture medium of glutamine synthetase is somehow governed by information contained within the expressed protein, since the structural gene is not preceded by a leader peptide sequence.

Standardized for 100 million cells, the detectable glutamine synthetase activity amounted to 0.1 mU for cells carrying pSMT3 alone and 30 mU for cells carrying the recombinant glutamine synthetase construct. A control run in parallel with native M. tuberculosis Erdman glutamine synthetase gave a result of 25 mU per 100 million cells, consistent with earlier findings (Harth et al., op. cit.).

Further confirming the identification of the 58 KD extracellular enzyme glutamine synthetase of M. tuberculosis as necessary for the growth or survival of the pathogenic organism, the following example illustrates the inhibition of M. tuberculosis growth in broth cultures by L-methionine-S-sulfoximine, a known inhibitor of mammalian glutamine synthetase.

EXAMPLE 4

Six culture flasks containing Middlebrook 7H9 medium were inoculated with *M. tuberculosis*, Erdman strain, at an initial cell density of $1\times10^5$ colony forming units per ml. L-methionine-S-sulfoximine (MS) was added to the first culture flask in a concentration of 2000 $\mu$M and thereafter to 4 of the 5 remaining culture flasks at 1 week, 2 weeks, 3 weeks, and 4 weeks, respectively. As shown in FIG. 3, MS inhibited the growth of *M. tuberculosis* in broth cultures when added up to 3 weeks following inoculation.

The following examples illustrate that L-methionine-S-sulfoximine inhibits *M. tuberculosis, M. bovis*, and *M. avium* growth in broth cultures in a dose-dependent fashion.

EXAMPLE 5

Five culture flasks containing Middlebrook 7H9 medium were inoculated with *M. tuberculosis* Erdman strain at an initial cell density of $1\times10^5$ colony forming units per ml, corresponding to an optical density (OD) at 540 nm of 0.05. L-methionine-S-sulfoximine (MS) was added to 4 of the 5 culture flasks such that the final concentration of MS was 0, 0.2, 2, 20, and 200 $\mu$M. Growth of the *M. tuberculosis* organisms was monitored by measuring the $OD_{540}$ of the cultures at weekly intervals. As shown in FIG. 4, MS inhibited the growth of *M. tuberculosis* Erdman in broth culture at all concentrations tested. Growth was completely inhibited at concentrations of 200 and 20 $\mu$M MS and strongly inhibited at 2 $\mu$M MS. Similar results are shown for *M. tuberculosis* H37Rv in FIG. 5.

EXAMPLE 6

The procedure of Example 5 was repeated except that cultures were assayed for colony forming units (CFU) of *M. bovis*. As shown in FIG. 6, the number of CFU in cultures treated with MS was markedly decreased compared with that of cultures not treated with MS (No MS). Similar results are shown for *M. bovis* BCG in FIG. 7.

EXAMPLE 7

The procedure of Example 5 was repeated except that cultures were assayed for colony-forming units (CFU) of *M. avium* ATCC strain 25291, a serotype 2 *M. avium* strain in the group of *M. avium* organisms that are pathogenic.

As shown in FIG. 8, the number of CFU in cultures treated with MS was markedly decreased compared with that of cultures not treated with MS (no MS).

Further illustrating the unique operational mechanism of the present invention and its ability to target the functional activity of an extracellular enzyme present outside the target pathogenic organism, the following example illustrates that L-methionine-S-sulfoximine (MS) inhibits glutamine synthetase (GS) activity in extracellular fluid of broth cultures of *M. tuberculosis.*

EXAMPLE 8

*M. tuberculosis* was cultured as in Examples 4–6 for 1 week without MS and thereafter in the presence of various concentrations of L-methionine-S-sulfoximine (0, 0.2, 2, 20, and 200 $\mu$M). At 1 and 4 weeks, an aliquot of the culture was removed; the bacterial cells were pelleted by centrifugation; and the supernate was filtered through 0.2 $\mu$m membranes. The supernate was then assayed for glutamine synthetase activity using the transfer assay, as described by Harth et al. (op. cit.). As shown in FIG. 20, treatment of the cultures with MS resulted in a marked decrease in extracellular GS activity. At concentrations of 2–200 $\mu$M MS, little or no increase in extracellular GS activity occurred over 3 weeks of culture (week 1 to week 4).

*M. tuberculosis* releases about one-third of its total GS extracellularly. Similarly, it is known that *M. tuberculosis* and the other major pathogenic mycobacterium of humans, *M. bovis*, differ from nonpathogenic mycobacterial and non-mycobacterial bacteria in that they release a relatively high proportion of glutamine synthetase extracellularly (Harth et al., op. cit.).

EXAMPLE 9

The procedure of Example 8 was repeated except that cultures were assayed for the amount of glutamine synthetase activity released extracellularly by *M. avium* ATCC strain 25291. As can be seen from FIG. 23, *m. avium* released 7.3 mU per $10^8$ bacterial cells at 4 weeks ("No MS"). This amount is intermediate between that of non-pathogenic mycobacteria such as *M. smegmatis,* which release 0.06 mU per $10^8$ bacterial cells, and pathogenic mycobacteria such as *M. tuberculosis*, which release 25–30 mU per $10^8$ bacterial cells.

The concentration of MS required to completely inhibit glutamine synthetase activity was found to be 200 $\mu$M MS, which was higher than that required to inhibit the glutamine synthetase activity of the highly pathogenic strains of *M. tuberculosis* and *M. bovis.*

To further demonstrate the unique functionality of the present invention, the following example illustrates that L-methionine-S-sulfoximine does not inhibit cultures of exemplary non-pathogenic mycobacteria or non-mycobacteria.

EXAMPLE 10

The procedure of Example 5 was followed except that cultures of *M. phlei, M. smegmatis* 1—2C, *L. pneumophila* Philadelphia 1, and *E. coli* DH5α a were used. As shown in FIGS. 9,10, 11 and 12, concentrations of MS of 0.2, 2, 20, and 200 $\mu$M did not inhibit growth of either *M. phlei* (FIG. 9), or *M. smegmatis,* (FIG. 10), which are non-pathogenic mycobacteria, or the non-mycobacteria *L. pneumophila* (FIG. 11) or *E. coli* (FIG. 12).

In contrast, as shown in FIGS. 4 and 5, MS concentrations as low as 0.2 $\mu$M inhibited *M. tuberculosis* growth.

Further demonstrating that the present invention effectively targets the functional activity of extracellular enzymes as opposed to cell-associated enzymes, the following example illustrates that L-methionine-S-sulfoximine (MS) preferentially inhibits extracellular GS activity.

15

EXAMPLE 11

Cell-associated and extracellular GS activity of *M. tuberculosis* cultures were assayed in the presence of 20 μM MS. *M. tuberculosis* cultures were grown for 1 week without MS and then for 3 weeks additional in the presence of 0 or 20 μM MS. At 1, 2, 3, and 4 weeks, aliquots of the cultures were removed and the bacterial cells were separated from the extracellular fluid by centrifugation. The GS activity of the extracellular fluid was assayed by the transfer assay. The GS activity of the bacterial pellet (cell-associated GS activity) was assayed by the same transfer assay after first lysing the cells by freeze/thawing cycles and with detergent.

Figure 21:
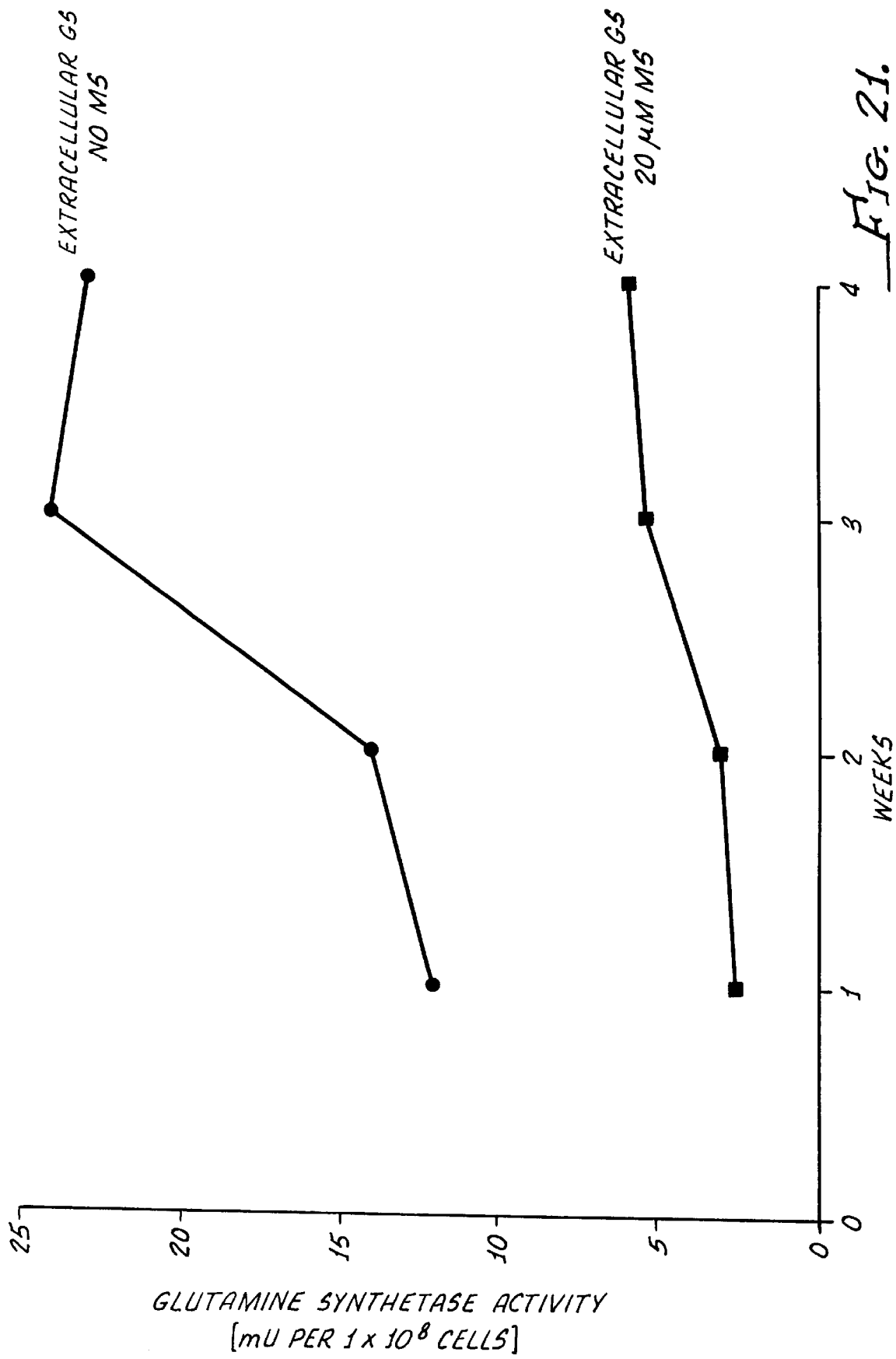
FIG. 21 is a graphical comparison of the effect upon extracellular glutamine synthetase activity of concentrations of 0 and 20 µM L-methionine-S-sulfoximine in *M. tuberculosis* broth cultures.
Figure 22:
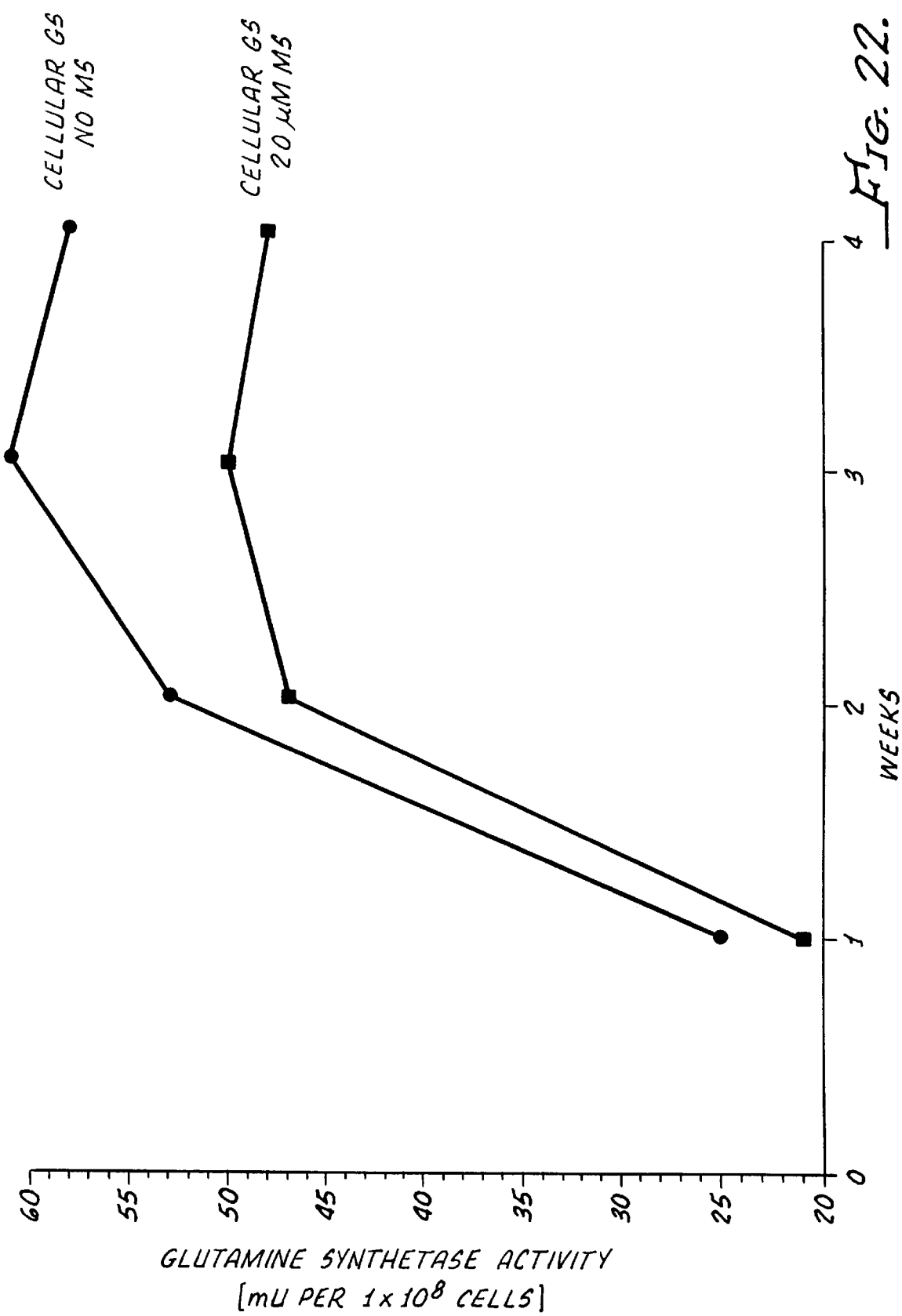
FIG. 22 is a graphical comparison of the effect upon cellular glutamine synthetase activity of concentrations of 0 and 20 µM L-methionine-S-sulfoximine in *M. tuberculosis* broth cultures.
Figure 23:
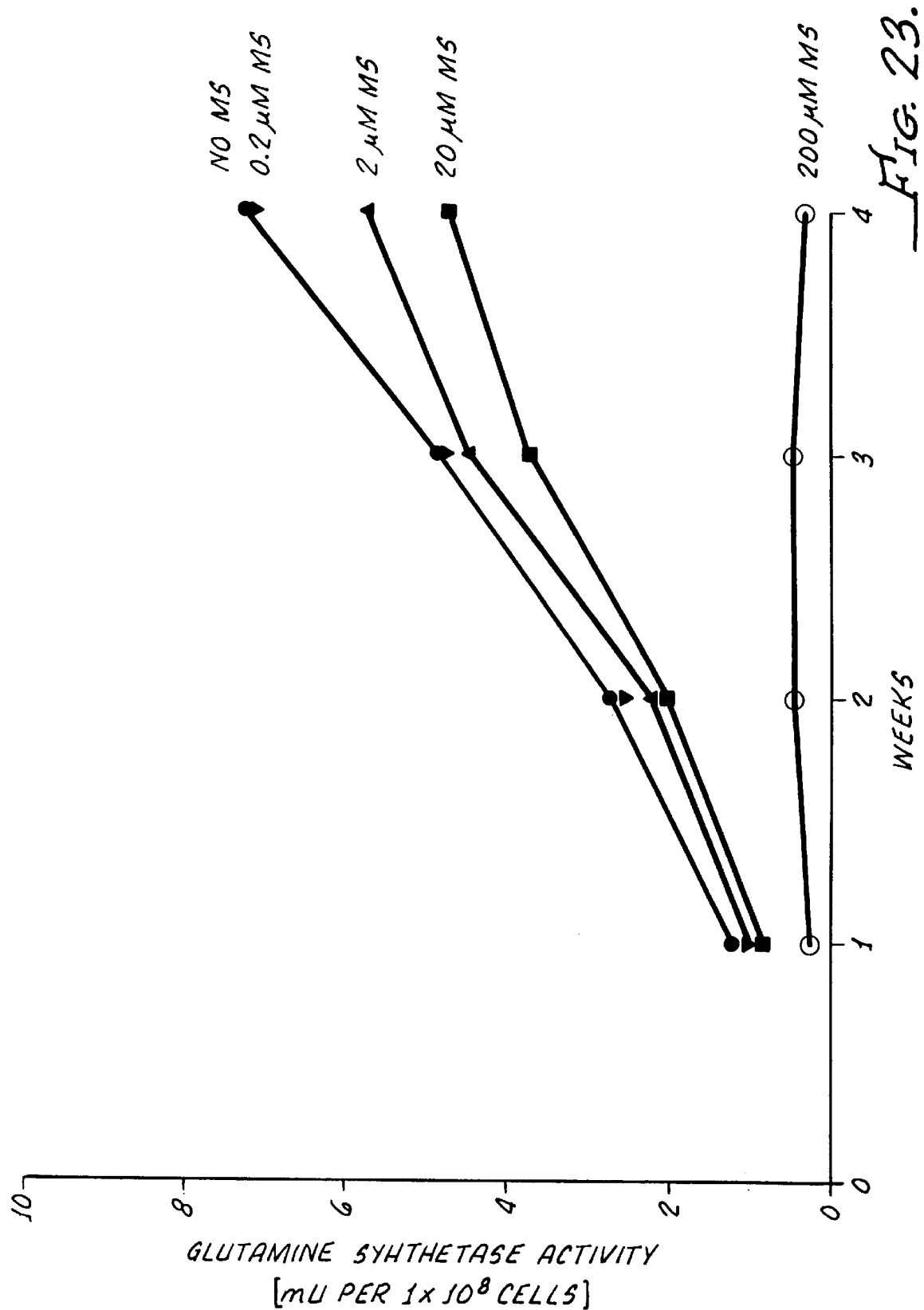
FIG. 23 is a graphical comparison of the effect upon extracellular glutamine synthetase activity of various concentrations of L-methionine-S-sulfoximine in *M. avium* broth cultures.

As shown in FIG. 21, extracellular GS activity was markedly reduced by MS to less than 25% of its value in untreated cultures. In contrast, as shown in FIG. 22, cell-associated GS activity ("Cellular GS") was only slightly reduced in cultures treated with 20 gM MS compared with its level in untreated cultures.

Several known inhibitors of glutamine synthetase activity were evaluated in accordance with the teachings of the present invention to determine their effectiveness in inhibiting the growth of *M. tuberculosis*. In comparisons of the effect upon *M. tuberculosis* growth of L-methionine-S-sulfoximine with the effect on growth of phosphinothricin, phosphinothricin had only a very minor inhibitory effect on *M. tuberculosis* growth. Similarly, the racemic compound DL-methionine-SR-sulfoximine exhibited a significantly weaker inhibitory effect on the growth of *M. tuberculosis* relative to L-methionine-S-sulfoximine. The following example illustrates the relative inhibitory capacity on *M. tuberculosis* growth of L-methionine-S-sulfoximine versus DL-methionine-SR-sulfoximine.

EXAMPLE 12

Figure 4:
FIG. 4 is a graphical comparison of the effect upon *M. tuberculosis* Erdman cell growth of L-methionine-S-sulfoximine added to broth cultures at various concentrations.
Figure 5:
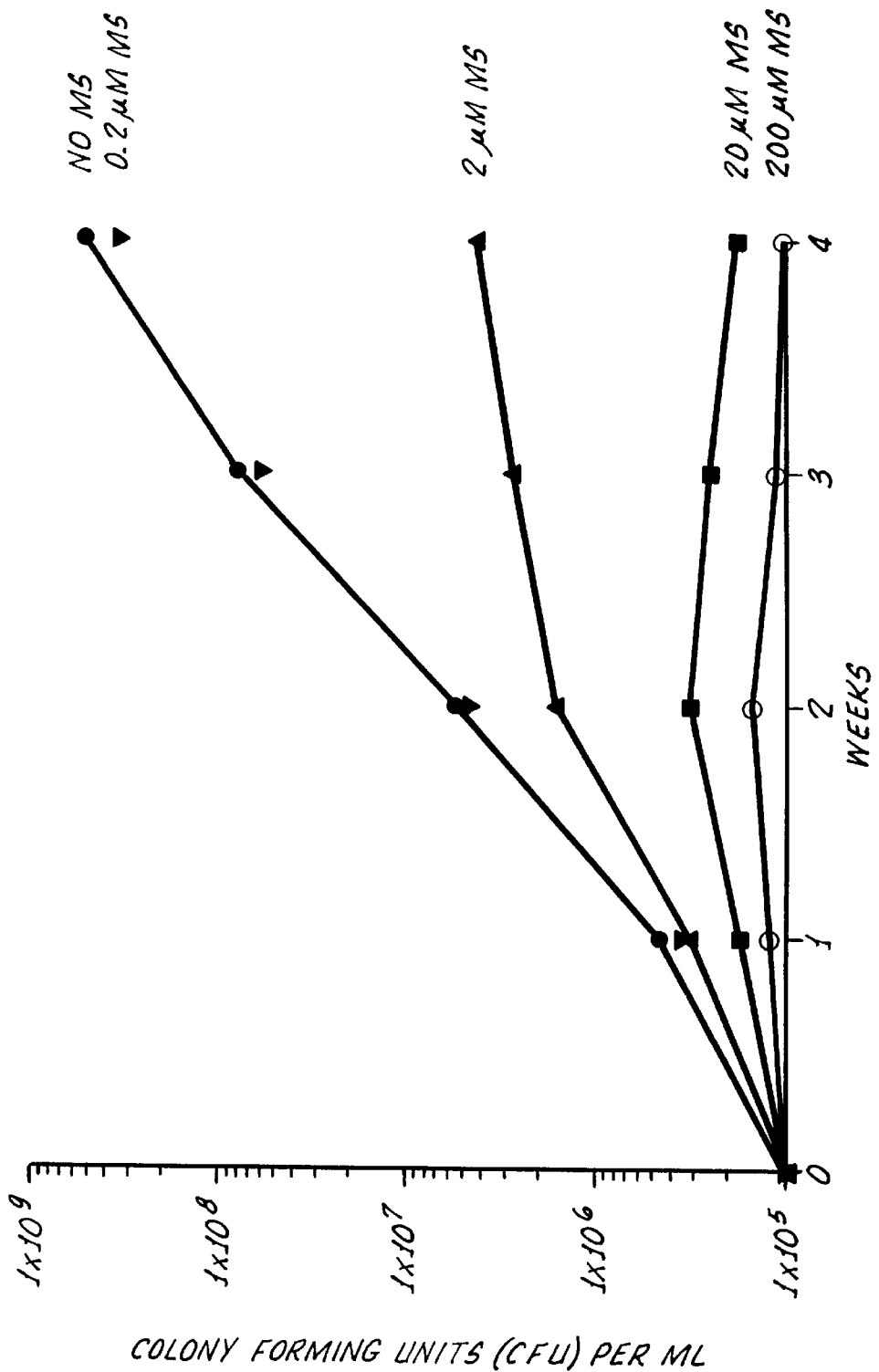
FIG. 5 is a graphical comparison of the effect upon *M. tuberculosis* H37Rv cell growth of L-methionine-S-sulfoximine added to broth cultures at various concentrations.
Figure 6:
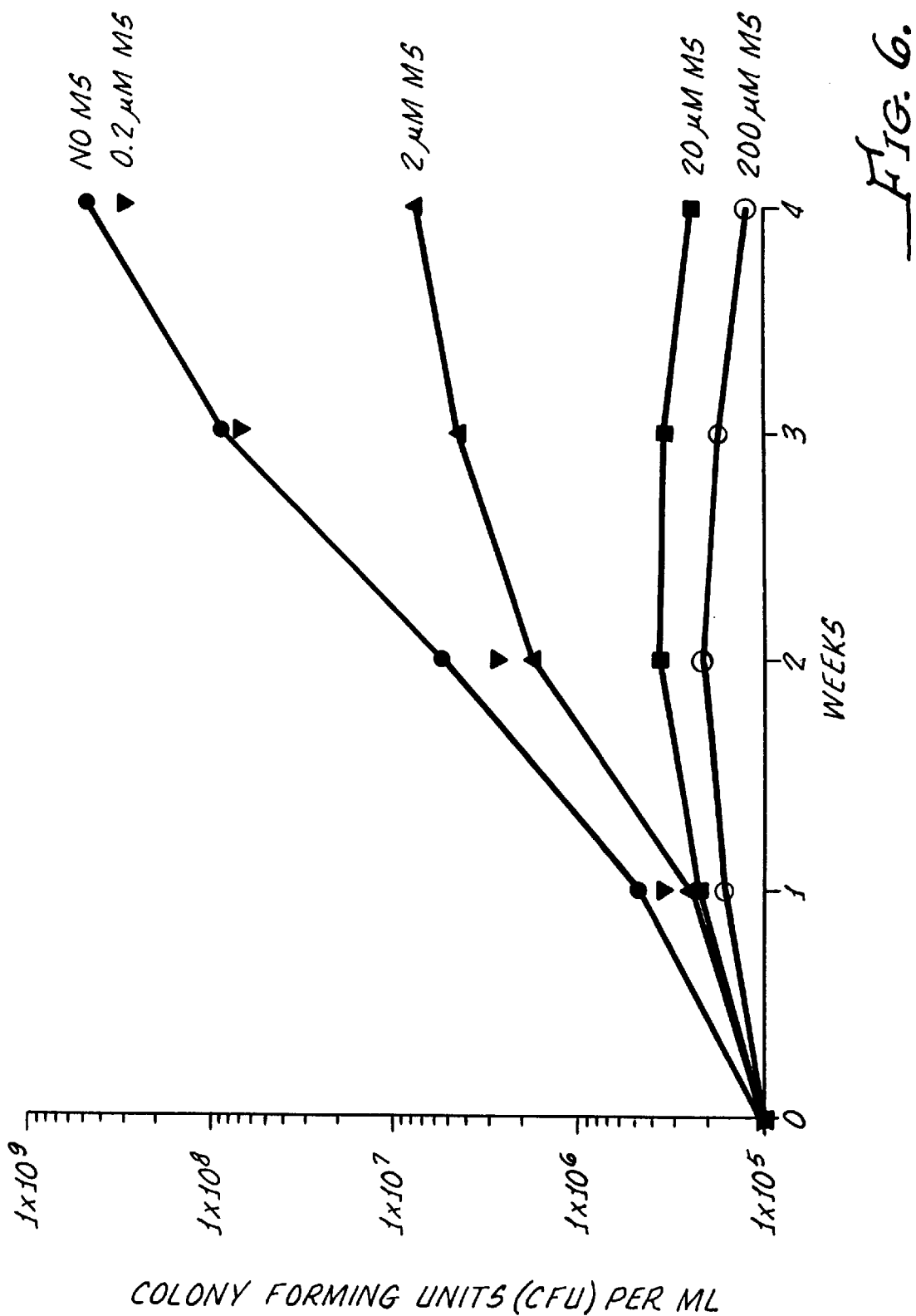
FIG. 6 is a graphical comparison of the effect upon *M. bovis* cell growth of L-methionine-S-sulfoximine added to broth cultures at various concentrations.
Figure 7:
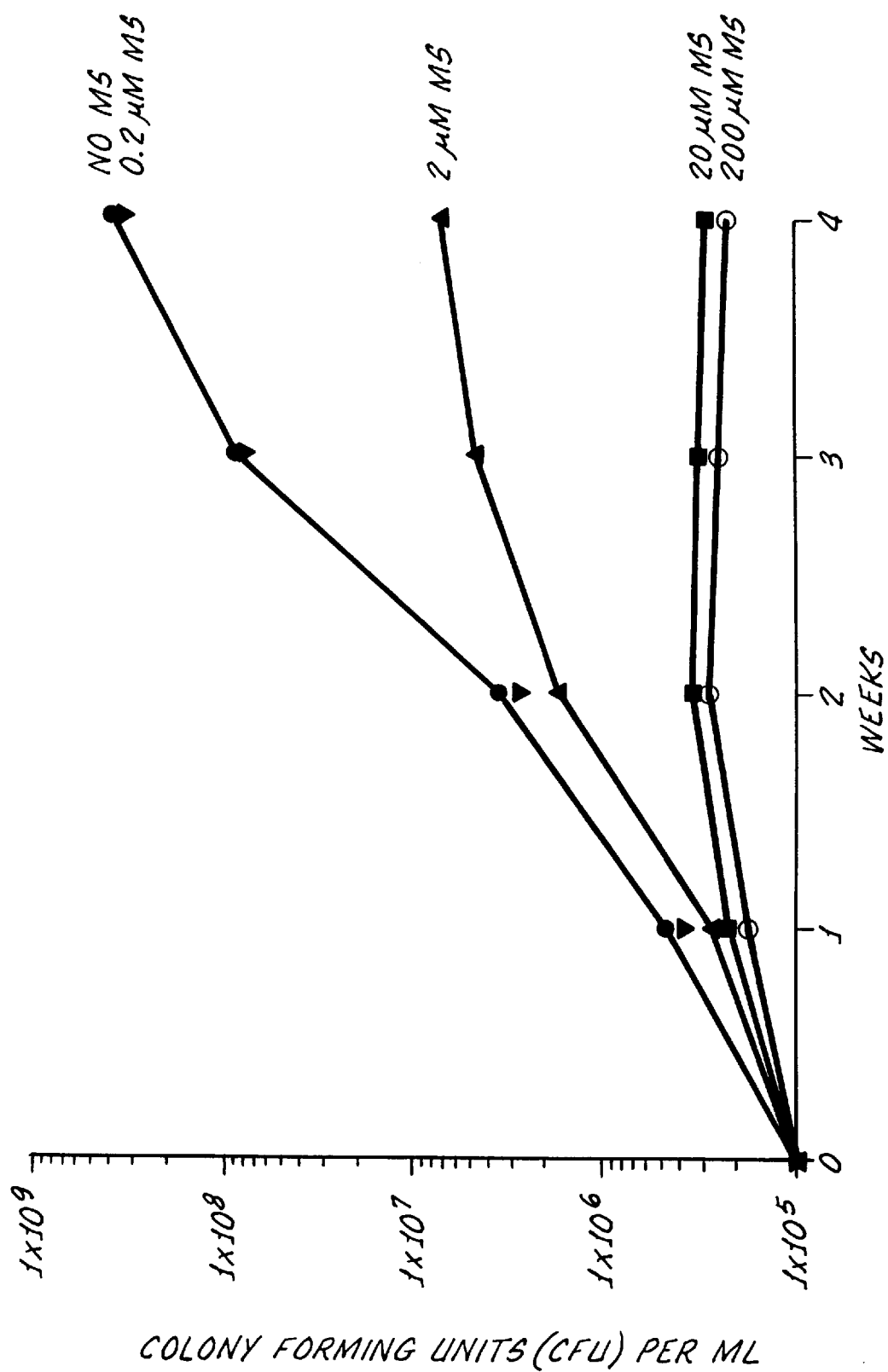
FIG. 7 is a graphical comparison of the effect upon *M. bovis* BCG cell growth of L-methionine-S-sulfoximine added to broth cultures at various concentrations.
Figure 8:
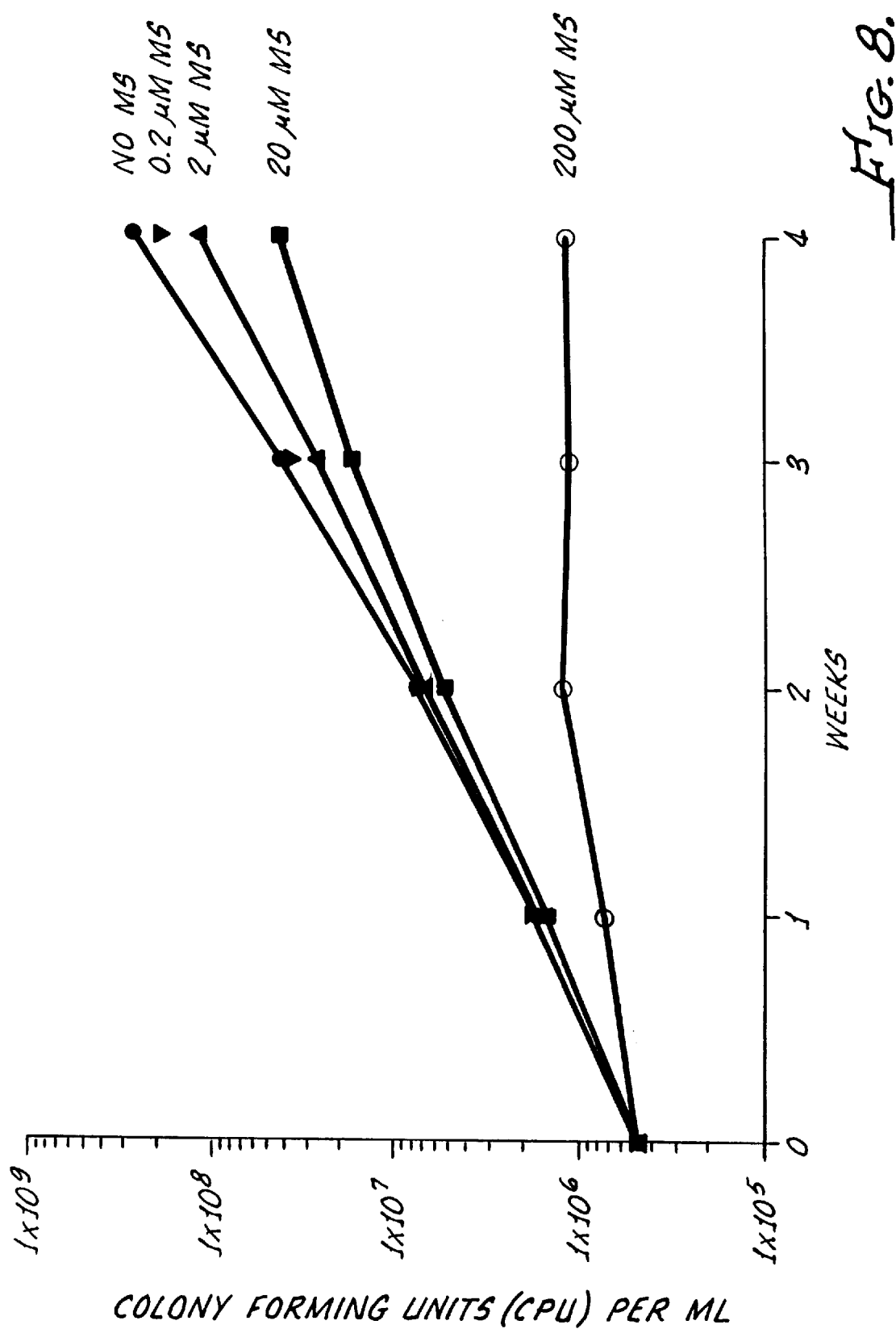
FIG. 8 is a graphical comparison of the effect upon *M. avium* cell growth of L-methionine-S-sulfoximine added to broth cultures at various concentrations.
Figure 9:
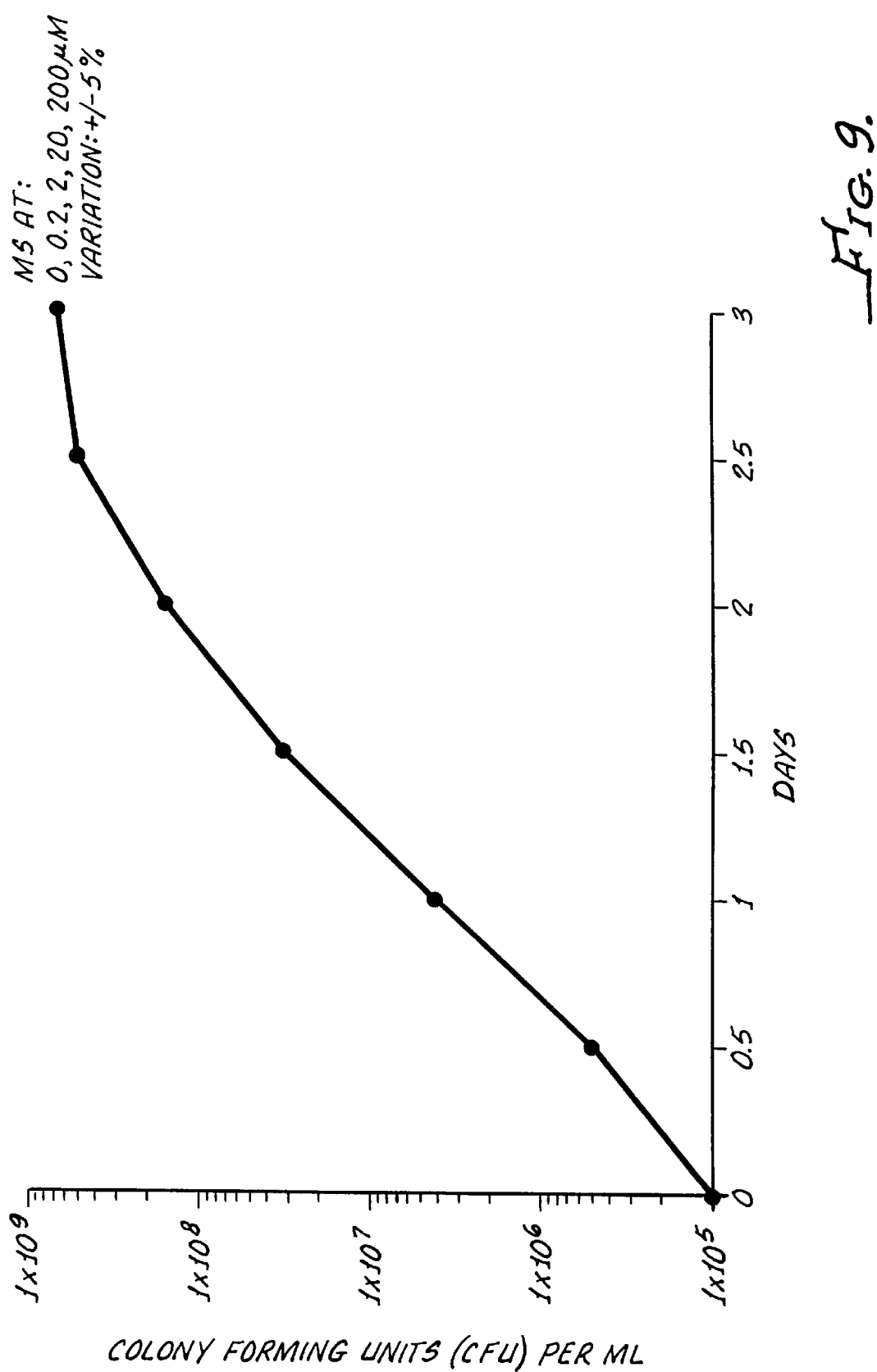
FIG. 9 is a graphical depiction of the lack of effect upon *M. phlei* cell growth of the addition of L-methionine-S-sulfoximine to broth cultures.
Figure 10:
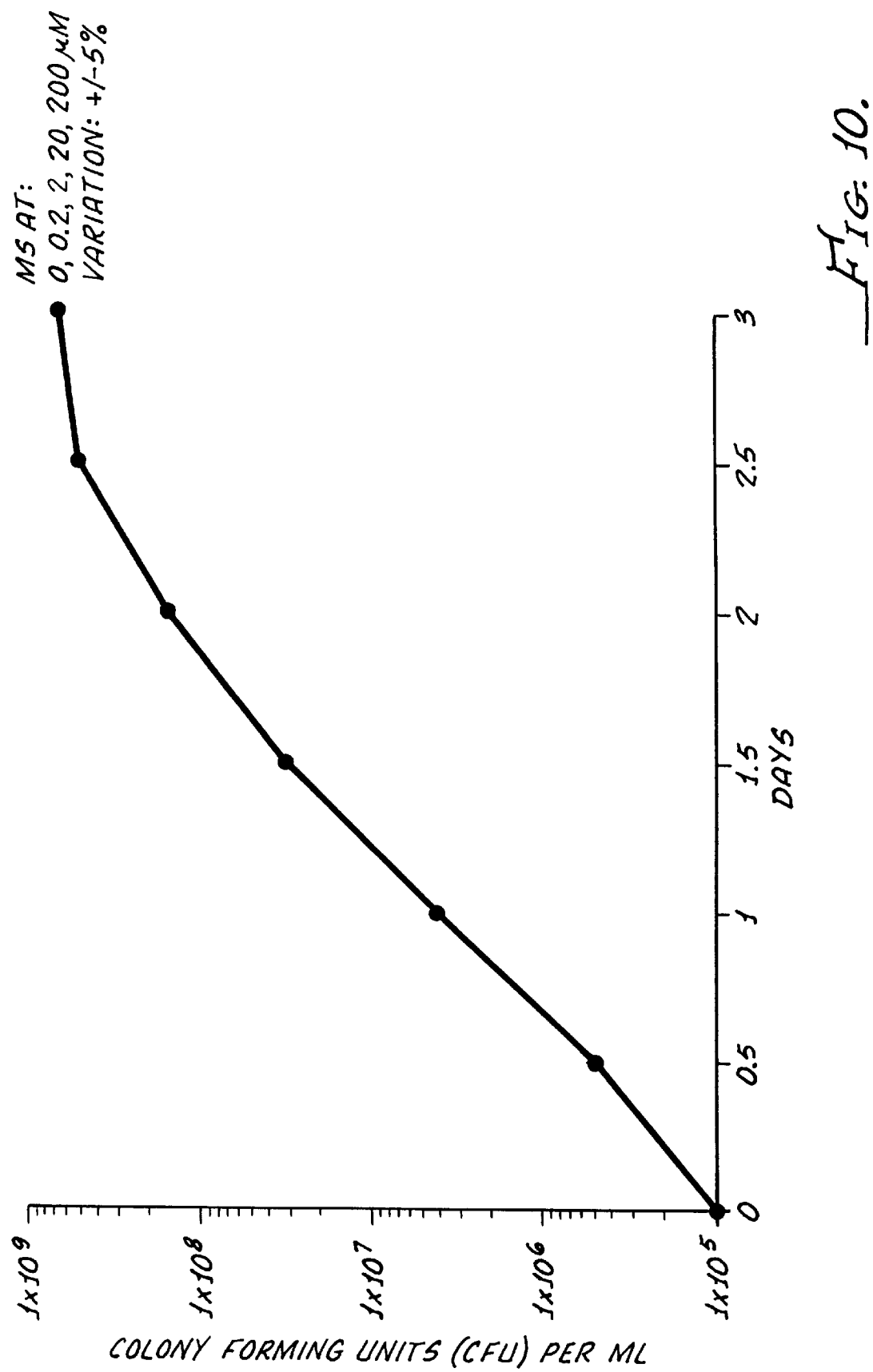
FIG. 10 is a graphical depiction of the lack of effect upon *M. smegmatis* 1–2c cell growth of the addition of L-methionine-S-sulfoximine to broth cultures.
Figure 11:
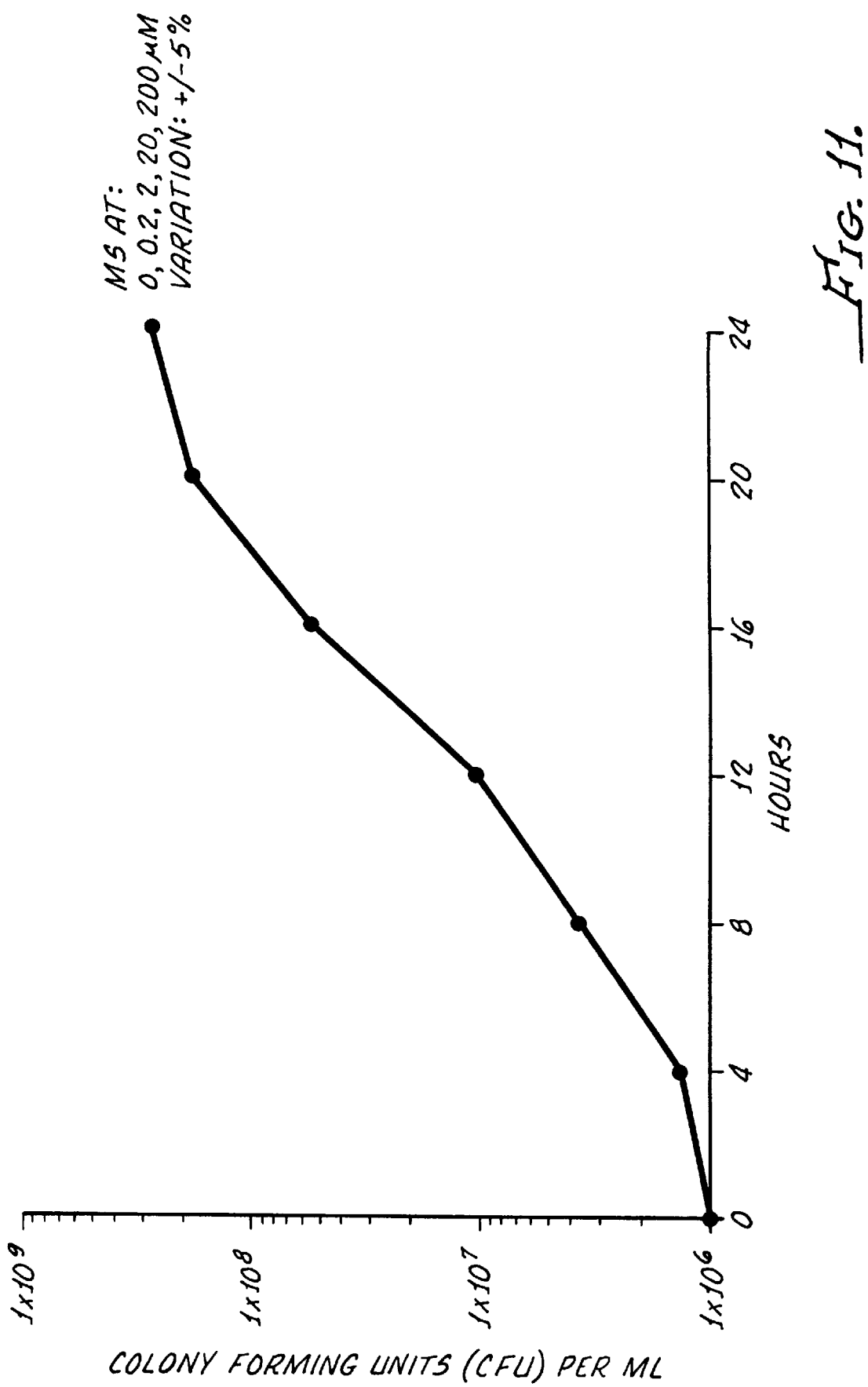
FIG. 11 is a graphical depiction of the lack of effect upon *L. pneumophila* Philadelphia 1 cell growth of the addition of L-methionine-S-sulfoximine to broth cultures.
Figure 12:
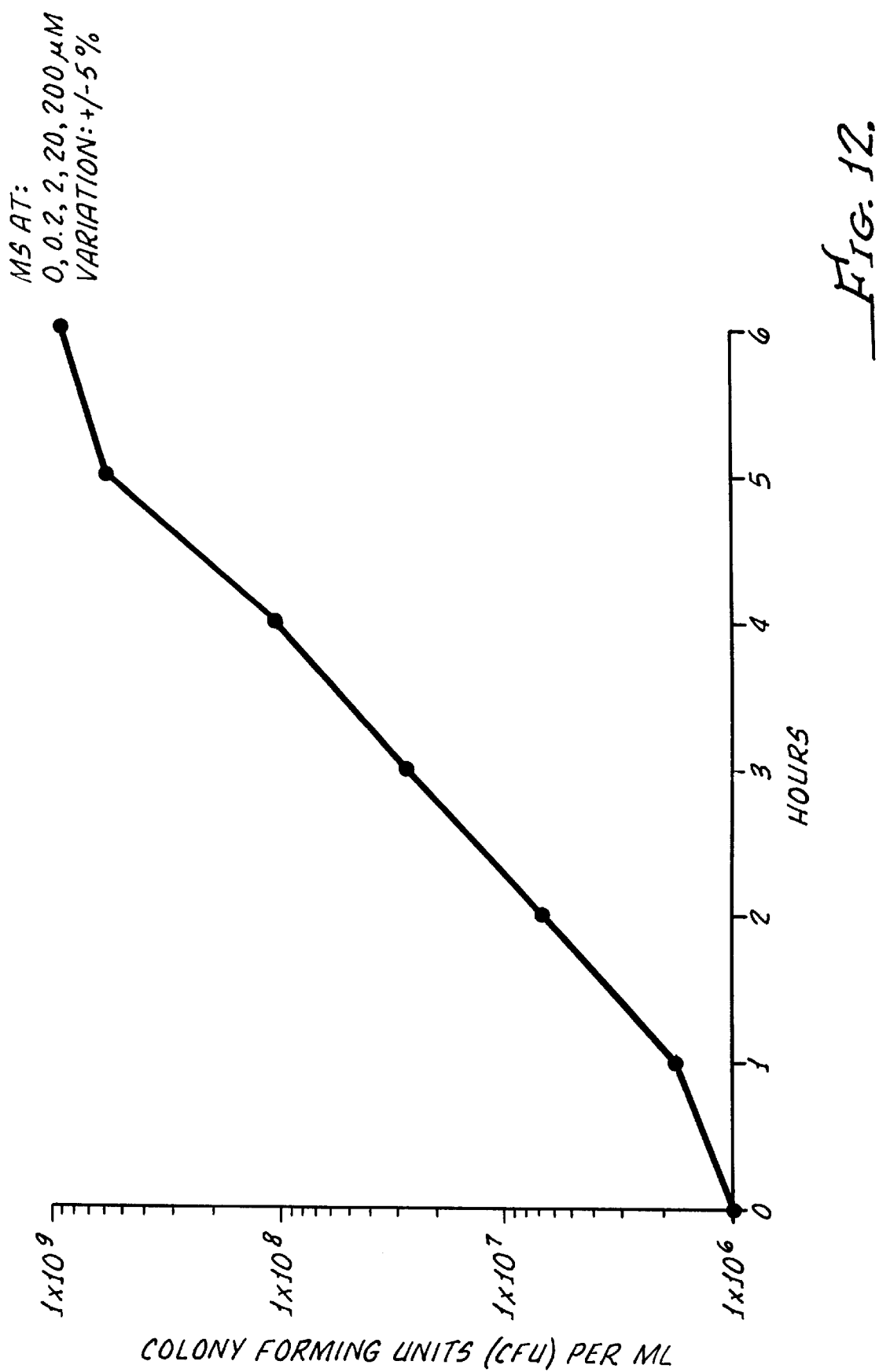
FIG. 12 is a graphical depiction of the lack of effect upon *E. coli* DH5α cell growth of the addition of L-methionine-S-sulfoximine to broth cultures.
Figure 13:
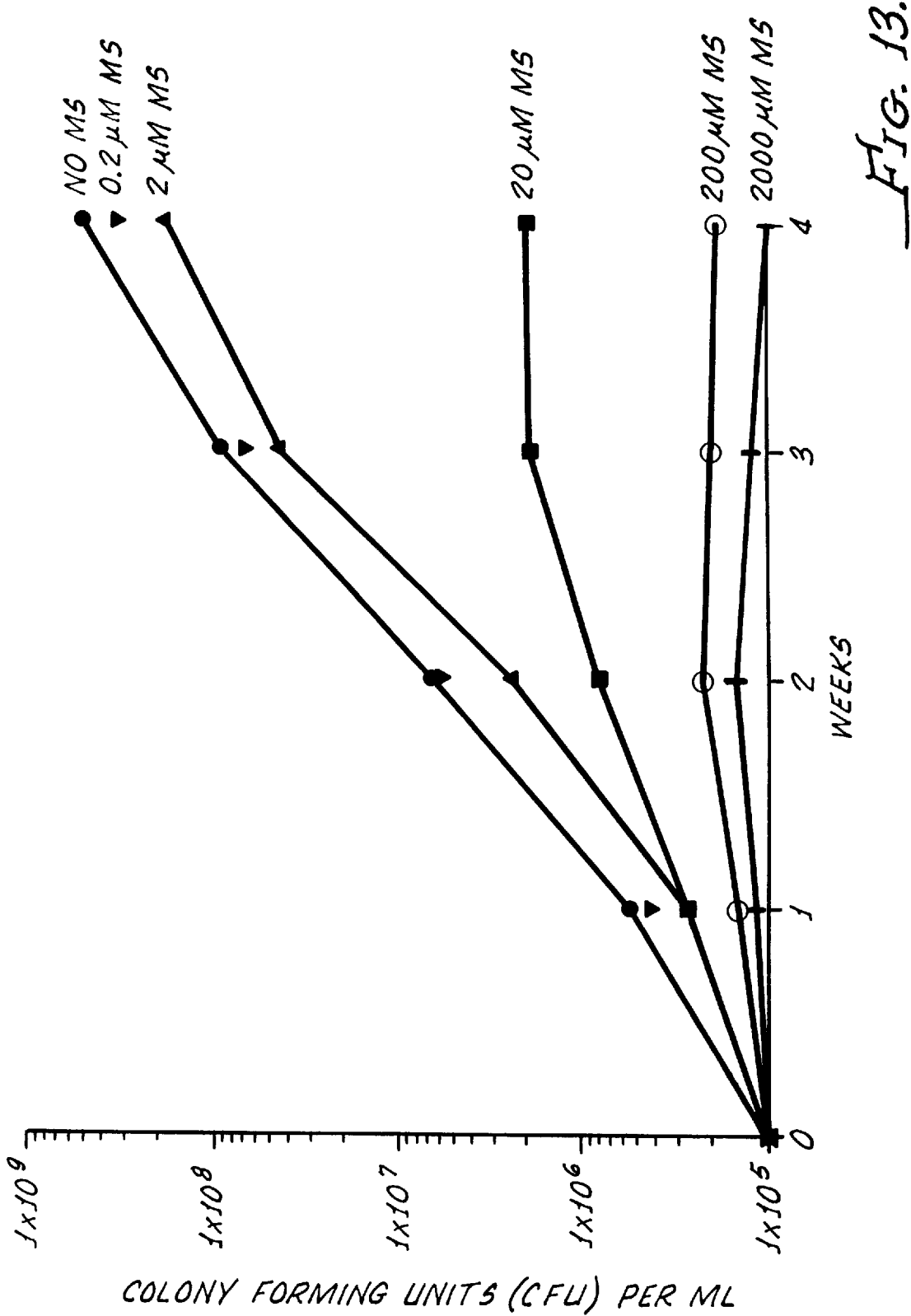
FIG. 13 is a graphical comparison of the effect upon *M. tuberculosis* Erdman cell growth of DL-methionine-SR-sulfoximine added to broth cultures at various concentrations.

L-methionine-S-sulfoximine has been identified as the diastereomer which inhibits glutamine synthetase (Manning, J. M., Moore, S., Rowe, W. B., and Meister, A., 1969 Biochemistry 8:2681–2685). DL-methionine-SR-sulfoximine, containing all 4 racemic configurations of the molecule, is about ¼ as potent in inhibiting the growth of *M. tuberculosis* as L-methionine-S-sulfoximine. This can be seen by a comparison of the growth-inhibiting properties of L-methionine-S-sulfoximine, shown in FIG. 4, and those of the racemic DL-methionine-SR-sulfoximine, shown in FIG. 13. This suggests that the antimicrobial effect against *M. tuberculosis* is due to the capacity of the diastereomer L-methionine-S-sulfoximine to inhibit glutamine synthetase.

To further demonstrate the mechanism of operation of the exemplary embodiment of the present invention previously discussed, the following example illustrates that the capacity of MS to inhibit *M. tuberculosis* growth is reversed by L-glutamine.

EXAMPLE 13

Figure 14:
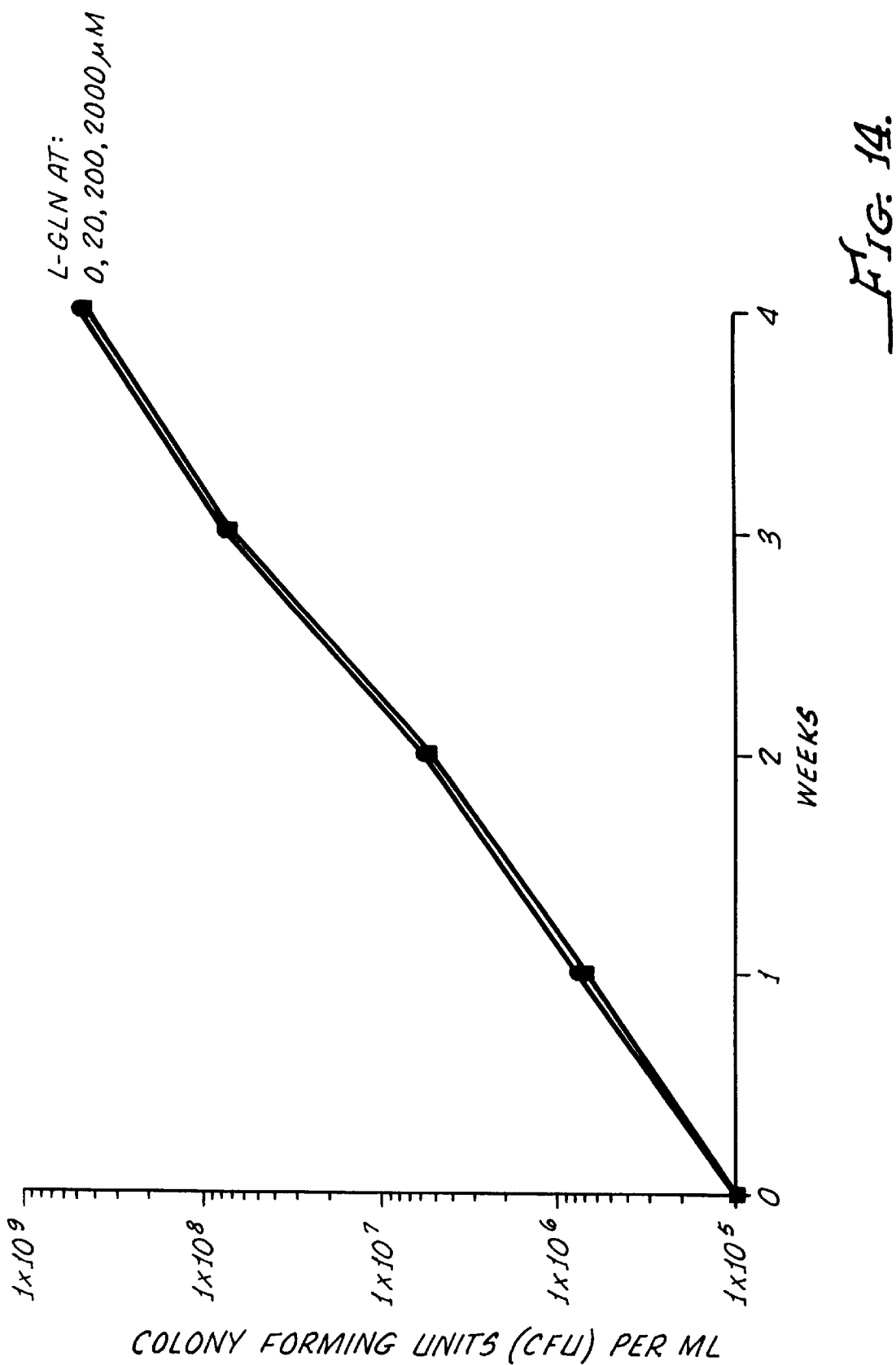
FIG. 14 is a graphical depiction of the lack of effect upon *M. tuberculosis* Erdman cell growth of the addition of L-glutamine to broth cultures in the absence of L-methionine-S-sulfoximine.
Figure 15:
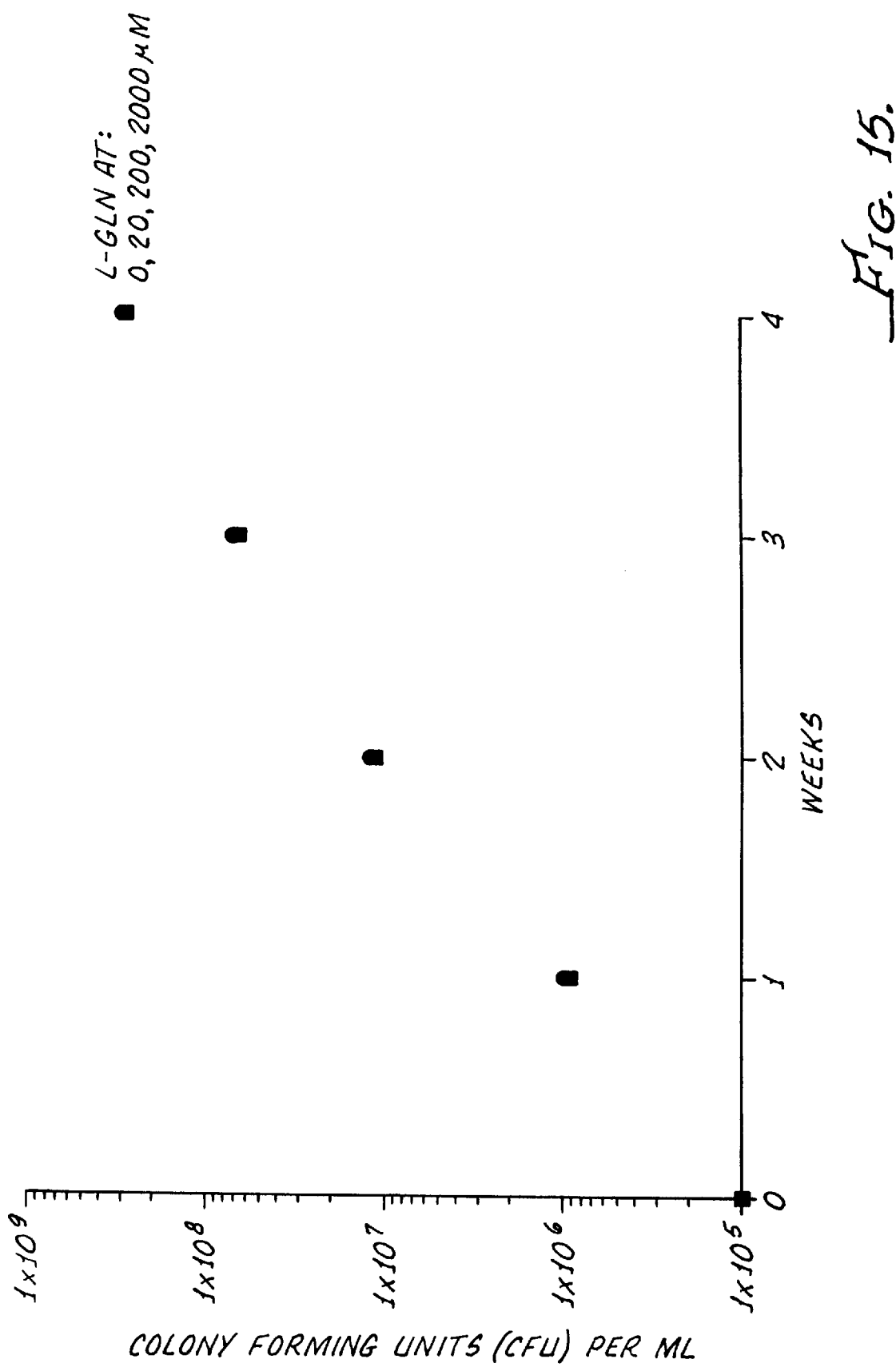
FIG. 15 is a graphical depiction of the lack of effect upon *M. tuberculosis* Erdman cultures of the addition of L-glutamine in the presence of a minimally inhibitory concentration of L-methionine-S-sulfoximine.
Figure 16:
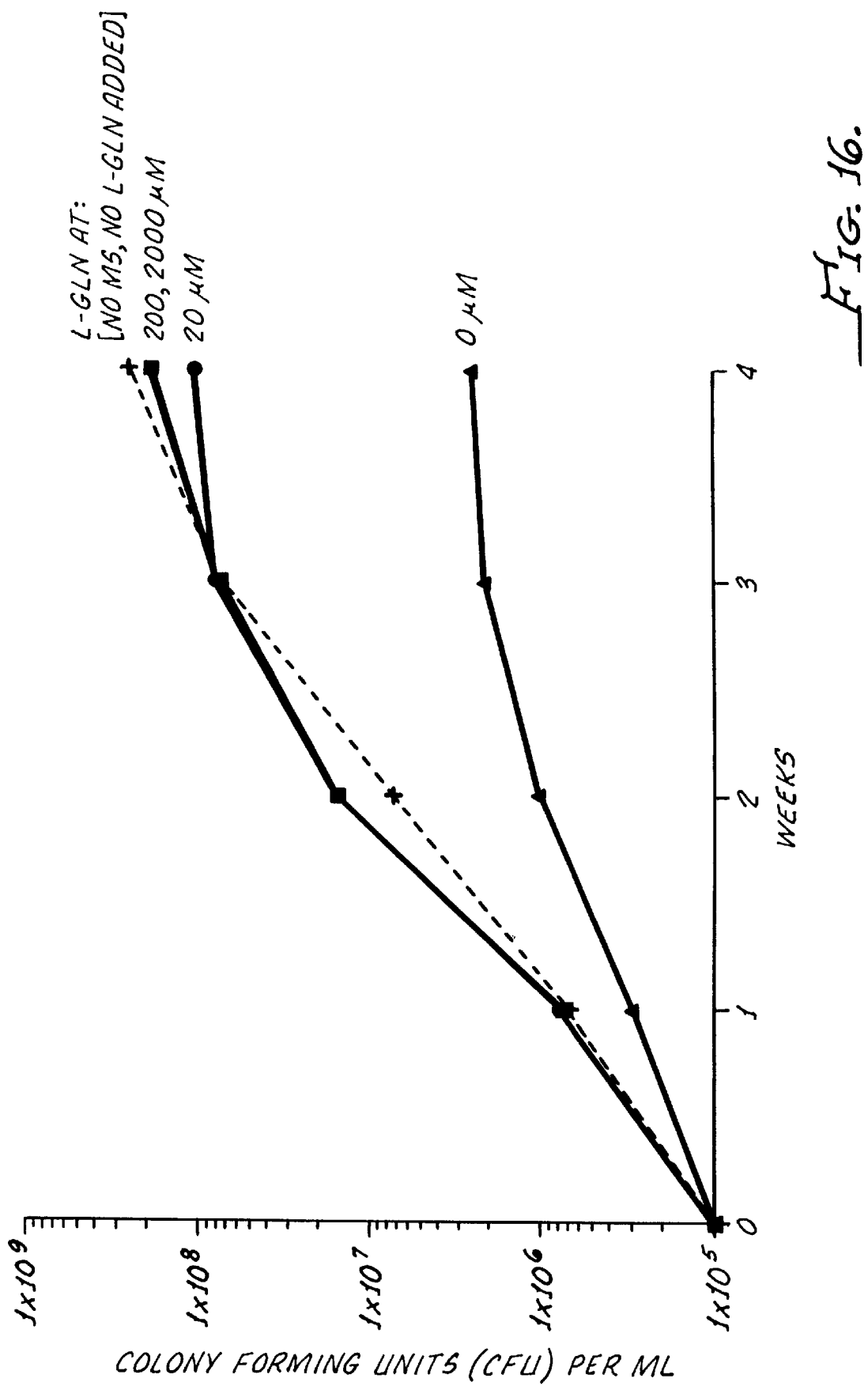
FIG. 16 is a graphical comparison of the effect upon *M. tuberculosis* Erdman cell growth of the addition of L-glutamine to broth cultures in the presence of an inhibitory concentration of 2 µM L-methionine-S-sulfoximine.
Figure 17:
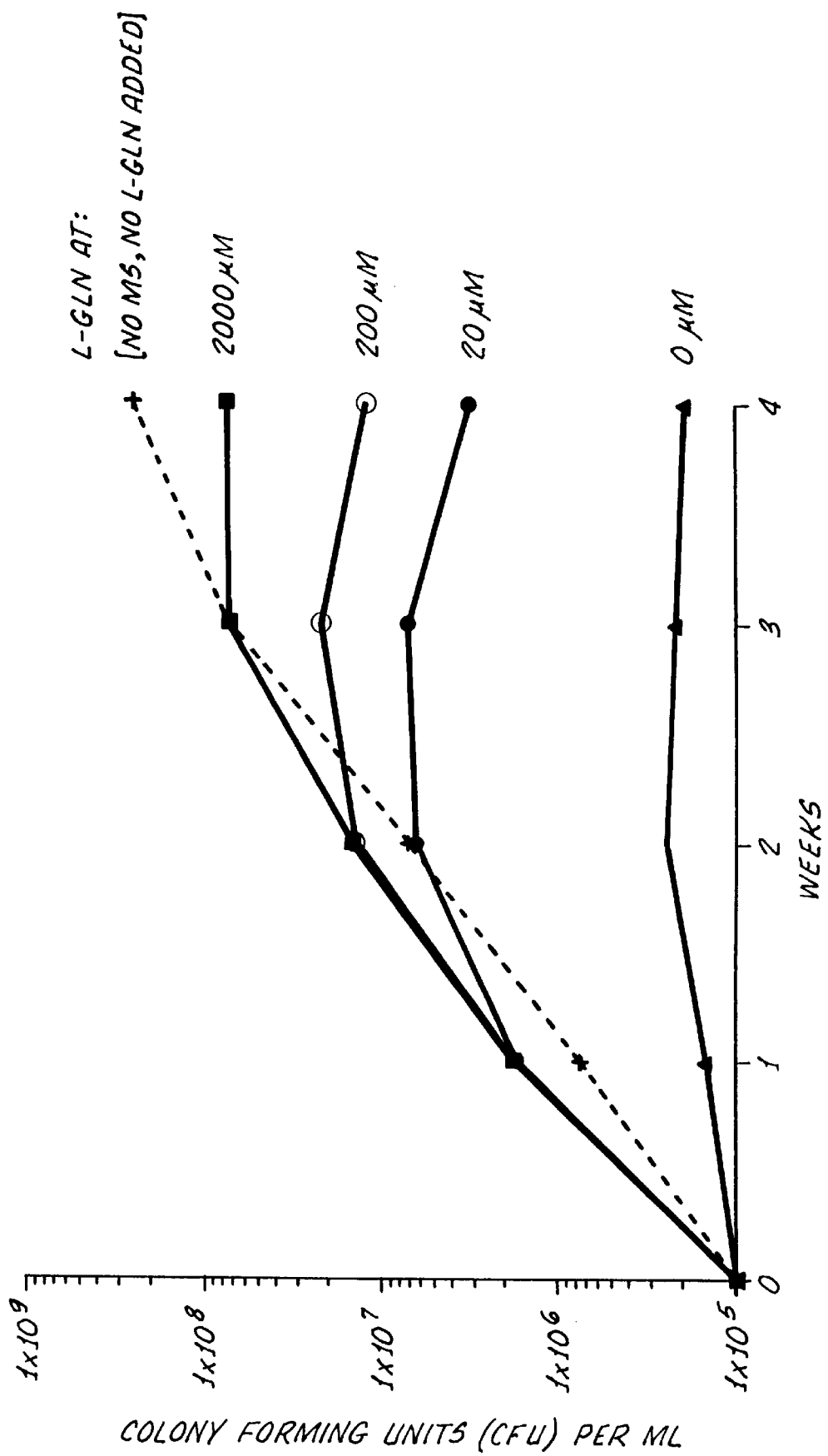
FIG. 17 is a graphical comparison of the effect upon *M. tuberculosis* Erdman cell growth of the addition of L-glutamine to broth cultures in the presence of an inhibitory concentration of 20 µM L-methionine-s-sulfoximine.
Figure 18:
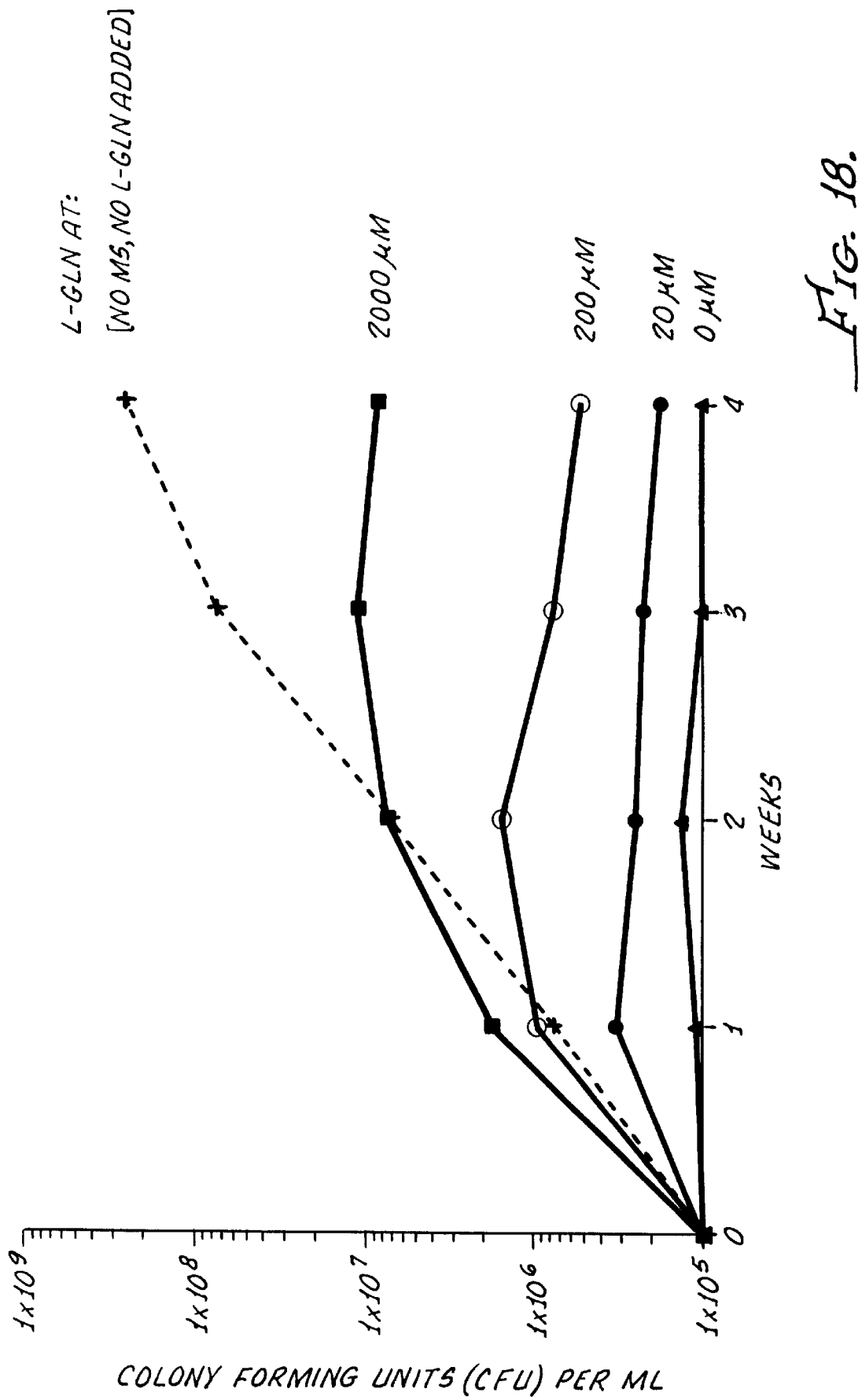
FIG. 18 is a graphical comparison of the effect upon *M. tuberculosis* Erdman cell growth of the addition of L-glutamine to broth cultures in the presence of an inhibitory concentration of 200 µM L-methionine-S-sulfoximine.

L-glutamine (L-GLN) was added to MS-treated cultures of *M. tuberculosis* Erdman. As shown in FIGS. 14–18, the addition of L-glutamine reversed the inhibitory effect of MS on *M. tuberculosis* cultures (FIGS. 16, 17, and 18). In contrast, addition of L-GLN had no effect on the growth of *M. tuberculosis* cultures not treated with MS or cultures treated with subinhibitory concentrations of MS (FIGS. 14 and 15).

To demonstrate the ability of the present invention to effectively treat disease conditions without harming the infected host, the following example illustrates that L-methionine-S-sulfoximine does not inhibit the growth of a human monocyte cell line.

EXAMPLE 14

Figure 19:
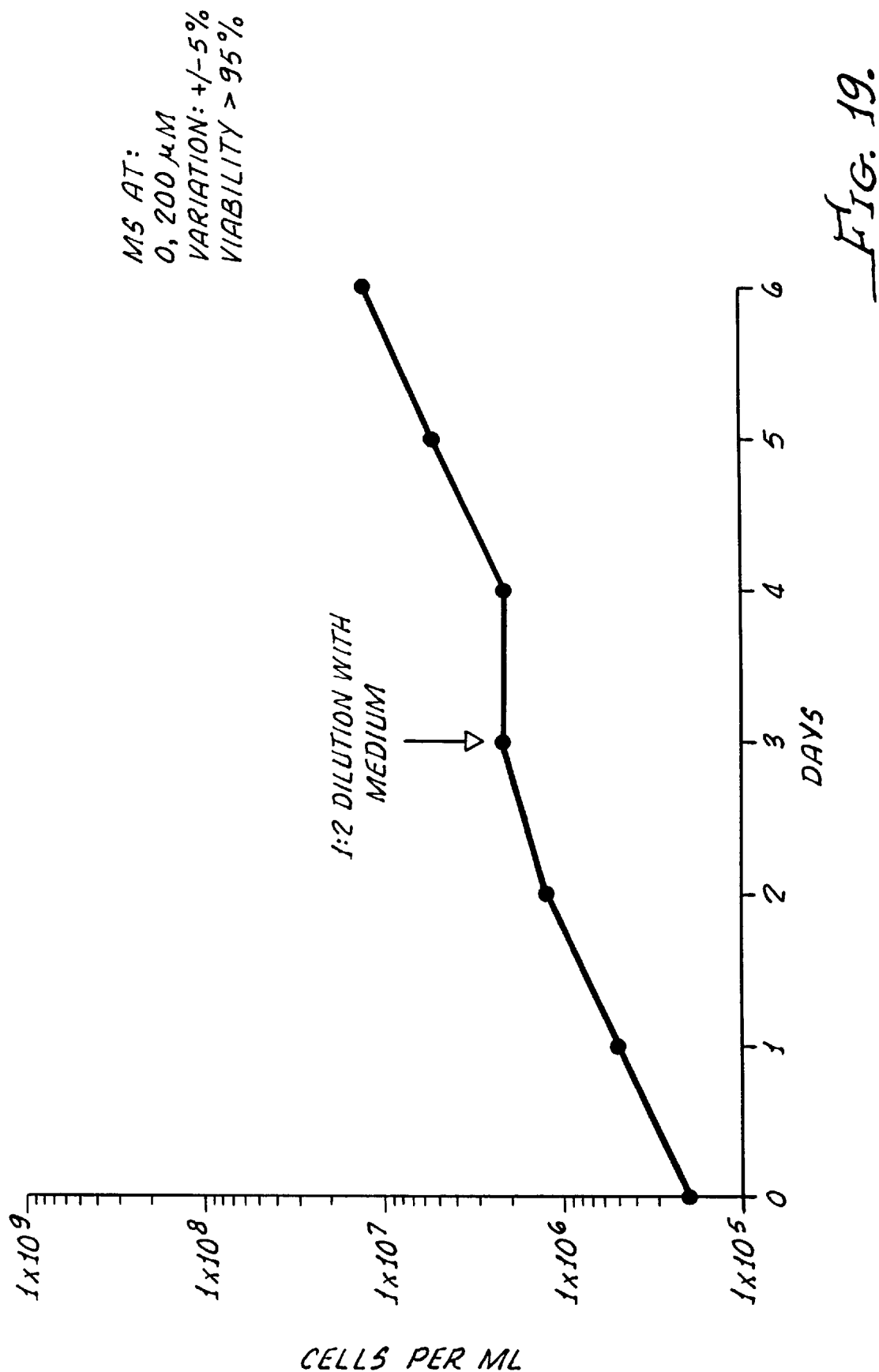
FIG. 19 is a graphical depiction of the lack of effect upon THP-1 human monocyte cell growth of the addition of L-methionine-S-sulfoximine at a concentration of 200 µM.
Figure 20:
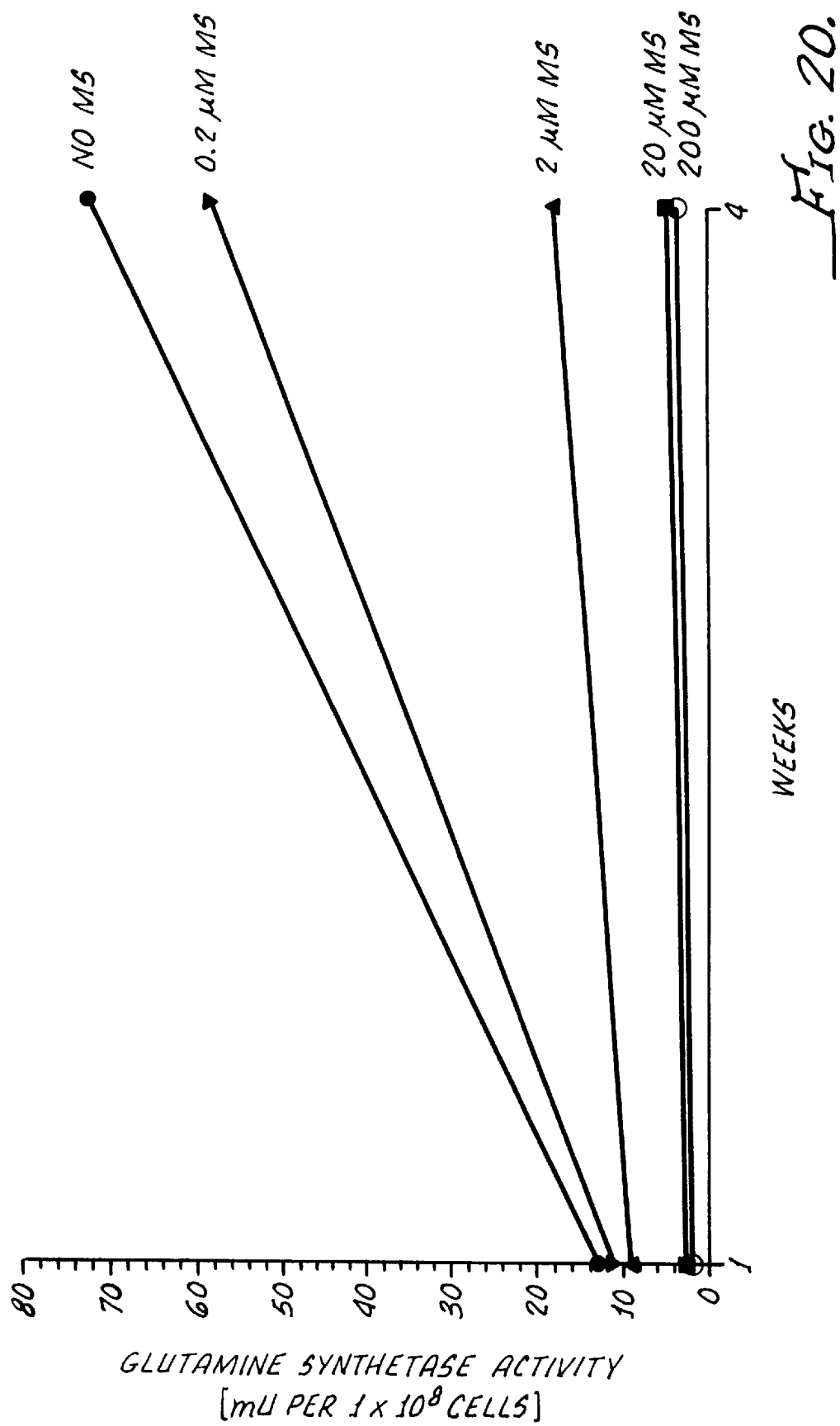
FIG. 20 is a graphical comparison of the effect upon extracellular glutamine synthetase activity of various concentrations of L-methionine-S-sulfoximine in *M. tuberculosis* broth cultures.

The influence of MS at 200 μM on the growth of a human monocyte cell line (THP-1 cells) was determined by assay. As shown in FIG. 19, MS had no influence on the growth rate of these cells, which demonstrates that MS showed no evidence of toxicity against THP-1 cells in this assay.

To directly demonstrate the efficacy of the present invention in treating diseased conditions associated with infection by an intracellular pathogen, the following example illustrates the inhibition by MS of the growth of *M. tuberculosis* cells present intracellularly in human cells.

EXAMPLE 15

The capacity of MS to inhibit growth of intracellular *M. tuberculosis* in a human monocyte cell line, THP-1 cells (ATCC TIB 202), was demonstrated as follows:

It was first established that MS has no evident toxicity for THP-1 cells up to a concentration of 200 μM. As shown in FIG. 19, THP-1 cells cultured in the presence of 0 or 200 μM MS grew at the same rate and maintained high viability.

To determine the effect of MS on intracellular *M. tuberculosis*, THP-1 cells were seeded at a cell density of $1 \times 10^7$ cells per T75 culture flask in 10 ml RPMI 1640 medium supplemented with heat-inactivated fetal calf serum. Phorbol-12-myristate-13-acetate was added at a concentration of 100 nM to promote adherence of the cells to the culture flasks over a three-day incubation period at 37° C. and 5% $CO_2$/95% air. The THP-1 cell monolayer was then infected by culturing it at a multiplicity of infection of 1 with *M. tuberculosis* Erdman that had been grown for 8 days on 7H11 agar at 37° C. and 5% $CO_2$/95% air. After 90 minutes, non-adherent bacteria were washed away and the infected cells were incubated for up to five days. At three hours, two days, and five days, the cell cultures were harvested and the monocytes were lysed by the addition of 0.1% sodium dodecyl sulfate or by vortexing. Serial dilutions of released mycobacteria were then plated on 7H11 agar and CFU were counted after two weeks at 37° C. and 5% $CO_2$/95% air.

Figure 24:
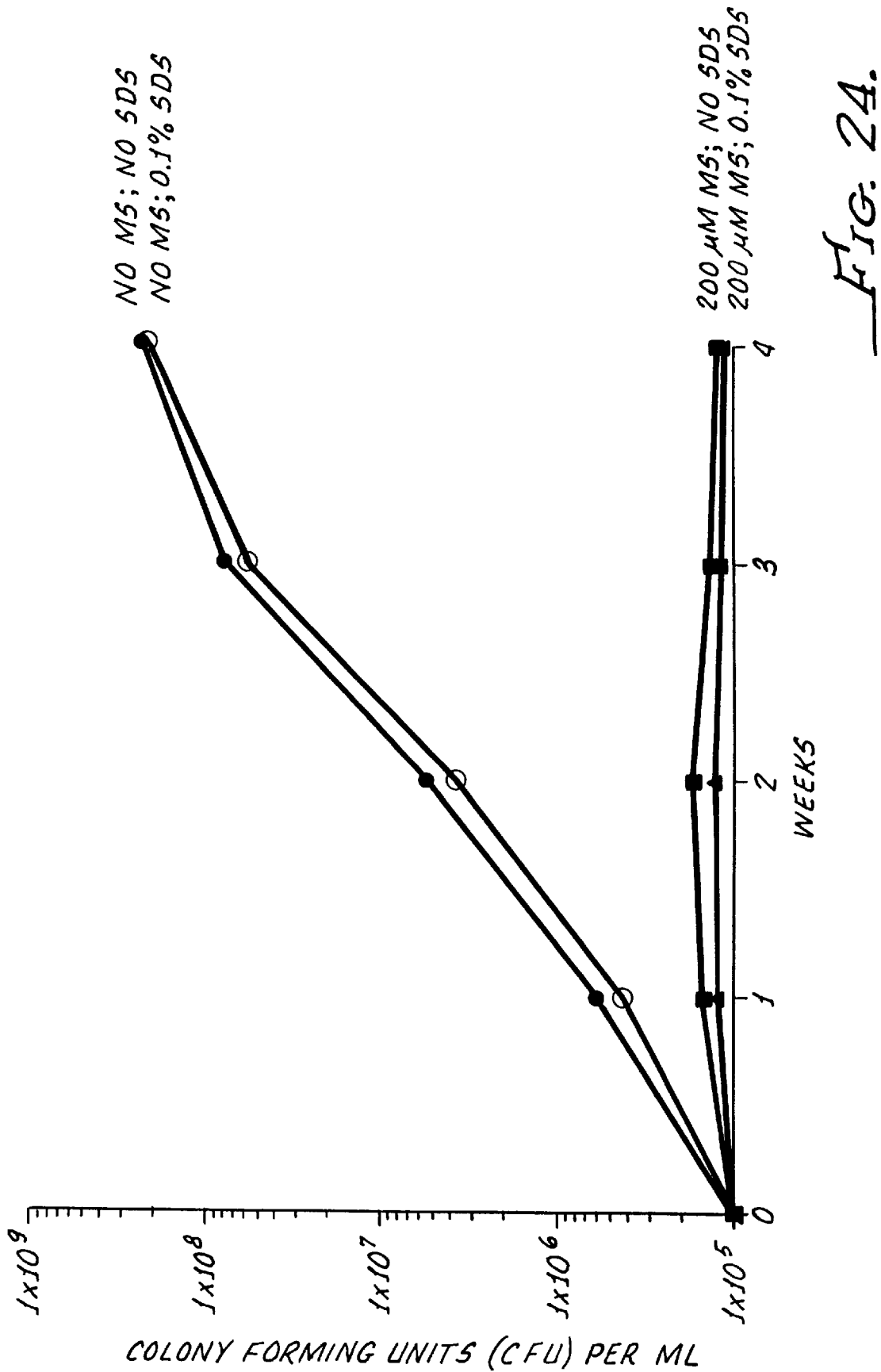
FIG. 24 is a graphical comparison of the effect upon *M. tuberculosis* Erdman cell growth of the addition of L-methionine-S-sulfoximine and/or sodium dodecyl sulfate to broth cultures.

Table 1 shows the number of colony-forming units in infected monocytes in the presence or absence of MS. In the presence of 200 μM MS, *M. tuberculosis* growth was inhibited by almost 1 log by two days and by nearly 2 logs by five days. Control experiments showed that the addition of 0.1% SDS, used to lyse THP-1 cells and release intracellular bacteria, had no influence on growth of *M. tuberculosis* in broth culture (FIG. 24). Moreover, lysing THP-1 cells by adding 0.1% SDS or by vortexing yielded similar results (Table 1, Day 5a vs. Day 5b).

TABLE 1

Effect of L-methionine-S-sulfoximine on *M. tuberculosis* cells present intracellularly in human cells
Colony forming units of *M. tuberculosis* Erdman from infected THP-1 human monocytes

| Day | No L-methionine-S-sulfoximine CFU | 200 μM L-methionine-S-sulfoximine CFU |
|---|---|---|
| 0 | $7.85 \times 10^5$ | $8.58 \times 10^5$ |
| 2 | $4.32 \times 10^6$ | $6.22 \times 10^5$ |
| 5a[1] | $4.74 \times 10^7$ | $4.80 \times 10^5$ |
| 5b[2] | $4.22 \times 10^7$ | $4.32 \times 10^5$ |

[1]Cells lysed with sodium dodecyl sulfate.
[2]Cells lysed by vortexing.

The foregoing examples demonstrate the efficacy of the present invention as illustrated by MS, an exemplary antibiotic for use against *M. tuberculosis* cells which are present intracellularly in human macrophages. In accordance with the teachings of the present invention, methods and associated antibiotics which are useful against other intracellular pathogens can be provided by identifying and targeting other extracellular proteins produced by the pathogens of interest, as many extracellular proteins possess enzymatic activity. Compounds which inhibit such extracellular enzymatic activity necessary for the growth or survival of the pathogen can be used as antibiotic agents for the pathogenic organisms which express the protein in question.

An alternative method for interfering with or inhibiting the functional activity of the identified extracellular cellular enzyme is to block or prevent the production of the enzyme itself. Thus, in accordance with the teachings of the present invention, antisense oligodeoxynucleotides (ODN) can be used for this purpose.

The following example illustrates the provision of antisense oligodeoxynucleotides which interfere with the expression of and have the functional activity of *M. tuberculosis* extracellular glutamine synthetase.

EXAMPLE 16

The DNA sequence encoding *M. tuberculosis* glutamine synthetase was determined for both DNA strands. The open reading frame encompasses 1,434 nucleotides, equal to 478 codons or amino acids. The calculated molecular mass for one of the 12 glutamine synthetase subunits is 53.6 KD; the subunit's apparent molecular weight is ~56–58 KD, as judged by denaturing polyacrylamide gel electrophoresis. The difference is believed to be due to the presence of 0 to 12 AMP modifications per complete glutamine synthetase molecule as native glutamine synthetase is a heterogeneous mix of enzymes, each modified to a different degree by the addition of AMP residues for which there is one acceptor amino acid per subunit.

The DNA sequences flanking the glutamine synthetase gene for both DNA strains were determined by sequencing ~1,200 bp for the upstream region and ~600 bp for the downstream region. No leader sequence could be identified in the vicinity of the initiator codon GTG. Both the intracellular and extracellular glutamine synthetase yielded the same N-terminal amino acid sequence, suggesting the absence of a specific leader sequence.

Large clones carrying genes in the flanking region of the glutamine synthetase gene were isolated and from them two related genes, glnE encoding the adenylyl transferase and GSII, putatively glutamine synthetase II, downstream of the glutamine synthetase gene, were identified. The sequences of these genes are as follows:

```
glnE-GENE [1 to 2985] → 1-phase Translation

DNA sequence 2985 b.p. gtgGTCGTGAQCC ... TTCGGGAGTtga linear

1/1                                     31/11
gtg GTC GTG ACC AAA CTC GCC ACG CAG CGG CCG AAG TTG CCC AGC GTT GGC CGG CTC GGA  (Sequence ID No. 18)
val val val thr lys len ala thr gln arg pro lys len pro ser val gly arg leu gly 61/21                                   91/31
TTA GTT GAC CCC CCT GCT GGT GAG CGT CTG GCT CAG GTG GGG TGG GAT CGG CAC GAG GAT
leu val asp pro pro ala gly gln arg leu ala gln leu gly trp asp arg his glu asp 121/41                                  151/51
CAG GCG CAC GTC GAC CTG CTG TGG TCG CTG TCA CGC GCT CCG GAC GCC GAT GCC GCG CTG
gln ala his val asp leu leu trp ser leu ser arg ala pro asp ala asp ala ala leu 181/61                                  211/71
CGC GCC TTG ATC CGG CTG TCG GAG AAT CCA GAC ACC GGA TGG GAC GAG CTC AAC GCG GCT
arg ala leu ile arg leu ser glu asn pro asp thr gly trp asp glu leu asn ala ala 241/81                                  271/91
CTG CTG CGC GAA CGC AGT CTG CGC GGG CGG CTG TTC TCG GTG CTG GGC TCG TCG CTG GCG
leu leu arg glu arg ser leu arg gly arg leu phe ser val leu gly ser ser leu ala 301/101                                 331/111
TTG GGC GAT CAC CTG GTC GCC CAT CCG CAG TCC TGG AAA TTG CTG CGG GGC AAG GTC ACA
leu gly asp his leu val ala his pro gln ser trp lys leu leu arg gly lys val thr 361/121                                 391/131
CTG CCG TCC CAT GAC CAG CTG CAG CGG TCG TTC GTC GAG TGC GTC GAG GAA TCG GAG GGT
leu pro ser his asp gln leu gln arg ser phe val glu cys val glu glu ser glu gly 421/141                                 451/151
ATG CCG GGC TCG CTC GTG CAC CGA TTG CGA ACC CAG TAC CGC GAC TAC GTG CTA ATG CTG
met pro gly ser leu val his arg leu arg thr gln tyr arg asp tyr val leu met leu
```

```
481/161                                     511/171
GCC GCT CTC GAC CTG GCC GCG ACG GTC GAG     GAC GAA CCG GTG CTG CCA TTC ACC GTG GTG
ala ala leu asp leu ala ala thr val glu     asp glu pro val leu pro phe thr val val 541/181                                     571/191
GCC GCA CGC CTG GCG GAC GCC GCG GAC GCC     GCT CTG GCG GCG GCG CTG CGC GTG GCC GAG
ala ala arg leu ala asp ala ala asp ala     ala leu ala ala ala leu arg val ala glu 601/201                                     631/211
GCG AGC GTG TGC GGC GAG CAC CCG CCA CCG     CGC CTG GCG GTC ATC GCG ATG GGC AAG TGC
ala ser val cys gly glu his pro pro pro     arg leu ala val ile ala met gly lys cys 661/221                                     691/231
GGT GCG CGC GAA CTG AAC TAC GTC AGC GAC     GTC GAT GTC ATA TTC GTT GCC GAG CGC TCC
gly ala arg glu leu asn tyr val ser asp     val asp val ile phe val ala glu arg ser 721/241                                     751/251
GAC CCG CGC AAC GCG CGC GTG GCC AGC GAG     ATG ATG CGG GTG GCC TCG GCG GCC TTT TTC
asp pro arg asn ala arg val ala ser glu     met met arg val ala ser ala ala phe phe 781/261                                     811/271
GAG GTG GAC GCC GCC CTG CGT CCG GAG GGG     CGC AAC GGG GAG CTG GTC CGT ACG CTC GAG
glu val asp ala ala leu arg pro glu gly     arg asn gly glu leu val arg thr leu glu 841/281                                     871/291
TCG CAC ATC GCC TAC TAC CAG CGC TGG GCC     AAG ACC TGG GAG TTT CAG GCG TTG CTG AAA
ser his ile ala tyr tyr gln arg trp ala     lys thr trp glu phe gln ala leu leu lys 901/301                                     931/311
GCA CGG CCA GTC GTT GGC GAC GCG GAA CTT     GGC GAG CGT TAC CTG ACC GCC TTG ATG CCG
ala arg pro val val gly asp ala glu leu     gly glu arg tyr leu thr ala leu met pro 961/321                                     991/331
ATG GTG TGG CGA GCC TGC GAG CGC GAA GAC     TTT GTG GTC GAG GTG CAG GCC ATG CGG CGG
met val trp arg ala cys glu arg glu asp     phe val val glu val gln ala met arg arg 1021/341                                    1051/351
CGG GTG GAG CAG CTG GTG CCC GCC GAT GTC     CGC GGC CGC GAG CTC AAA CTC GGC AGC GGC
arg val glu gln leu val pro ala asp val     arg gly arg glu leu lys leu gly ser gly 1081/361                                    1111/371
GGA TTG CGC GAC GTG GAG TTC GCC GTA CAG     CTA CTG CAG CTG GTT CAT GCC CGT AGC GAC
gly leu arg asp val glu phe ala val gln     leu leu gln leu val his ala arg ser asp 1141/381                                    1171/391
GAG TCG TTA CGG GTG GCG TCC ACG GTG GAC     GCA TTG GCG GCG TTG GGC GAA GGC GGC TAC
glu ser leu arg val ala ser thr val asp     ala leu ala ala leu gly glu gly gly tyr 1201/401                                    1231/411
ATC GGG CGT GAG GAC GCG GCG AAC ATG ACC     GCG TCG TAT GAG TTC CTC AGG CTG CTC GAG
ile gly arg glu asp ala ala asn met thr     ala ser tyr glu phe leu arg leu leu glu 1261/421                                    1291/431
CAC CGA CTG CAG TTG CAG CGG CTC AAG CGC     ACC CAC CTG CTT CCC GAT CCC GAA GAC GAG
his arg leu gln leu gln arg leu lys arg     thr his leu leu pro asp pro glu asp glu 1321/441                                    1351/451
GAG GCA GTG CGC TGG CTG GCG CGC GCG GCC     CAC ATC CGG CCC GAT GGC CGA AAC GAT GCG
glu ala val arg trp leu ala arg ala ala     his ile arg pro asp gly arg asn asp ala 1381/461                                    1411/471
GCC GGG GTG CTG CGG GAG GAA CTC AAG AAG     CAG AAC GTG CGG GTG TCG AAG TTA CAC ACC
ala gly val leu arg glu glu leu lys lys     gln asn val arg val ser lys leu his thr 1441/481                                    1471/491
AAA CTC TTC TAT CAA CCG CTG CTG GAA TCG     ATC GGC CCG ACC GGG TTG GAG ATC GCC CAC
lys leu phe tyr gln pro leu leu glu ser     ile gly pro thr gly leu glu ile ala his 1501/501                                    1531/511
GGC ATG ACG TTG GAG GCC GCG GGG CGC CGG     CTG GCC GCG CTG GGC TAC GAG GGA CCG CAG
gly met thr leu glu ala ala gly arg arg     leu ala ala leu gly tyr glu gly pro gln 1561/521                                    1591/531
ACC GCG TTG AAA CAC ATG TCG GCG TTG GTC     AAT CAA AGC GGC CGG CGC GGA CGG GTG CAG
thr ala leu lys his met ser ala leu val     asn gln ser gly arg arg gly arg val gln 1621/541                                    1651/551
TCG GTG CTG CTG CCC AGG CTG CTG GAC TGG     ATG TCG TAT GCC CCC GAT CCC GAC GGC GGA
ser val leu leu pro arg leu leu asp trp     met ser tyr ala pro asp pro asp gly gly
```

-continued

```
1681/561                                1711/571
CTG CTG GCC TAC CGG CGG CTC AGT GAG GCG CTG GCC ACC GAA AGC TGG TAC CTG GCC ACG
leu leu ala tyr arg arg leu ser glu ala leu ala thr glu ser trp tyr leu ala thr 1741/581                                1771/591
CTG CGG GAC AAG CCC GCG GTG GCC AAG CGG CTC ATG CAT GTC TTG GGT ACC TCG GCG TAT
leu arg asp lys pro ala val ala lys arg leu met his val leu gly thr ser ala tyr 1801/601                                1831/611
GTG CCG GAT CTG TTG ATG CGC GCG CCG CGG GTC ATC CAG CAG TAC GAG GAC GGG CCT GCG
val pro asp leu leu met arg ala pro arg val ile gln gln tyr glu asp gly pro ala 1861/621                                1891/631
GGC CCG AAG CTG CTC GAG ACC GAG CCC GCC GCC GTG GCT CGG GCG CTG ATC GCC TCG GCG
gly pro lys leu leu glu thr glu pro ala ala val ala arg ala leu ile ala ser ala 1921/641                                1951/651
AGC CGC TAC CCC GAC CCG GAG CGG GCC ATC GCC GGC GCG CGC ACG CTG CGT CGT CGA GAG
ser arg tyr pro asp pro glu arg ala ile ala gly ala arg thr leu arg arg arg glu 1981/661                                2011/671
CTG GCC CGC ATC GGT TCG GCG GAC CTG CTC GGC CTG CTC GAG GTC ACC GAG GTG TGC CGG
leu ala arg ile gly ser ala asp leu leu gly leu leu glu val thr glu val cys arg 2041/681                                2071/691
GCG TTG ACG TCG GTG TGG GTG GCG GTG CTG CAG GCC GCG CTG GAC GTC ATG ATC CGG GCC
ala leu thr ser val trp val ala val leu gln ala ala leu asp val met ile arg ala 2101/701                                2131/711
AGC CTT CCC GAC GAC GAT CGC GCC CCG GCG GCC ATC GCG GTC ATC GGC ATG GGT CGG CTG
ser leu pro asp asp asp arg ala pro ala ala ile ala val ile gly met gly arg leu 2161/721                                2191/731
GGT GGT GCC GAG TTG GGC TAC GGG TCG GAT GCC GAC GTG ATG TTC GTC TGT GAG CCG GCC
gly gly ala glu leu gly tur gly ser asp ala asp val met phe val cys glu pro ala 2221/741                                2251/751
ACC GGC GTC GAC GAT GCA CGG GCG GTG AAA TGG TCG ACA TCG ATC GCC GAG CGG GTT CGG
thr gly val asp asp ala arg ala val lys trp ser thr ser ile ala glu arg val arg 2281/761                                2311/771
GCG CTG CTG GGG ACA CCC AGC GTC GAT CCG CCG CTC GAG CTC GAC GCC AAT TTG CGA CCC
ala leu leu gly thr pro ser val asp pro pro leu glu leu asp ala asn leu arg pro 2341/781                                2371/791
GAG GGC CGC AAC GGT CCG CTG GTC CGC ACC CTG GGG TCC TAC GCC GCA TAC TAC GAG CAG
glu gly arg asn gly pro leu val arg thr leu gly ser tyr ala ala tyr tyr glu gln 2401/801                                2431/811
TGG GCA CAG CCA TGG GAG ATC CAG GCC CTG CTA CGC GCA CAC GCG GTT GCC GGC GAT GCC
trp ala gln pro trp glu ile gln ala leu leu arg ala his ala val ala gly asp ala 2461/821                                2491/831
GAG TTG GGT CAG CGA TTC CTA CGG ATG GTC GAC AAA ACG CGG TAT CCG CCC GAC GGT GTG
glu leu gly gln arg phe leu arg met val asp lys thr arg tyr pro pro asp gly val 2521/841                                2551/851
TCC GCT GAC TCG GTG CGC GAG ATT CGC CGC ATC AAG GCC CGT ATC GAG TCC GAG CGG TTG
ser ala asp ser val arg glu ile arg arg ile lys ala arg ile glu ser glu arg leu 2581/861                                2611/871
CCG CGC GGT GCC GAC CCC AAC ACA CAC ACC AAA CTG GGC CGC GGC GGA CTG GCC GAC ATC
pro arg gly ala asp pro asn thr his thr lys leu gly arg gly gly leu ala asp ile 2641/881                                2671/891
GAA TGG ACC GTG CAG TTG CTG CAG CTA CAG CAT GCG CAC CAG GTT CCC GCC CTG CAC AAC
glu trp thr val gln leu leu gln leu gln his ala his gln val pro ala leu his asn 2701/901                                2731/911
ACC TCG ACG CTG CAA TCC CTG GAT GTC ATC GCG GCC GCC GAT CTG GTT CCC GCA GCC GAC
thr ser thr leu gln ser leu asp val ile ala ala ala asp leu val pro ala ala asp 2761/921                                2791/931
GTG GAG CTG CTC CGT CAG GCC TGG CTG ACC GCC ACC CGG GCC CGC AAC GCG CTG GTG TTG
val glu leu leu arg gln ala trp leu thr ala thr arg ala arg asn ala leu val leu 2821/941                                2851/951
GTG CGC GGC AAG CCC ACC GAC CAG CTG CCG GGA CCC GGG CGC CAG CTC AAT GCG GTC GCG
val arg gly lys pro thr asp gln leu pro gly pro gly arg gln leu asn ala val ala

2881/961                                2911/971
```

-continued

```
GTC GCG GCC GGC TGG CGA AAC GAC GAC GGT GGG GAA TTC CTG GAC AAC TAC CTA CGG GTG
val ala ala gly trp arg asn asp asp gly gly glu phe leu asp asn tyr leu arg val 2941/981                            2971/991
ACG CGG CGG GCA AAG GCG GTA GTG CGC AAA GTG TTC GGG AGT tga
thr arg arg ala lys ala val val arg lys val phe gly ser OPA MTB GS II GENE [1 to 1341] → 1-phase Translation DNA sequence 1341 b.p. atgGACCGACAG ... CTGTCGTGtag linear 1/1                                 31/11
atg GAC CGA CAG AAG GAA TTC GTT CTT CGT ACC CTG GAA GAA CGC GAC ATC CGC TTC GTC    (Sequence ID No. 19)
Met asp arg gln lys glu phe val leu arg thr leu glu glu arg asp ile arg phe val 61/21                               91/31
CGG CTG TGG TTC ACA GAC GTG CTC GGT TTC CTC AAG TCG GTC GCC ATC GCC CCA GCC GAA
arg leu trp phe thr asp val leu gly phe leu lys ser val ala ile ala pro ala glu 121/41                              151/51
CTC GAG GGC GCC TTC GAG GAA GGC ATC GGC TTC GAC GGA TCC TCG ATC GAG GGC TTT GCG
leu glu gly ala phe glu glu gly ile gly phe asp gly ser ser ile glu gly phe ala 181/61                              211/71
CGG GTC TCG GAA TCC GAT ACG GTG GCG CAC CCG GAC CCG TCG ACC TTC CAG GTG CTG CCC
arg val ser glu ser asp thr val ala his pro asp pro ser thr phe gln val leu pro 241/81                              271/91
TGG GCC ACC AGT TCC GGC CAC CAC CAC TCA GCG CGG ATG TTT TGC GAC ATC ACC ATG CCG
trp ala thr ser ser gly his his his ser ala arg met phe cys asp ile thr met pro 301/101                             331/111
GAC GGC TCG CCG TCG TGG GCG GAC CCG CGG CAC GTG TTG CGG CGG CAG CTG ACG AAG GCC
asp gly ser pro ser trp ala asp pro arg his val leu arg arg gln leu thr lys ala 361/121                             391/131
GGC GAA CTC GGC TTC TCC TGC TAC GTG CAT CCC GAA ATC GAG TTC TTC CTG CTC AAG CCC
gly glu leu gly phe ser cys tyr val his pro glu ile glu phe phe leu leu lys pro 421/141                             451/151
GGA CCC GAG GAC GGG TCG GTG CCC GTC CCG GTC GAC AAC GCC GGC TAT TTC GAC CAA GCG
gly pro glu asp gly ser val pro val pro val asp asn ala gly tyr phe asp gln ala 481/161                             511/171
GTG CAC GAC TCC GCC TTG AAC TTT CGC CGC CAC GCG ATC GAT GCC CTG GAA TTC ATG GGC
val his asp ser ala leu asn phe arg arg his ala ile asp ala leu glu phe met gly 541/181                             571/191
ATC TCG GTG GAG TTC AGC CAT CAC GAA GGC GCA CCC GGC CAG CAG GAG ATC GAC CTG CGG
ile ser val glu phe ser his his glu gly ala pro gly gln gln glu ile asp leu arg 601/201                             631/211
TTT GCC GAC GCT CTG TCG ATG GCT GAC AAC GTG ATG ACC TTC CGC TAC GTC ATC AAA GAA
phe ala asp ala leu ser met ala asp asn val met thr phe arg tyr val ile lys glu 661/221                             691/231
GTC GCG CTG GAA GAG GGC GCC CGG GCG TCG TTC ATG CCC AAG CCA TTC GGC CAG CAC CCG
val ala leu glu glu gly ala arg ala ser phe met pro lys pro phe gly gln his pro 721/241                             751/251
GGC TCG GCG ATG CAC ACC CAC ATG AGC CTG TTC GAG GGT GAT GTC AAC GCG TTC CAC AGC
gly ser ala met his thr his met ser leu phe glu gly asp val asn ala phe his ser 781/261                             811/271
GCT GAT GAT CCG CTG CAG CTG TCG GAA GTG GGT AAA TCG TTC ATC GCC GGG ATC CTG GAG
ala asp asp pro leu gln leu ser glu val gly lys ser phe ile ala gly ile leu glu 841/281                             871/291
CAC GCT TGC GAG ATC AGC GCG GTC ACA AAT CAG TGG GTC AAC TCT TAC AAG CGG CTG GTG
his ala cys glu ile ser ala val thr asn gln trp val asn ser tyr lys arg leu val 901/301                             931/311
CAG GGC GGC GAA GCG CCC ACG GCC GCG TCG TGG GGG GCC GCC AAC CGA TCC GCC CTA GTG
gln gly gly glu ala pro thr ala ala ser trp gly ala ala asn arg ser ala leu val 961/321                             991/331
CGG GTG CCG ATG TAC ACG CCG CAC AAG ACC TCG TCG CGG CGG GTC GAA GTA CGC AGC CCT
arg val pro met tyr thr pro his lys thr ser ser arg arg val glu val arg ser pro 1021/341                            1051/351
GAT TCG GCG TGC AAT CCC TAT CTG ACA TTC GCC GTG CTG CTG GCC GCG GGA TTG CGG GGT
```

-continued

```
asp ser ala cys asn pro tyr leu thr phe ala val leu leu ala ala gly leu arg gly 1081/361                                1111/371
GTA GAG AAG GGT TAC GTG CTG GGC CCG CAG CCC GAG GAC AAC GTA TGG GAC CTC ACA CCC
val glu lys gly tyr val leu gly pro gln ala glu asp asn val trp asp leu thr pro 1141/381                                1171/391
GAG GAA CGC CGA GCG ATG GGG TAC CGA GAA TTG CCG TCC AGT TTG GAT AGT GCG CTG CGC
glu glu arg arg ala met gly tyr arg glu leu pro ser ser leu asp ser ala leu arg 1201/401                                1231/411
GGC ATG GAG GCC TCC GAA CTC GTC GCG GAG GCC TTG GGG GAG CAC GTT TTT GAC TTT TTC
ala met glu ala ser glu leu val ala glu ala leu gly glu his val phe asp phe phe 1261/421                                1291/431
TTG CGC AAC AAG CGC ACG GAG TGG GCG AAC TAC CGC AGC CAC GTC ACG CCA TAC GAG CTG
leu arg asn lys arg thr glu trp ala asn tyr arg ser his val thr pro tyr glu leu 1321/441
CGC ACC TAC CTG TCG CTG tag
arg thr tyr leu ser leu AMB
```

Figure 25:
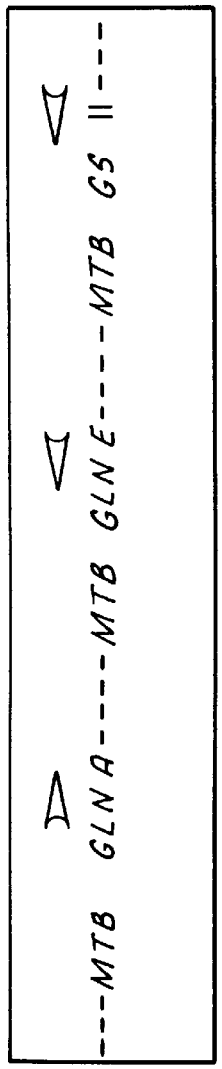
FIG. 25 is a diagram of the genomic arrangement of the *M. tuberculosis* gln genes cluster.
Figure 26:
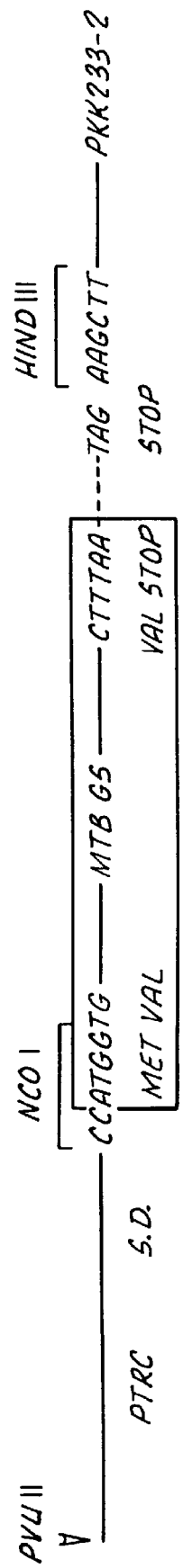
FIG. 26 is a diagram of a construct for expression of *M. tuberculosis* glutamine synthetase in *E. coli*.

Both genes are oriented in the opposite direction, compared with glutamine synthetase as shown in FIG. 25.

It is not clear whether or not the glutamine synthetase II gene encodes an active enzyme, because some of the domains that are highly conserved in many bacterial species are also present in glutamine synthetase II, while others are not. Whether the cloned M. tuberculosis glutamine synthetase gene is functional can be determined by transcomplementing a mutant strain of E. coli that lacks the glutamine synthetase cluster with *M. tuberculosis* glutamine synthetase. Uncomplemented, this mutant is strictly dependent on glutamine as a supplement in the growth medium.

The *M. tuberculosis* glutamine synthetase gene starts with a GTG codon, normally specifying valine. However, in *M. tuberculosis*, GTG is also frequently used as a start codon, specifying methionine which is removed from the mature protein. Any construct utilizing the GTG codon as an initiator methionine codon will not work in *E. coli*. However, fusing the entire glutamine synthetase structural gene including the initiator GTG codon in frame to the ATG codon downstream of the strong trc promotor and ribosome binding site of the "ATG vector" pKK233-2 (Amann, E. and Brosius, J., 1985, *Gene* 40:183–190) can be effective for this purpose.

As shown in FIG. 26, the 3' end of the *M. tuberculosis* glutamine synthetase construct contained the regular stop codon TAA, a second stop codon TAG located 8 codons downstream, and further downstream, a Hind III restriction site for cloning into the corresponding site on the pKK233-2 vector. The proper cloning of the glutamine synthetase gene can be confirmed by transforming this construct into *E. coli* YMC21E (Backman, K. C., Chen, Y. M., Ueno-Nishio, S., and Magasanik, B., 1983, J. Bacteriol. 154:516–519), ΔlacU169, endA, thi, hsdR, supE44, Δ(glnA-glnG) 2000, glnE::Tn5) and selecting for transcomplemented mutants by growing the culture in M9 medium supplemented with thiamine, kanamycin, ampicillin, and isopropyl β-D-thiogalactopyranoside (IPTG), but not glutamine.

Because YMC21E lacks the entire glutamine synthetase cluster, it depends strictly on glutamine as a supplement in this growth medium. Transformants that grew in M9 medium, therefore, expressed sufficient quantities of active *M. tuberculosis* glutamine synthetase driven from the IPTG inducible trc promoter on pKK 233-2 to transcomplement this glutamine synthetase deficient strain. Because the initiator methionine is removed from the newly synthesized polypeptide chain, no fusion protein is made. However, compared with the glutamine synthetase subunit in *M. tuberculosis*, the *E. coli* produced subunit is longer by one additional valine at the N terminus.

The culture medium can be examined for glutamine synthetase without finding any evidence that the *M. tuberculosis* glutamine synthetase is released in the culture medium by YMC21E as it is by *M. tuberculosis*. Confirmation that the glutamine synthetase gene insert was properly arranged can be obtained by isolating plasmid DNA from one recombinant *E. coli* and sequencing across the insert/vector junctions. Recombinant *E. coli* grow very slowly, probably because the *M. tuberculosis* glutamine synthetase is different from the wild-type *E. coli* enzyme with regard to its amino acid sequence, amino acid composition, size, three-dimensional structure, and interaction with other proteins such as chaperones and positive and negative regulators. Recombinant *E. coli* stably express the *M. tuberculosis* enzyme. That is, the recombinant *E. coli* can be subcultured several times with no change in genotypic and phenotypic markers.

Because an antisense oligodeoxynucleotide (ODN) must be selective for the gene encoding the enzyme of interest, the following example illustrates the selection of an appropriate target for an antisense ODN.

EXAMPLE 17

The sequence of the *M. tuberculosis* glutamine synthetase near the active site of the enzyme was aligned with that of human liver glutamine synthetase, as shown below: MTB:

```
5'-GGC GAC AAC GGG TCC GGC ATG CAC TGT CAT CAG TCG CTG TGG AAG-3'  (Sequence ID Nos. 20 and 21)

3'-CCG CTC TTG CCC AGG CCG TAC GTG ACA GTA GTC AGC GAC ACC TTC-5'
    G   D   N   G   S   G   M   H   C   H   Q   S   L   W   K

Human liver:
```

```
5'-AAC TGG AAT GGT GCA GGC TGC CAT ACC AAC TTC AGC ACC AAG GCC-3'   (Sequence ID Nos. 22 and 23)

3'-TTG ACC TTA CCA CGT CCG ACG GTA TGG TTG AAG TCG TGG TTC CGG-5'
     N   W   N   G   A   C   H   T   N   F   S   T   K   A
```

A stretch of nine amino acids immediately upstream of this active site domain (not shown) demonstrates alignment of the sequence of the *M. tuberculosis* glutamine synthetase and that of human liver glutamine synthetase. The bold H is critical to the function of the enzyme. If it is oxidized or proteolytically attacked, the enzyme is inactivated. The underlined amino acids are conserved in bacterial glutamine synthetase molecules.

The bold nucleotide sequence of the *M. tuberculosis* GS gene is utilized as an antisense ODN, since it overlaps the active site of the *M. tuberculosis* glutamine synthetase gene and can block expression of this gene and hence block its functional activity. On the other hand, it would not likely block the human glutamine synthetase gene, because at this region, the two genes differ substantially.

As those skilled in the art will appreciate, the production and use of antisense ODN in accordance with the teachings of the present invention is significantly more complex than the simple administration of an inhibitory antibiotic targeted at the extracellular enzyme. Nevertheless, either approach is effective in accomplishing the objectives of the present invention, effective treatment of disease conditions, although antibiotics are preferred for their ease of administration. For example, antibiotic compounds shown to be effective at inhibiting the functional activity of the targeted extracellular enzyme can be formulated for any convenient and commonly used mode of administration. These include injectable solutions, oral medications such as tablets, lozenges, capsules or solutions, aerosols, and virtually any other commonly used administrative technique. Where appropriate, excipients, carriers and adjuvants may be compounded with the antibiotic agent.

In selecting a suitable target for application of the present invention in the prophylactic and therapeutic treatment of disease conditions, those skilled in the art may wish to consider several factors and characteristics illustrated by the exemplary embodiments of the present invention discussed herein. For example, MS strongly inhibits, in dose-dependent fashion, *M. tuberculosis*, Erdman strain, *M. tuberculosis*, H37Rv strain, as well as *M. bovis* (strain 19210), *M. bovis* BCG, and *M. avium* which are pathogenic intracellular mycobacteria. MS does not inhibit the non-pathogenic mycobacteria *M. smegmatis* (strain 1–2c) and *M. phlei* (strain 11758), or the pathogenic non-mycobacterium *L. pneumophila* (strain Philadelphia 1), or the non-pathogenic, non-mycobacterium *E. coli* (strain DH5α). Thus, sensitivity to MS or to treatment with the present invention may be correlated with the organism being a pathogenic mycobacterium.

Additionally, it has been shown that pathogenic mycobacteria are unusual in that they release large amounts of glutamine synthetase extracellularly into the culture medium (Harth et al., op. cit.). Thus, sensitivity to MS or to treatment with the present invention also may be correlated with extracellular release of glutamine synthetase.

Further, all bacteria that release glutamine synthetase extracellularly into the culture medium in large quantities are inhibited by MS, and at similar concentrations. These include *M. tuberculosis, M. bovis* , and *M. avium*. Conversely, all bacteria evaluated that do not release glutamine synthetase extracellularly into the culture medium in large quantities are resistant to MS. These include *M. smegmatis, M. phlei, L. pneumophila*, and *E. coli*.

In order to be effective, any chemotherapeutic agent must be nontoxic to human cells. MS has been shown to exhibit no toxicity toward a human monocyte cell line, THP cells (ATCC TIB 202).

As discussed above, the reversal of the capacity of MS to inhibit *M. tuberculosis* by L-glutamine suggests that one mechanism by which MS inhibits *M. tuberculosis* growth is by reducing the availability of L-glutamine. In the absence of MS, or at a sub-inhibitory concentration, L-glutamine had no or little influence on *M. tuberculosis* growth. However, in the presence of inhibitory concentrations of MS, L-glutamine was found to reverse the inhibitory effect of MS in a dose-dependent fashion. In addition to its restriction of glutamine production, MS may inhibit the binding, transport, or linkage of L-glutamate and L-glutamine to the glutamate/glutamine polymer that is a characteristic feature of the cell wall of pathogenic mycobacteria, amounting to 10% of all cell wall components (Hirschfield, G. R., McNeil, M., and Brennan, A. J., 1990, *J. Bacteriol.* 172; 1005–1013).

Although not essential to the practice of the present invention, these factors provide helpful guidance to those skilled in the art who desire to duplicate the present invention in the context of different pathogens and extracellular cellular enzymes.

Although the enzyme inhibitors of the present invention have been exemplified by the compound L-methionine-S-sulfoximine, other related compounds, such as analogs of MS, can be used as well. In addition, inhibitors of other enzymes essential for the growth of pathogenic intracellular mycobacteria and other pathogenic bacteria can be used. For example, the functional activity of the 30–32 KD protein complex of *M. tuberculosis* (recently reported to have mycolyl transferase activity) the 45 KD protein, the 12 KD protein derived from a major membrane protein, the 14 KD protein, the 16 KD protein, the 23 KD protein (a superoxide dismutase), the 23.5 KD protein, the 24 KD protein, and the 71 KD heat shock protein chaperone can be inhibited using the present invention to inhibit the growth or survival of *M. tuberculosis* cells. Other enzymes which can be inhibited include the major secretary protein of *Legionella pneumophila* (a protease) and extracellular lipases of Trypanosoma.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A method for treating mammalian disease conditions associated with infection by pathogenic mycobacterium, said method comprising the steps of:
   administrating L-methionine-S-sulfoximine to a mammal in a dose sufficient to significantly inhibit the growth or survival of the pathogenic mycobacterium without harming said mammal.

2. The method in claim 1 wherein said pathogenic mycobacterium is a member selected from the group consisting of *M. tuberculosis, M. bovis, M. avium, M. kansasii, M. fortunitum, M. chelonei, M. marinum, M. scrofulaceum, M. leprae. M. africanum, M. ulcerans*, and *M microti*.

\* \* \* \* \*

UNITED STATES PATENT AND TRADEMARK OFFICE
CERTIFICATE OF CORRECTION

PATENT NO. : 6,013,660
DATED : January 11, 2000
INVENTOR(S) : Marcus A. Horwitz and Gunter Harth It is certified that error appears in the above-identified patent and that said Letters Patent is hereby corrected as shown below:

Column 1, line 7, following the number 35275 insert --and Grant No. AI31338--.

Signed and Sealed this

Sixth Day of February, 2001

Attest:

Attesting Officer

Q. TODD DICKINSON
Director of Patents and Trademarks